United States Patent
Ghasparian et al.

(10) Patent No.: US 9,943,583 B2
(45) Date of Patent: Apr. 17, 2018

(54) **PROLINE-RICH PEPTIDES PROTECTIVE AGAINST *S. PNEUMONIAE***

(71) Applicants: VIROMETIX AG, Schlieren (CH); SWISS TROPICAL AND PUBLIC HEALTH INSTITUTE, Basel (CH); UNIVERSITÄT BASEL, Basel (CH); UNIVERSITÄT ZÜRICH, Zürich (CH)

(72) Inventors: Arin Ghasparian, Zürich (CH); Armando Zuniga, Zürich (CH); Nina Geib, Zürich (CH); Marco Tamborini, Muttenz (CH); Maja Jud, Bottmingen (CH); Gerd Pluschke, Bad Krozingen (DE); Aniebrys Marrero Nodarse, Zürich (CH); John Anthony Robinson, Wermatswil (CH)

(73) Assignees: UNIVERSITÄT ZÜRICH, Zürich (CH); SWISS TROPICAL AND PUBLIC HEALTH INSTITUTE, Basel (CH); VIROMETIX AG, Schlieren (CH)

( * ) Notice: Subject to any disclaimer, the term of this patent is extended or adjusted under 35 U.S.C. 154(b) by 0 days.

(21) Appl. No.: 15/101,214

(22) PCT Filed: Dec. 2, 2014

(86) PCT No.: PCT/EP2014/076313
§ 371 (c)(1),
(2) Date: Jun. 2, 2016

(87) PCT Pub. No.: WO2015/082501
PCT Pub. Date: Jun. 11, 2015

(65) Prior Publication Data
US 2016/0324947 A1    Nov. 10, 2016

(30) Foreign Application Priority Data

Dec. 3, 2013 (EP) ..................................... 13195402

(51) Int. Cl.
*A61K 38/00* (2006.01)
*A61K 39/09* (2006.01)
*C07K 14/315* (2006.01)
*A61K 39/00* (2006.01)

(52) U.S. Cl.
CPC ........ *A61K 39/092* (2013.01); *C07K 14/3156* (2013.01); *A61K 2039/5258* (2013.01); *A61K 2039/55511* (2013.01); *A61K 2039/55516* (2013.01); *A61K 2039/575* (2013.01); *A61K 2039/6018* (2013.01); *C07K 2319/73* (2013.01)

(58) Field of Classification Search
CPC .. A61K 2039/5258; A61K 2039/55511; A61K 2039/55516; A61K 2039/575; A61K 2039/6018; A61K 39/092; C07K 14/3156; C07K 2319/73
See application file for complete search history.

(56) References Cited

U.S. PATENT DOCUMENTS

| 4,663,160 A | * | 5/1987 | Tsay | ..................... | A61K 39/104 |
| | | | | | 424/164.1 |
| 6,592,876 B1 | * | 7/2003 | Briles | .................. | A61K 39/092 |
| | | | | | 424/165.1 |

FOREIGN PATENT DOCUMENTS

| WO | 1996/40290 A1 | 12/1992 | | |
| WO | 2008/068017 A1 | 6/2008 | | |
| WO | WO2008/068017 | * | 6/2008 | ........... C07K 14/005 |
| WO | 2012/100233 A1 | 7/2012 | | |

OTHER PUBLICATIONS

Betts et al. Amino Acid Properties and Consequences of Substitutions. Chapter 14. Bioinformatics for Geneticists. 2003. pp. 289-316.*
Beall et al. Pneumococcal pspA Sequence Types of Prevalent Multiresistant Pneumococcal Strains in the United States and of Internationally Disseminated Clones. J Clin Microbiology, 2000. vol. 38, No. 10, pp. 3663-3669.*
Berndt et al., "Synthetic Lipidation of Peptides and Amino Acids: Monolayer Structure and Properties," Journal of the American Chemical Society 117(37):9515-9522 (1995).
Boato et al., "Synthetic Virus-Like Particles from Self-Assembling Coiled-Coil Lipopeptides and Their Use in Antigen Display to the Immune System," Angewandte Chemie 119:9173-9176 (2007).
Daniels et al., "The Proline-Rich Region of Pneumococcal Surface Proteins A and C Contains Surface-Accessible Epitopes Common to All Pneumococci and Elicits Antibody-Mediated Protection against Sepsis," Infection and Immunity 78(5):2163-2172 (2010).
Ghasparian et al., "Engineered Synthetic Virus-Like Particles and Their Use in Vaccine Delivery," ChemBioChem 12(1):100-109 (2011).
Jedrzejas et al., "Characterization of Selected Strains of Pneumococcal Surface Protein A," Journal of Biological Chemistry 276(35):33121-33128 (2001).
Langermann et al., "Protective Humoral Response Against Pneumococcal Infection in Mice Elicited by Recombinant Bacille Calmette-Guerin Vaccines Expressing Pneumococcal Surface Protein A," Journal of Experimental Medicine 180(6):2277-2286 (1994).

(Continued)

*Primary Examiner* — Marcela M Cordero Garcia
(74) *Attorney, Agent, or Firm* — Medler Ferro Woodhouse & Mills PLLC

(57) ABSTRACT

The invention relates to lipopeptides consisting of a peptide chain comprising a parallel coiled-coil domain, a proline-rich peptide antigen, and a lipid moiety, all covalently linked, which aggregate to synthetic virus-like particles. Proline-rich peptide antigens considered contain negatively and positively charged amino acid, and at least 15% of the amino acids are proline. Such synthetic virus-like particles carrying proline-rich antigens derived from pneumococcal proteins are useful as vaccines against infectious diseases caused by Gram-positive bacteria such as *Streptococcus pneumoniae*.

19 Claims, 1 Drawing Sheet

(56) References Cited

OTHER PUBLICATIONS

Melin et al., "Development of cross-reactive antibodies to the proline-rich region of pneumococcal surface protein A in children," Vaccine 30(50):7157-7160 (2012).
Riedel et al., "Synthetic Virus-Like Particles and Conformationally Constrained Peptidomimetics in Vaccine Design," ChemBioChem 12(18):2829-2836 (2011).
Sharma et al., "Synthetic Virus-Like Particles Target Dendritic Cell Lipid Rafts for Rapid Endocytosis Primarily but Not Exclusively by Macropinocytosis," PLoS One 7(8):e43248 (2012).
Woolfson, et al., "The Design of Coiled-Coil Structures and Assemblies," Advances in Protein Chemistry 70:79-112 (2005).
Yother et al., "Structural Properties and Evolutionary Relationships of PspA, a Surface Protein of *Streptococcus pneumoniae*, as Revealed by Sequence Analysis," Journal of Bacteriology 174(2):601-609 (1992).
International Search Report for PCT/EP2014/076313, dated Feb. 17, 2015.

\* cited by examiner

SEQUENCE LISTING

```
<160> NUMBER OF SEQ ID NOS: 133

<210> SEQ ID NO 1
<211> LENGTH: 14
<212> TYPE: PRT
<213> ORGANISM: Artificial
<220> FEATURE:
<223> OTHER INFORMATION: Synthetic construct

<400> SEQUENCE: 1

Gln Tyr Ile Lys Ala Asn Ser Lys Phe Ile Gly Ile Thr Glu
1               5                   10

<210> SEQ ID NO 2
<211> LENGTH: 16
<212> TYPE: PRT
<213> ORGANISM: Artificial
<220> FEATURE:
<223> OTHER INFORMATION: Synthetic construct

<400> SEQUENCE: 2

Ile Arg Glu Asp Asn Asn Ile Thr Leu Lys Leu Asp Arg Cys Asn Asn
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic construct

<400> SEQUENCE: 3

Val Ser Ile Asp Lys Phe Arg Ile Phe Cys Lys Ala Asn Pro Lys
1               5                   10                  15

<210> SEQ ID NO 4
<211> LENGTH: 22
<212> TYPE: PRT
<213> ORGANISM: Artificial
<220> FEATURE:
<223> OTHER INFORMATION: Synthetic construct

<400> SEQUENCE: 4

Phe Asn Asn Phe Thr Val Ser Phe Trp Leu Arg Val Pro Lys Val Ser
1               5                   10                  15
```

Ala Ser His Leu Glu Thr
            20

<210> SEQ ID NO 5
<211> LENGTH: 16
<212> TYPE: PRT
<213> ORGANISM: Artificial
<220> FEATURE:
<223> OTHER INFORMATION: Synthetic construct

<400> SEQUENCE: 5

Leu Lys Phe Ile Ile Lys Arg Tyr Thr Pro Asn Asn Glu Ile Asp Ser
1               5                   10                  15

<210> SEQ ID NO 6
<211> LENGTH: 20
<212> TYPE: PRT
<213> ORGANISM: Artificial
<220> FEATURE:
<223> OTHER INFORMATION: Synthetic construct

<400> SEQUENCE: 6

Pro Val Phe Ala Gly Ala Asn Tyr Ala Ala Trp Ala Val Asn Val Ala
1               5                   10                  15

Gln Val Ile Asp
            20

<210> SEQ ID NO 7
<211> LENGTH: 20
<212> TYPE: PRT
<213> ORGANISM: Artificial
<220> FEATURE:
<223> OTHER INFORMATION: Synthetic construct

<400> SEQUENCE: 7

Val His His Asn Thr Glu Glu Ile Val Ala Gln Ser Ile Ala Leu Ser
1               5                   10                  15

Ser Leu Met Val
            20

<210> SEQ ID NO 8
<211> LENGTH: 20
<212> TYPE: PRT
<213> ORGANISM: Artificial
<220> FEATURE:
<223> OTHER INFORMATION: Synthetic construct

<400> SEQUENCE: 8

Gln Ser Ile Ala Leu Ser Ser Leu Met Val Ala Gln Ala Ile Pro Leu
1               5                   10                  15

Val Gly Glu Leu
            20

<210> SEQ ID NO 9
<211> LENGTH: 20
<212> TYPE: PRT
<213> ORGANISM: Artificial
<220> FEATURE:
<223> OTHER INFORMATION: Synthetic construct

<400> SEQUENCE: 9

Val Asp Ile Gly Phe Ala Ala Tyr Asn Phe Val Glu Ser Ile Ile Asn
1               5                   10                  15

Leu Phe Gln Val

```
                        20

<210> SEQ ID NO 10
<211> LENGTH: 20
<212> TYPE: PRT
<213> ORGANISM: Artificial
<220> FEATURE:
<223> OTHER INFORMATION: Synthetic construct

<400> SEQUENCE: 10

Gln Gly Glu Ser Gly His Asp Ile Lys Ile Thr Ala Glu Asn Thr Pro
1               5                   10                  15

Leu Pro Ile Ala
            20

<210> SEQ ID NO 11
<211> LENGTH: 20
<212> TYPE: PRT
<213> ORGANISM: Artificial
<220> FEATURE:
<223> OTHER INFORMATION: Synthetic construct

<400> SEQUENCE: 11

Gly Val Leu Leu Pro Thr Ile Pro Gly Lys Leu Asp Val Asn Lys Ser
1               5                   10                  15

Lys Thr His Ile
            20

<210> SEQ ID NO 12
<211> LENGTH: 20
<212> TYPE: PRT
<213> ORGANISM: Artificial
<220> FEATURE:
<223> OTHER INFORMATION: Synthetic construct

<400> SEQUENCE: 12

Thr Ile Asp Lys Ile Ser Asp Val Ser Thr Ile Val Pro Tyr Ile Gly
1               5                   10                  15

Pro Ala Leu Asn
            20

<210> SEQ ID NO 13
<211> LENGTH: 25
<212> TYPE: PRT
<213> ORGANISM: Artificial
<220> FEATURE:
<223> OTHER INFORMATION: Synthetic construct

<400> SEQUENCE: 13

Ala Leu Asn Ile Trp Asp Arg Phe Asp Val Phe Cys Thr Leu Gly Ala
1               5                   10                  15

Thr Thr Gly Tyr Leu Lys Gly Asn Ser
            20                  25

<210> SEQ ID NO 14
<211> LENGTH: 14
<212> TYPE: PRT
<213> ORGANISM: Artificial
<220> FEATURE:
<223> OTHER INFORMATION: Synthetic construct

<400> SEQUENCE: 14

Gly Leu Gln Gly Lys Ile Ala Asp Ala Val Lys Ala Lys Gly
1               5                   10
```

-continued

<210> SEQ ID NO 15
<211> LENGTH: 19
<212> TYPE: PRT
<213> ORGANISM: Artificial
<220> FEATURE:
<223> OTHER INFORMATION: Synthetic construct

<400> SEQUENCE: 15

Gly Leu Ala Ala Gly Leu Val Gly Met Ala Ala Asp Ala Met Val Glu
1               5                   10                  15

Asp Val Asn

<210> SEQ ID NO 16
<211> LENGTH: 20
<212> TYPE: PRT
<213> ORGANISM: Artificial
<220> FEATURE:
<223> OTHER INFORMATION: Synthetic construct

<400> SEQUENCE: 16

Ser Thr Glu Thr Gly Asn Gln His His Tyr Gln Thr Arg Val Val Ser
1               5                   10                  15

Asn Ala Asn Lys
            20

<210> SEQ ID NO 17
<211> LENGTH: 20
<212> TYPE: PRT
<213> ORGANISM: Artificial
<220> FEATURE:
<223> OTHER INFORMATION: Synthetic construct

<400> SEQUENCE: 17

Pro His His Thr Ala Leu Arg Gln Ala Ile Leu Cys Trp Gly Glu Leu
1               5                   10                  15

Met Thr Leu Ala
            20

<210> SEQ ID NO 18
<211> LENGTH: 15
<212> TYPE: PRT
<213> ORGANISM: Artificial
<220> FEATURE:
<223> OTHER INFORMATION: Synthetic construct

<400> SEQUENCE: 18

Phe Phe Leu Leu Thr Arg Ile Leu Thr Ile Pro Gln Ser Leu Asp
1               5                   10                  15

<210> SEQ ID NO 19
<211> LENGTH: 13
<212> TYPE: PRT
<213> ORGANISM: Artificial
<220> FEATURE:
<223> OTHER INFORMATION: Synthetic construct

<400> SEQUENCE: 19

Pro Lys Tyr Val Lys Gln Asn Thr Leu Lys Leu Ala Thr
1               5                   10

<210> SEQ ID NO 20
<211> LENGTH: 16
<212> TYPE: PRT
<213> ORGANISM: Artificial
<220> FEATURE:

```
<223> OTHER INFORMATION: Synthetic construct

<400> SEQUENCE: 20

Tyr Ser Gly Pro Leu Lys Ala Glu Ile Ala Gln Arg Leu Glu Asp Val
1               5                   10                  15

<210> SEQ ID NO 21
<211> LENGTH: 20
<212> TYPE: PRT
<213> ORGANISM: Artificial
<220> FEATURE:
<223> OTHER INFORMATION: Synthetic construct

<400> SEQUENCE: 21

Gly Ile Leu Glu Ser Arg Gly Ile Lys Ala Arg Ile Thr His Val Asp
1               5                   10                  15

Thr Glu Ser Tyr
            20

<210> SEQ ID NO 22
<211> LENGTH: 15
<212> TYPE: PRT
<213> ORGANISM: Artificial
<220> FEATURE:
<223> OTHER INFORMATION: Synthetic construct

<400> SEQUENCE: 22

Leu Ser Glu Ile Lys Gly Val Ile Val His Arg Leu Glu Gly Val
1               5                   10                  15

<210> SEQ ID NO 23
<211> LENGTH: 20
<212> TYPE: PRT
<213> ORGANISM: Artificial
<220> FEATURE:
<223> OTHER INFORMATION: Synthetic construct

<400> SEQUENCE: 23

Ile Glu Lys Lys Ile Ala Lys Met Glu Lys Ala Ser Ser Val Phe Asn
1               5                   10                  15

Val Val Asn Ser
            20

<210> SEQ ID NO 24
<211> LENGTH: 17
<212> TYPE: PRT
<213> ORGANISM: Artificial
<220> FEATURE:
<223> OTHER INFORMATION: Synthetic construct

<400> SEQUENCE: 24

Lys Trp Phe Lys Thr Asn Ala Pro Asn Gly Val Asp Glu Lys Ile Arg
1               5                   10                  15

Ile

<210> SEQ ID NO 25
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(1)
<223> OTHER INFORMATION: D-alanine
<220> FEATURE:
```

```
<221> NAME/KEY: X
<222> LOCATION: (13)..(13)
<223> OTHER INFORMATION: D-alanine

<400> SEQUENCE: 25

Xaa Lys Phe Val Ala Ala Trp Thr Leu Lys Ala Ala Xaa
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic construct
<220> FEATURE:
<221> NAME/KEY: X
<222> LOCATION: (1)..(1)
<223> OTHER INFORMATION: D-alanine
<220> FEATURE:
<221> NAME/KEY: X
<222> LOCATION: (3)..(3)
<223> OTHER INFORMATION: cyclohexyl-alanine
<220> FEATURE:
<221> NAME/KEY: X
<222> LOCATION: (13)..(13)
<223> OTHER INFORMATION: D-alanine

<400> SEQUENCE: 26

Xaa Lys Xaa Val Ala Ala Trp Thr Leu Lys Ala Ala Xaa
1               5                   10

<210> SEQ ID NO 27
<211> LENGTH: 29
<212> TYPE: PRT
<213> ORGANISM: Streptococcus pneumoniae

<400> SEQUENCE: 27

Pro Ala Pro Lys Pro Glu Gln Pro Ala Glu Gln Pro Lys Pro Ala Pro
1               5                   10                  15

Ala Pro Gln Pro Ala Pro Ala Pro Lys Pro Glu Lys Thr
            20                  25

<210> SEQ ID NO 28
<211> LENGTH: 22
<212> TYPE: PRT
<213> ORGANISM: Streptococcus pneumoniae

<400> SEQUENCE: 28

Pro Lys Pro Glu Gln Pro Ala Pro Ala Pro Lys Pro Glu Gln Pro Ala
1               5                   10                  15

Lys Pro Glu Lys Pro Ala
            20

<210> SEQ ID NO 29
<211> LENGTH: 32
<212> TYPE: PRT
<213> ORGANISM: Artificial
<220> FEATURE:
<223> OTHER INFORMATION: Synthetic construct

<400> SEQUENCE: 29

Pro Ala Pro Lys Pro Glu Gln Pro Ala Glu Gln Pro Lys Pro Glu Gln
1               5                   10                  15

Pro Ala Pro Ala Pro Lys Pro Glu Gln Pro Ala Lys Pro Glu Lys Pro
            20                  25                  30
```

```
<210> SEQ ID NO 30
<211> LENGTH: 15
<212> TYPE: PRT
<213> ORGANISM: Streptococcus pneumoniae

<400> SEQUENCE: 30

Pro Ala Pro Lys Pro Glu Gln Pro Ala Glu Gln Pro Lys Pro Ala
1               5                   10                  15

<210> SEQ ID NO 31
<211> LENGTH: 14
<212> TYPE: PRT
<213> ORGANISM: Streptococcus pneumoniae

<400> SEQUENCE: 31

Pro Ala Pro Gln Pro Ala Pro Ala Pro Lys Pro Glu Lys Thr
1               5                   10

<210> SEQ ID NO 32
<211> LENGTH: 16
<212> TYPE: PRT
<213> ORGANISM: Streptococcus pneumoniae

<400> SEQUENCE: 32

Gln Pro Ala Glu Gln Pro Lys Pro Ala Pro Ala Pro Gln Pro Ala Pro
1               5                   10                  15

<210> SEQ ID NO 33
<211> LENGTH: 16
<212> TYPE: PRT
<213> ORGANISM: Streptococcus pneumoniae

<400> SEQUENCE: 33

Pro Ala Pro Ala Pro Lys Pro Glu Gln Pro Ala Glu Gln Pro Lys Pro
1               5                   10                  15

<210> SEQ ID NO 34
<211> LENGTH: 36
<212> TYPE: PRT
<213> ORGANISM: Streptococcus pneumoniae

<400> SEQUENCE: 34

Pro Ala Pro Glu Ala Pro Ala Glu Gln Pro Lys Pro Ala Pro Ala Pro
1               5                   10                  15

Gln Pro Ala Pro Ala Pro Lys Pro Glu Lys Pro Ala Glu Gln Pro Lys
                20                  25                  30

Pro Glu Lys Thr
                35

<210> SEQ ID NO 35
<211> LENGTH: 25
<212> TYPE: PRT
<213> ORGANISM: Streptococcus pneumoniae

<400> SEQUENCE: 35

Pro Ala Glu Gln Pro Lys Pro Ala Pro Ala Pro Gln Pro Ala Pro Ala
1               5                   10                  15

Pro Lys Pro Glu Lys Pro Ala Glu Gln
                20                  25

<210> SEQ ID NO 36
<211> LENGTH: 27
<212> TYPE: PRT
<213> ORGANISM: Streptococcus pneumoniae
```

```
<400> SEQUENCE: 36

Pro Lys Pro Ala Pro Ala Pro Gln Pro Ala Pro Ala Pro Lys Pro Glu
1               5                   10                  15
Lys Pro Ala Glu Gln Pro Lys Pro Glu Lys Thr
            20                  25

<210> SEQ ID NO 37
<211> LENGTH: 20
<212> TYPE: PRT
<213> ORGANISM: Streptococcus pneumoniae

<400> SEQUENCE: 37

Lys Ala Glu Lys Pro Ala Pro Ala Pro Gln Pro Glu Gln Pro Ala Pro
1               5                   10                  15
Ala Pro Lys Thr
            20

<210> SEQ ID NO 38
<211> LENGTH: 40
<212> TYPE: PRT
<213> ORGANISM: Streptococcus pneumoniae

<400> SEQUENCE: 38

Pro Ala Pro Ala Pro Gln Pro Glu Gln Pro Ala Pro Ala Pro Gln Pro
1               5                   10                  15
Glu Gln Pro Ala Pro Ala Pro Lys Pro Glu Gln Pro Ala Pro Ala Pro
            20                  25                  30
Lys Pro Glu Gln Pro Thr Pro Ala
        35                  40

<210> SEQ ID NO 39
<211> LENGTH: 43
<212> TYPE: PRT
<213> ORGANISM: Streptococcus pneumoniae

<400> SEQUENCE: 39

Pro Ala Pro Ala Pro Gln Pro Glu Gln Pro Ala Pro Ala Pro Lys Pro
1               5                   10                  15
Glu Gln Pro Ala Pro Ala Pro Lys Pro Glu Gln Pro Thr Pro Ala Pro
            20                  25                  30
Lys Pro Glu Gln Pro Thr Pro Ala Pro Lys Thr
        35                  40

<210> SEQ ID NO 40
<211> LENGTH: 37
<212> TYPE: PRT
<213> ORGANISM: Streptococcus pneumoniae

<400> SEQUENCE: 40

Pro Glu Gln Pro Ala Pro Ala Pro Lys Pro Glu Gln Pro Ala Pro Ala
1               5                   10                  15
Pro Lys Pro Glu Gln Pro Thr Pro Ala Pro Lys Pro Glu Gln Pro Thr
            20                  25                  30
Pro Ala Pro Lys Thr
        35

<210> SEQ ID NO 41
<211> LENGTH: 21
<212> TYPE: PRT
<213> ORGANISM: Streptococcus pneumoniae
```

<400> SEQUENCE: 41

Pro Lys Pro Glu Gln Pro Thr Pro Ala Pro Lys Pro Glu Gln Pro Thr
1               5                   10                  15

Pro Ala Pro Lys Thr
            20

<210> SEQ ID NO 42
<211> LENGTH: 17
<212> TYPE: PRT
<213> ORGANISM: Streptococcus pneumoniae

<400> SEQUENCE: 42

Pro Lys Pro Glu Gln Pro Ala Glu Gln Pro Lys Pro Ala Pro Ala Pro
1               5                   10                  15

Gln

<210> SEQ ID NO 43
<211> LENGTH: 36
<212> TYPE: PRT
<213> ORGANISM: Streptococcus pneumoniae

<400> SEQUENCE: 43

Pro Lys Pro Glu Gln Pro Ala Pro Ala Pro Lys Pro Glu Gln Pro Ala
1               5                   10                  15

Lys Pro Glu Lys Pro Ala Glu Glu Pro Thr Gln Pro Glu Lys Pro Ala
                20                  25                  30

Thr Pro Lys Thr
        35

<210> SEQ ID NO 44
<211> LENGTH: 27
<212> TYPE: PRT
<213> ORGANISM: Streptococcus pneumoniae

<400> SEQUENCE: 44

Pro Lys Pro Glu Gln Pro Ala Lys Pro Glu Lys Pro Ala Glu Glu Pro
1               5                   10                  15

Thr Gln Pro Glu Lys Pro Ala Thr Pro Lys Thr
            20                  25

<210> SEQ ID NO 45
<211> LENGTH: 32
<212> TYPE: PRT
<213> ORGANISM: Streptococcus pneumoniae

<400> SEQUENCE: 45

Pro Ala Pro Ala Pro Gln Pro Ala Pro Ala Pro Lys Pro Ala Pro Ala
1               5                   10                  15

Pro Gln Pro Glu Lys Pro Ala Glu Gln Pro Lys Ala Glu Lys Pro Ala
            20                  25                  30

<210> SEQ ID NO 46
<211> LENGTH: 41
<212> TYPE: PRT
<213> ORGANISM: Streptococcus pneumoniae

<400> SEQUENCE: 46

Pro Glu Thr Pro Ala Pro Ala Pro Lys Pro Glu Thr Pro Ala Pro Ala
1               5                   10                  15

Pro Glu Ala Pro Ala Pro Ala Pro Ala Pro Lys Pro Glu Gln Pro Ala

```
                20                  25                  30

Pro Ala Pro Lys Pro Glu Lys Ser Ala
        35                  40

<210> SEQ ID NO 47
<211> LENGTH: 20
<212> TYPE: PRT
<213> ORGANISM: Streptococcus pneumoniae

<400> SEQUENCE: 47

Pro Ala Pro Ala Pro Lys Pro Glu Gln Pro Ala Pro Ala Pro Lys Pro
1               5                   10                  15

Glu Lys Ser Ala
        20

<210> SEQ ID NO 48
<211> LENGTH: 16
<212> TYPE: PRT
<213> ORGANISM: Streptococcus pneumoniae

<400> SEQUENCE: 48

Pro Lys Pro Glu Gln Pro Ala Pro Ala Pro Lys Pro Glu Lys Ser Ala
1               5                   10                  15

<210> SEQ ID NO 49
<211> LENGTH: 20
<212> TYPE: PRT
<213> ORGANISM: Streptococcus pneumoniae

<400> SEQUENCE: 49

Lys Ala Glu Lys Pro Ala Pro Ala Pro Lys Pro Glu Gln Pro Val Pro
1               5                   10                  15

Ala Pro Lys Thr
        20

<210> SEQ ID NO 50
<211> LENGTH: 28
<212> TYPE: PRT
<213> ORGANISM: Streptococcus pneumoniae

<400> SEQUENCE: 50

Pro Ala Pro Ala Pro Lys Pro Ala Pro Ala Gln Pro Glu Lys Pro
1               5                   10                  15

Ala Pro Ala Pro Ala Pro Lys Pro Glu Lys Ser Ala
        20                  25

<210> SEQ ID NO 51
<211> LENGTH: 36
<212> TYPE: PRT
<213> ORGANISM: Streptococcus pneumoniae

<400> SEQUENCE: 51

Pro Ala Pro Glu Gln Pro Thr Glu Pro Thr Gln Pro Glu Lys Pro Ala
1               5                   10                  15

Glu Glu Thr Pro Ala Pro Lys Pro Glu Lys Pro Ala Glu Gln Pro Lys
        20                  25                  30

Ala Glu Lys Thr
        35

<210> SEQ ID NO 52
<211> LENGTH: 17
<212> TYPE: PRT
```

<213> ORGANISM: Streptococcus pneumoniae

<400> SEQUENCE: 52

Pro Ala Pro Lys Pro Glu Lys Pro Ala Glu Gln Pro Lys Ala Glu Lys
1               5                   10                  15

Thr

<210> SEQ ID NO 53
<211> LENGTH: 36
<212> TYPE: PRT
<213> ORGANISM: Streptococcus pneumoniae

<400> SEQUENCE: 53

Pro Ala Pro Ala Pro Lys Pro Glu Gln Pro Ala Glu Gln Pro Lys Pro
1               5                   10                  15

Ala Pro Ala Pro Gln Pro Glu Lys Pro Ala Glu Glu Pro Glu Asn Pro
                20                  25                  30

Ala Pro Ala Pro
        35

<210> SEQ ID NO 54
<211> LENGTH: 36
<212> TYPE: PRT
<213> ORGANISM: Streptococcus pneumoniae

<400> SEQUENCE: 54

Ala Pro Ala Pro Lys Pro Glu Thr Pro Ala Pro Ala Pro Glu Ala Pro
1               5                   10                  15

Ala Pro Ala Pro Ala Pro Lys Pro Glu Gln Pro Ala Pro Ala Pro Lys
                20                  25                  30

Pro Glu Lys Ser
        35

<210> SEQ ID NO 55
<211> LENGTH: 42
<212> TYPE: PRT
<213> ORGANISM: Streptococcus pneumoniae

<400> SEQUENCE: 55

Ala Pro Ala Pro Glu Thr Pro Ala Pro Glu Ala Pro Ala Glu Gln Pro
1               5                   10                  15

Lys Pro Ala Pro Ala Pro Gln Pro Ala Pro Ala Pro Lys Pro Glu Lys
                20                  25                  30

Pro Ala Glu Gln Pro Lys Pro Glu Lys Thr
        35                  40

<210> SEQ ID NO 56
<211> LENGTH: 36
<212> TYPE: PRT
<213> ORGANISM: Streptococcus pneumoniae

<400> SEQUENCE: 56

Pro Ala Pro Glu Gln Pro Thr Glu Pro Thr Gln Pro Glu Lys Pro Ala
1               5                   10                  15

Glu Glu Thr Pro Ala Pro Lys Pro Glu Lys Pro Ala Glu Gln Pro Lys
                20                  25                  30

Ala Glu Lys Thr
        35

<210> SEQ ID NO 57

```
<211> LENGTH: 36
<212> TYPE: PRT
<213> ORGANISM: Streptococcus pneumoniae

<400> SEQUENCE: 57

Ala Pro Ala Pro Lys Pro Glu Thr Pro Ala Pro Ala Pro Glu Ala Pro
1               5                   10                  15

Ala Pro Ala Pro Ala Pro Lys Pro Glu Gln Pro Ala Pro Ala Pro Lys
            20                  25                  30

Pro Glu Lys Ser
        35

<210> SEQ ID NO 58
<211> LENGTH: 42
<212> TYPE: PRT
<213> ORGANISM: Streptococcus pneumoniae

<400> SEQUENCE: 58

Ala Pro Ala Pro Glu Thr Pro Ala Pro Glu Ala Pro Ala Gln Pro
1               5                   10                  15

Lys Pro Ala Pro Ala Pro Gln Pro Ala Pro Ala Pro Lys Pro Glu Lys
            20                  25                  30

Pro Ala Glu Gln Pro Lys Pro Glu Lys Thr
        35                  40

<210> SEQ ID NO 59
<211> LENGTH: 36
<212> TYPE: PRT
<213> ORGANISM: Streptococcus pneumoniae

<400> SEQUENCE: 59

Ala Pro Ala Pro Lys Pro Glu Thr Pro Ala Pro Ala Pro Glu Ala Pro
1               5                   10                  15

Ala Pro Ala Pro Ala Pro Lys Pro Glu Gln Pro Ala Pro Ala Pro Lys
            20                  25                  30

Pro Glu Lys Ser
        35

<210> SEQ ID NO 60
<211> LENGTH: 42
<212> TYPE: PRT
<213> ORGANISM: Streptococcus pneumoniae

<400> SEQUENCE: 60

Ala Pro Ala Pro Glu Thr Pro Ala Pro Glu Ala Pro Ala Gln Pro
1               5                   10                  15

Lys Pro Ala Pro Ala Pro Gln Pro Ala Pro Ala Pro Lys Pro Glu Lys
            20                  25                  30

Pro Ala Glu Gln Pro Lys Pro Glu Lys Thr
        35                  40

<210> SEQ ID NO 61
<211> LENGTH: 43
<212> TYPE: PRT
<213> ORGANISM: Streptococcus pneumoniae

<400> SEQUENCE: 61

Ala Pro Ala Pro Glu Thr Pro Ala Pro Glu Ala Pro Ala Gln Pro
1               5                   10                  15

Lys Pro Ala Pro Ala Pro Gln Pro Ala Pro Ala Pro Lys Pro Glu Lys
            20                  25                  30
```

Pro Ala Glu Gln Pro Lys Ala Glu Lys Pro Ala
        35                  40

<210> SEQ ID NO 62
<211> LENGTH: 33
<212> TYPE: PRT
<213> ORGANISM: Streptococcus pneumoniae

<400> SEQUENCE: 62

Pro Gln Pro Glu Gln Pro Ala Pro Ala Pro Lys Pro Glu Gln Pro Ala
1               5                   10                  15

Pro Ala Pro Lys Pro Glu Gln Pro Thr Pro Ala Pro Lys Pro Glu His
            20                  25                  30

Pro

<210> SEQ ID NO 63
<211> LENGTH: 35
<212> TYPE: PRT
<213> ORGANISM: Streptococcus pneumoniae

<400> SEQUENCE: 63

Pro Ala Pro Ala Pro Gln Pro Glu Gln Pro Ala Pro Ala Pro Gln Pro
1               5                   10                  15

Glu Gln Pro Ala Pro Ala Pro Lys Pro Glu Gln Pro Ala Pro Ala Pro
            20                  25                  30

Lys Pro Glu
        35

<210> SEQ ID NO 64
<211> LENGTH: 33
<212> TYPE: PRT
<213> ORGANISM: Streptococcus pneumoniae

<400> SEQUENCE: 64

Pro Ala Pro Gln Pro Glu Gln Pro Ala Pro Ala Pro Lys Pro Glu Gln
1               5                   10                  15

Pro Ala Pro Ala Pro Lys Pro Glu Gln Pro Thr Pro Ala Pro Lys Pro
            20                  25                  30

Pro

<210> SEQ ID NO 65
<211> LENGTH: 35
<212> TYPE: PRT
<213> ORGANISM: Streptococcus pneumoniae

<400> SEQUENCE: 65

Pro Ala Pro Ala Pro Ala Pro Lys Pro Glu Gln Pro Ala Pro Ala Pro
1               5                   10                  15

Ala Pro Lys Pro Glu Gln Pro Ala Pro Ala Pro Ala Pro Lys Pro Glu
            20                  25                  30

Gln Pro Ala
        35

<210> SEQ ID NO 66
<211> LENGTH: 33
<212> TYPE: PRT
<213> ORGANISM: Streptococcus pneumoniae

<400> SEQUENCE: 66

Pro Ala Pro Ala Pro Lys Pro Glu Gln Pro Ala Pro Ala Pro Ala Pro

```
1               5                   10                  15
Lys Pro Glu Gln Pro Ala Pro Ala Pro Lys Pro Glu Gln Pro
            20                  25                  30
Thr

<210> SEQ ID NO 67
<211> LENGTH: 35
<212> TYPE: PRT
<213> ORGANISM: Streptococcus pneumoniae

<400> SEQUENCE: 67

Pro Ala Pro Ala Pro Gln Pro Glu Gln Pro Ala Pro Ala Pro Lys Pro
1               5                   10                  15
Glu Gln Pro Ala Pro Ala Pro Lys Pro Glu Gln Pro Thr Pro Ala Pro
            20                  25                  30
Lys Pro Glu
        35

<210> SEQ ID NO 68
<211> LENGTH: 31
<212> TYPE: PRT
<213> ORGANISM: Streptococcus pneumoniae

<400> SEQUENCE: 68

Pro Ala Pro Ala Pro Lys Pro Glu Gln Pro Ala Glu Gln Pro Lys Pro
1               5                   10                  15
Ala Pro Ala Pro Gln Pro Ala Pro Ala Pro Lys Pro Glu Lys Gln
            20                  25                  30

<210> SEQ ID NO 69
<211> LENGTH: 35
<212> TYPE: PRT
<213> ORGANISM: Streptococcus pneumoniae

<400> SEQUENCE: 69

Pro Ala Pro Ala Pro Gln Pro Glu Gln Pro Ala Pro Ala Pro Gln Pro
1               5                   10                  15
Glu Gln Pro Ala Pro Ala Pro Lys Pro Glu Gln Pro Ala Pro Ala Pro
            20                  25                  30
Lys Pro Ala
        35

<210> SEQ ID NO 70
<211> LENGTH: 34
<212> TYPE: PRT
<213> ORGANISM: Streptococcus pneumoniae

<400> SEQUENCE: 70

Pro Lys Pro Glu Gln Pro Thr Pro Ala Pro Lys Pro Glu Gln Pro Thr
1               5                   10                  15
Pro Ala Pro Lys Pro Glu Gln Pro Thr Pro Ala Pro Lys Pro Glu Gln
            20                  25                  30
Pro Thr

<210> SEQ ID NO 71
<211> LENGTH: 21
<212> TYPE: PRT
<213> ORGANISM: Streptococcus pneumoniae

<400> SEQUENCE: 71
```

Pro Glu Lys Pro Ala Pro Ala Pro Glu Lys Pro Ala Pro Ala Pro Glu
1               5                   10                  15

Lys Pro Ala Pro Ala
            20

<210> SEQ ID NO 72
<211> LENGTH: 23
<212> TYPE: PRT
<213> ORGANISM: Streptococcus pneumoniae

<400> SEQUENCE: 72

Pro Ala Pro Lys Pro Ala Pro Ala Pro Lys Pro Ala Pro Ala Pro Ala
1               5                   10                  15

Pro Lys Pro Glu Lys Pro Ala
            20

<210> SEQ ID NO 73
<211> LENGTH: 16
<212> TYPE: PRT
<213> ORGANISM: Streptococcus pneumoniae

<400> SEQUENCE: 73

Pro Ala Pro Ala Pro Thr Pro Glu Ala Pro Ala Pro Ala Pro Lys Pro
1               5                   10                  15

<210> SEQ ID NO 74
<211> LENGTH: 23
<212> TYPE: PRT
<213> ORGANISM: Streptococcus pneumoniae

<400> SEQUENCE: 74

Pro Lys Pro Glu Gln Pro Ala Lys Pro Glu Lys Pro Ala Glu Glu Pro
1               5                   10                  15

Thr Gln Pro Glu Lys Pro Ala
            20

<210> SEQ ID NO 75
<211> LENGTH: 18
<212> TYPE: PRT
<213> ORGANISM: Streptococcus pneumoniae

<400> SEQUENCE: 75

Pro Ala Lys Pro Glu Lys Pro Ala Glu Glu Pro Thr Gln Pro Glu Lys
1               5                   10                  15

Pro Ala

<210> SEQ ID NO 76
<211> LENGTH: 27
<212> TYPE: PRT
<213> ORGANISM: Streptococcus pneumoniae

<400> SEQUENCE: 76

Pro Ala Pro Ala Pro Lys Pro Glu Gln Pro Ala Lys Pro Glu Lys Pro
1               5                   10                  15

Ala Glu Glu Pro Thr Gln Pro Glu Lys Pro Ala
            20                  25

<210> SEQ ID NO 77
<211> LENGTH: 32
<212> TYPE: PRT
<213> ORGANISM: Streptococcus pneumoniae

<400> SEQUENCE: 77

```
Pro Lys Pro Glu Gln Pro Ala Pro Ala Pro Asn Pro Glu Gln Pro Ala
1               5                   10                  15

Lys Pro Glu Lys Pro Ala Glu Glu Pro Thr Gln Pro Glu Lys Pro Ala
            20                  25                  30
```

<210> SEQ ID NO 78
<211> LENGTH: 29
<212> TYPE: PRT
<213> ORGANISM: Streptococcus pneumoniae

<400> SEQUENCE: 78

```
Pro Lys Pro Glu Gln Pro Ala Pro Ala Pro Lys Pro Glu Gln
1               5                   10                  15

Pro Ala Pro Ala Pro Ala Pro Lys Pro Glu Gln Pro Ala
            20                  25
```

<210> SEQ ID NO 79
<211> LENGTH: 32
<212> TYPE: PRT
<213> ORGANISM: Streptococcus pneumoniae

<400> SEQUENCE: 79

```
Pro Lys Pro Glu Gln Pro Ala Pro Ala Pro Lys Pro Glu Gln Pro Ala
1               5                   10                  15

Lys Pro Glu Lys Pro Ala Glu Glu Pro Thr Gln Pro Glu Lys Pro Ala
            20                  25                  30
```

<210> SEQ ID NO 80
<211> LENGTH: 32
<212> TYPE: PRT
<213> ORGANISM: Streptococcus pneumoniae

<400> SEQUENCE: 80

```
Pro Lys Pro Glu Gln Pro Ala Pro Ala Pro Lys Pro Glu Gln Pro Ala
1               5                   10                  15

Lys Pro Glu Lys Pro Ala Glu Glu Pro Thr Gln Pro Glu Lys Pro Ala
            20                  25                  30
```

<210> SEQ ID NO 81
<211> LENGTH: 38
<212> TYPE: PRT
<213> ORGANISM: Streptococcus pneumoniae

<400> SEQUENCE: 81

```
Pro Ala Pro Ala Pro Gln Pro Glu Gln Pro Ala Pro Ala Pro Lys Pro
1               5                   10                  15

Glu Gln Pro Ala Pro Ala Pro Lys Pro Glu Gln Pro Ala Pro Ala Pro
            20                  25                  30

Lys Pro Glu Gln Pro Ala
        35
```

<210> SEQ ID NO 82
<211> LENGTH: 43
<212> TYPE: PRT
<213> ORGANISM: Streptococcus pneumoniae

<400> SEQUENCE: 82

```
Pro Ala Pro Ala Pro Lys Pro Glu Gln Pro Thr Pro Ala Pro Lys Pro
1               5                   10                  15

Glu Gln Pro Thr Pro Ala Pro Lys Pro Glu Gln Pro Ala Pro Ala Pro
            20                  25                  30
```

Lys Pro Glu Gln Pro Ala Pro Ala Pro Lys Pro
        35                  40

<210> SEQ ID NO 83
<211> LENGTH: 43
<212> TYPE: PRT
<213> ORGANISM: Streptococcus pneumoniae

<400> SEQUENCE: 83

Pro Ala Arg Ala Leu Gln Pro Glu Gln Pro Ala Pro Ala Pro Lys Pro
1               5                   10                  15

Glu Gln Pro Thr Pro Ala Pro Lys Pro Glu Gln Pro Thr Pro Ala Pro
            20                  25                  30

Lys Pro Glu Gln Pro Ala Pro Ala Pro Lys Pro
        35                  40

<210> SEQ ID NO 84
<211> LENGTH: 23
<212> TYPE: PRT
<213> ORGANISM: Streptococcus pneumoniae

<400> SEQUENCE: 84

Ser Arg Leu Glu Gln Pro Ser Leu Gln Pro Thr Pro Glu Pro Ser Pro
1               5                   10                  15

Gly Pro Gln Pro Ala Pro Asn
            20

<210> SEQ ID NO 85
<211> LENGTH: 24
<212> TYPE: PRT
<213> ORGANISM: Streptococcus pneumoniae

<400> SEQUENCE: 85

Arg Pro Glu Glu Pro Ser Pro Gln Pro Thr Pro Glu Pro Ser Pro Ser
1               5                   10                  15

Pro Gln Pro Ala Pro Ser Asn Pro
            20

<210> SEQ ID NO 86
<211> LENGTH: 36
<212> TYPE: PRT
<213> ORGANISM: Streptococcus pneumoniae

<400> SEQUENCE: 86

His Trp Val Pro Asp Ser Arg Pro Glu Gln Pro Ser Pro Gln Ser Thr
1               5                   10                  15

Pro Glu Pro Ser Pro Ser Pro Gln Pro Ala Pro Asn Pro Gln Pro Ala
            20                  25                  30

Pro Ser Asn Pro
        35

<210> SEQ ID NO 87
<211> LENGTH: 32
<212> TYPE: PRT
<213> ORGANISM: Streptococcus pneumoniae

<400> SEQUENCE: 87

Pro Lys Ser Asn Gln Ile Gly Gln Pro Thr Leu Pro Asn Asn Ser Leu
1               5                   10                  15

Ala Thr Pro Ser Pro Ser Leu Pro Ile Asn Pro Gly Thr Ser His Glu
            20                  25                  30

<210> SEQ ID NO 88
<211> LENGTH: 34
<212> TYPE: PRT
<213> ORGANISM: Streptococcus pyogenes

<400> SEQUENCE: 88

Pro Glu Val Thr Pro Thr Pro Glu Thr Pro Glu Gln Pro Gly Glu Lys
1               5                   10                  15

Ala Pro Glu Lys Ser Pro Glu Val Thr Pro Thr Pro Glu Thr Pro Glu
            20                  25                  30

Gln Pro

<210> SEQ ID NO 89
<211> LENGTH: 20
<212> TYPE: PRT
<213> ORGANISM: Streptococcus pyogenes

<400> SEQUENCE: 89

Pro Glu Val Thr Pro Thr Pro Glu Thr Pro Glu Gln Pro Gly Glu Lys
1               5                   10                  15

Ala Pro Glu Lys
            20

<210> SEQ ID NO 90
<211> LENGTH: 17
<212> TYPE: PRT
<213> ORGANISM: Streptococcus pyogenes

<400> SEQUENCE: 90

Pro Glu Lys Ser Pro Glu Val Thr Pro Thr Pro Glu Thr Pro Glu Gln
1               5                   10                  15

Pro

<210> SEQ ID NO 91
<211> LENGTH: 16
<212> TYPE: PRT
<213> ORGANISM: Streptococcus pyogenes

<400> SEQUENCE: 91

Lys Ala Pro Glu Lys Ser Pro Glu Val Thr Pro Thr Pro Glu Met Pro
1               5                   10                  15

<210> SEQ ID NO 92
<211> LENGTH: 25
<212> TYPE: PRT
<213> ORGANISM: Streptococcus pyogenes

<400> SEQUENCE: 92

Pro Gly Lys Pro Ala Pro Lys Thr Pro Glu Val Pro Gln Lys Pro Asp
1               5                   10                  15

Thr Ala Pro His Thr Pro Lys Thr Pro
            20                  25

<210> SEQ ID NO 93
<211> LENGTH: 18
<212> TYPE: PRT
<213> ORGANISM: Streptococcus equi

<400> SEQUENCE: 93

Lys Pro Ser Ala Pro Lys Ala Pro Glu Lys Ala Pro Ala Pro Lys Ala
1               5                   10                  15

Pro Lys

<210> SEQ ID NO 94
<211> LENGTH: 24
<212> TYPE: PRT
<213> ORGANISM: Streptococcus equi

<400> SEQUENCE: 94

Pro Ala Pro Lys Ala Pro Lys Ala Ser Glu Gln Ser Ser Asn Pro Lys
1               5                   10                  15

Ala Pro Ala Pro Lys Ser Ala Pro
            20

<210> SEQ ID NO 95
<211> LENGTH: 22
<212> TYPE: PRT
<213> ORGANISM: Streptococcus pyogenes

<400> SEQUENCE: 95

Pro Gly Pro Ala Gly Pro Arg Gly Leu Gln Gly Pro Gln Gly Pro Arg
1               5                   10                  15

Gly Asp Lys Gly Glu Thr
            20

<210> SEQ ID NO 96
<211> LENGTH: 17
<212> TYPE: PRT
<213> ORGANISM: Streptococcus suis

<400> SEQUENCE: 96

Pro Gln Ala Pro Ser Thr Pro Glu Lys Gln Pro Glu Val Pro Glu Ser
1               5                   10                  15

Pro

<210> SEQ ID NO 97
<211> LENGTH: 17
<212> TYPE: PRT
<213> ORGANISM: Streptococcus suis

<400> SEQUENCE: 97

Pro Glu Thr Pro Asp Ala Pro Ser Thr Pro Lys Asp Glu Pro Gln Ala
1               5                   10                  15

Pro

<210> SEQ ID NO 98
<211> LENGTH: 28
<212> TYPE: PRT
<213> ORGANISM: Streptococcus mutans

<400> SEQUENCE: 98

Pro Ala Pro Val Glu Pro Ser Tyr Glu Ala Glu Pro Thr Pro Pro Thr
1               5                   10                  15

Arg Thr Pro Asp Gln Ala Glu Pro Asn Lys Pro Thr
            20                  25

<210> SEQ ID NO 99
<211> LENGTH: 23
<212> TYPE: PRT
<213> ORGANISM: Streptococcus mutans

<400> SEQUENCE: 99

```
Pro Thr Tyr Glu Thr Glu Lys Pro Leu Glu Pro Ala Pro Val Glu Pro
1               5                   10                  15

Ser Tyr Glu Ala Glu Pro Thr
            20
```

<210> SEQ ID NO 100
<211> LENGTH: 30
<212> TYPE: PRT
<213> ORGANISM: Streptococcus mutans

<400> SEQUENCE: 100

```
Lys Pro Thr Ala Pro Thr Lys Pro Thr Tyr Glu Thr Glu Lys Pro Leu
1               5                   10                  15

Lys Pro Ala Pro Val Ala Pro Asn Tyr Glu Lys Glu Pro Thr
            20                  25                  30
```

<210> SEQ ID NO 101
<211> LENGTH: 18
<212> TYPE: PRT
<213> ORGANISM: Staphylococcus aureus

<400> SEQUENCE: 101

```
Lys Pro Val Val Pro Glu Gln Pro Asp Glu Pro Gly Glu Ile Glu Pro
1               5                   10                  15

Ile Pro
```

<210> SEQ ID NO 102
<211> LENGTH: 29
<212> TYPE: PRT
<213> ORGANISM: Staphylococcus aureus

<400> SEQUENCE: 102

```
Pro Glu Val Pro Ser Glu Pro Glu Thr Pro Thr Pro Thr Pro Glu
1               5                   10                  15

Val Pro Ala Glu Pro Gly Lys Pro Val Pro Pro Ala Lys
            20                  25
```

<210> SEQ ID NO 103
<211> LENGTH: 28
<212> TYPE: PRT
<213> ORGANISM: Staphylococcus aureus

<400> SEQUENCE: 103

```
Lys Tyr Thr Pro Lys Lys Pro Asn Lys Pro Ile Tyr Pro Glu Lys Pro
1               5                   10                  15

Lys Asp Lys Thr Pro Pro Thr Lys Pro Asp His Ser
            20                  25
```

<210> SEQ ID NO 104
<211> LENGTH: 12
<212> TYPE: PRT
<213> ORGANISM: Peptostreptococcus magnus

<400> SEQUENCE: 104

```
Pro Glu Lys Pro Val Glu Pro Ser Glu Pro Ser Thr
1               5                   10
```

<210> SEQ ID NO 105
<211> LENGTH: 44
<212> TYPE: PRT
<213> ORGANISM: Streptococcus dysgalactiae

<400> SEQUENCE: 105

```
Lys Pro Val Glu Pro Ser Glu Pro Thr Pro Asp Val Pro Ser Asn
1               5                   10                  15

Pro Ser Asn Pro Ser Thr Pro Asp Val Pro Ser Thr Pro Asp Val Pro
            20                  25                  30

Ser Asn Pro Ser Thr Pro Glu Val Pro Ser Asn Pro
        35                  40
```

<210> SEQ ID NO 106
<211> LENGTH: 17
<212> TYPE: PRT
<213> ORGANISM: Streptococcus dysgalactiae

<400> SEQUENCE: 106

```
Pro Gln Val Glu Pro Asn Val Pro Asp Thr Pro Gln Glu Lys Pro Leu
1               5                   10                  15

Thr
```

<210> SEQ ID NO 107
<211> LENGTH: 31
<212> TYPE: PRT
<213> ORGANISM: Streptococcus dysgalactiae

<400> SEQUENCE: 107

```
Lys Pro Leu Thr Pro Leu Ala Pro Ser Glu Pro Ser Gln Pro Ser Ile
1               5                   10                  15

Pro Glu Thr Pro Leu Ile Pro Ser Glu Pro Ser Val Pro Glu Thr
            20                  25                  30
```

<210> SEQ ID NO 108
<211> LENGTH: 18
<212> TYPE: PRT
<213> ORGANISM: Streptococcus agalactiae

<400> SEQUENCE: 108

```
Pro Glu Val Lys Pro Asp Val Lys Pro Glu Ala Lys Pro Glu Ala Lys
1               5                   10                  15

Pro Ala
```

<210> SEQ ID NO 109
<211> LENGTH: 11
<212> TYPE: PRT
<213> ORGANISM: Streptococcus agalactiae

<400> SEQUENCE: 109

```
Lys Pro Glu Ala Lys Pro Glu Ala Lys Pro Ala
1               5                   10
```

<210> SEQ ID NO 110
<211> LENGTH: 20
<212> TYPE: PRT
<213> ORGANISM: Streptococcus agalactiae

<400> SEQUENCE: 110

```
Pro Asp Val Lys Pro Glu Ala Lys Pro Glu Ala Lys Pro Asp Val Lys
1               5                   10                  15

Pro Glu Ala Lys
            20
```

<210> SEQ ID NO 111
<211> LENGTH: 14
<212> TYPE: PRT

-continued

<213> ORGANISM: Streptococcus agalactiae

<400> SEQUENCE: 111

Pro Glu Thr Pro Asp Thr Pro Lys Ile Pro Glu Leu Pro Gln
1               5                   10

<210> SEQ ID NO 112
<211> LENGTH: 20
<212> TYPE: PRT
<213> ORGANISM: Streptococcus agalactiae

<400> SEQUENCE: 112

Pro Asp Thr Pro Gln Ala Pro Asp Thr Pro His Val Pro Glu Ser Pro
1               5                   10                  15

Lys Thr Pro Glu
            20

<210> SEQ ID NO 113
<211> LENGTH: 29
<212> TYPE: PRT
<213> ORGANISM: Streptococcus pneumoniae

<400> SEQUENCE: 113

Gln Gln Ala Glu Glu Asp Tyr Ala Arg Arg Ser Glu Glu Glu Tyr Asn
1               5                   10                  15

Arg Leu Pro Gln Gln Gln Pro Pro Lys Ala Glu Lys Pro
            20                  25

<210> SEQ ID NO 114
<211> LENGTH: 31
<212> TYPE: PRT
<213> ORGANISM: Streptococcus pneumoniae

<400> SEQUENCE: 114

Ala Glu Asp Gln Lys Glu Glu Asp Arg Arg Asn Tyr Pro Thr Asn Thr
1               5                   10                  15

Tyr Lys Thr Leu Glu Leu Glu Ile Ala Glu Ser Asp Val Glu Val
            20                  25                  30

<210> SEQ ID NO 115
<211> LENGTH: 79
<212> TYPE: PRT
<213> ORGANISM: Streptococcus pneumoniae

<400> SEQUENCE: 115

Ser Val Ala Met Pro Ser Tyr Ile Gly Ser Ser Leu Glu Phe Thr Lys
1               5                   10                  15

Asn Asn Leu Ile Gln Ile Val Gly Ile Lys Glu Ala Asn Ile Glu Val
            20                  25                  30

Val Glu Val Thr Thr Ala Pro Ala Gly Ser Ala Glu Gly Met Val Val
        35                  40                  45

Glu Gln Ser Pro Arg Ala Gly Glu Lys Val Asp Leu Asn Lys Thr Arg
    50                  55                  60

Val Lys Ile Ser Ile Tyr Lys Pro Lys Thr Thr Ser Ala Thr Pro
65                  70                  75

<210> SEQ ID NO 116
<211> LENGTH: 60
<212> TYPE: PRT
<213> ORGANISM: Streptococcus pneumoniae

<400> SEQUENCE: 116

```
Ser Leu Phe Val Glu Ser Ser Val Asp Asp Arg Pro Met Lys Thr Val
1               5                  10                  15

Ser Gln Asp Thr Asn Ile Pro Ile Tyr Ala Gln Ile Phe Thr Asp Ser
            20                  25                  30

Ile Ala Glu Gln Gly Lys Glu Gly Asp Ser Tyr Tyr Ser Met Met Lys
        35                  40                  45

Tyr Asn Leu Asp Lys Ile Ala Glu Gly Leu Ala Lys
    50                  55                  60

<210> SEQ ID NO 117
<211> LENGTH: 112
<212> TYPE: PRT
<213> ORGANISM: Streptococcus pneumoniae

<400> SEQUENCE: 117

Asn Gly Asp Leu Leu Asp His Ser Gly Ala Tyr Val Ala Gln Tyr
1               5                  10                  15

Tyr Ile Thr Trp Asn Glu Leu Ser Tyr Asp His Gln Gly Lys Glu Val
            20                  25                  30

Leu Thr Pro Lys Ala Trp Asp Arg Asn Gly Gln Asp Leu Thr Ala His
        35                  40                  45

Phe Thr Thr Ser Ile Pro Leu Lys Gly Asn Val Arg Asn Leu Ser Val
    50                  55                  60

Lys Ile Arg Glu Cys Thr Gly Leu Ala Trp Glu Trp Trp Arg Thr Val
65                  70                  75                  80

Tyr Glu Lys Thr Asp Leu Pro Leu Val Arg Lys Arg Thr Ile Ser Ile
                85                  90                  95

Trp Gly Thr Thr Leu Tyr Pro Gln Val Glu Asp Lys Val Glu Asn Asp
            100                 105                 110

<210> SEQ ID NO 118
<211> LENGTH: 91
<212> TYPE: PRT
<213> ORGANISM: Streptococcus pneumoniae

<400> SEQUENCE: 118

Val Glu His Pro Asn Glu Arg Pro His Ser Asp Asn Gly Phe Gly Asn
1               5                  10                  15

Ala Ser Asp His Val Arg Lys Asn Lys Val Ala Gln Asp Ser Lys Pro
            20                  25                  30

Asp Glu Asp Lys Glu His Asp Glu Val Ser Glu Pro Thr His Pro Glu
        35                  40                  45

Ser Asp Glu Lys Glu Asn His Ala Gly Leu Asn Pro Ser Ala Asp Asn
    50                  55                  60

Leu Tyr Lys Pro Ser Thr Asp Thr Glu Glu Thr Glu Glu Glu Ala Glu
65                  70                  75                  80

Asp Thr Thr Asp Glu Ala Glu Ile Pro Gln Val
                85                  90

<210> SEQ ID NO 119
<211> LENGTH: 69
<212> TYPE: PRT
<213> ORGANISM: Streptococcus pneumoniae

<400> SEQUENCE: 119

Glu Asn Ser Val Ile Asn Ala Lys Ile Ala Asp Ala Glu Ala Leu Leu
1               5                  10                  15
```

-continued

```
Glu Lys Val Thr Asp Pro Ser Ile Arg Gln Asn Ala Met Glu Thr Leu
             20                  25                  30

Thr Gly Leu Lys Ser Ser Leu Leu Leu Gly Thr Lys Asp Asn Asn Thr
         35                  40                  45

Ile Ser Ala Glu Val Asp Ser Leu Leu Ala Leu Leu Lys Glu Ser Gln
     50                  55                  60

Pro Ala Pro Ile Gln
 65

<210> SEQ ID NO 120
<211> LENGTH: 28
<212> TYPE: DNA
<213> ORGANISM: Artificial
<220> FEATURE:
<223> OTHER INFORMATION: Synthetic construct

<400> SEQUENCE: 120
gcaagcttat gatatagaaa tttgtaac                                         28

<210> SEQ ID NO 121
<211> LENGTH: 27
<212> TYPE: DNA
<213> ORGANISM: Artificial
<220> FEATURE:
<223> OTHER INFORMATION: Synthetic construct

<400> SEQUENCE: 121
ccacataccg ttttcttgtt tccagcc                                          27

<210> SEQ ID NO 122
<211> LENGTH: 391
<212> TYPE: PRT
<213> ORGANISM: Streptococcus pneumoniae
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid

<400> SEQUENCE: 122
```

-continued

```
Xaa Xaa Leu Gly Ala Gly Phe Val Xaa Xaa Pro Thr Xaa Xaa Xaa
1               5                   10                  15

Xaa Xaa Glu Ala Pro Val Ala Ser Gln Xaa Lys Ala Glu Lys Asp Xaa
            20                  25                  30

Asp Ala Xaa Lys Arg Asp Ala Glu Asn Xaa Lys Lys Ala Leu Glu Glu
        35                  40                  45

Ala Lys Xaa Xaa Gln Lys Lys Tyr Glu Asp Asp Gln Lys Lys Thr Glu
50              55                  60

Glu Lys Xaa Lys Lys Glu Lys Glu Ala Ser Lys Glu Gln Ala Ala
65              70                  75                  80

Asn Leu Lys Tyr Gln Gln Glu Leu Val Lys Tyr Ala Ser Glu Lys Asp
                85                  90                  95

Ser Val Lys Lys Ala Lys Ile Leu Lys Glu Val Glu Glu Ala Glu Lys
                100                 105                 110

Glu His Lys Lys Lys Arg Ala Glu Phe Glu Lys Val Arg Ser Glu Val
            115                 120                 125

Ile Pro Ser Ala Glu Glu Leu Lys Lys Thr Arg Gln Lys Ala Glu Glu
        130                 135                 140

Ala Lys Ala Lys Glu Ala Glu Leu Ile Lys Lys Val Glu Glu Ala Glu
145                 150                 155                 160

Lys Lys Val Thr Glu Ala Lys Gln Lys Leu Asp Ala Glu Arg Ala Lys
                165                 170                 175

Glu Val Ala Leu Gln Ala Lys Ile Ala Glu Leu Glu Asn Glu Val Tyr
                180                 185                 190

Arg Leu Glu Thr Glu Leu Lys Gly Ile Asp Glu Ser Asp Ser Glu Asp
                195                 200                 205

Tyr Val Lys Glu Gly Leu Arg Ala Pro Leu Gln Ser Glu Leu Asp Ala
210                 215                 220

Lys Arg Thr Lys Leu Ser Thr Leu Glu Glu Leu Ser Asp Lys Ile Asp
225                 230                 235                 240

Glu Leu Asp Ala Glu Ile Ala Lys Leu Glu Lys Asn Val Glu Tyr Phe
                245                 250                 255

Lys Lys Thr Asp Ala Glu Gln Thr Glu Gln Tyr Leu Ala Ala Ala Glu
                260                 265                 270

Lys Asp Leu Ala Asp Lys Lys Ala Glu Leu Glu Lys Thr Glu Ala Asp
                275                 280                 285

Leu Lys Lys Ala Val Asn Glu Pro Glu Lys Pro Ala Glu Glu Thr Pro
290                 295                 300

Ala Pro Ala Pro Lys Pro Glu Gln Pro Ala Glu Gln Pro Lys Pro Ala
305                 310                 315                 320

Pro Ala Pro Gln Pro Ala Pro Ala Pro Lys Pro Glu Lys Thr Asp Asp
                325                 330                 335

Gln Gln Ala Glu Glu Asp Tyr Ala Arg Arg Ser Glu Glu Tyr Asn
                340                 345                 350

Arg Leu Pro Gln Gln Gln Pro Pro Lys Ala Glu Lys Pro Ala Pro Ala
                355                 360                 365

Pro Lys Pro Glu Gln Pro Val Pro Ala Pro Lys Thr Gly Trp Lys Gln
                370                 375                 380

Glu Asn Gly Met Trp Cys Arg
385                 390

<210> SEQ ID NO 123
<211> LENGTH: 723
```

<212> TYPE: PRT
<213> ORGANISM: Streptococcus pneumoniae

<400> SEQUENCE: 123

```
Met Asn Lys Lys Lys Met Ile Leu Thr Ser Leu Ala Ser Val Ala Ile
1               5                   10                  15

Leu Gly Ala Gly Phe Val Thr Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Val Lys Lys Ser Glu Ala Lys Lys His Tyr Glu Glu Ala Lys
    50                  55                  60

Lys Lys Ala Glu Asp Ala Gln Lys Lys Tyr Asp Glu Asp Gln Lys Lys
65                  70                  75                  80

Thr Glu Ala Lys Ala Glu Lys Glu Arg Lys Ala Ser Glu Lys Ile Ala
                85                  90                  95

Glu Ala Thr Lys Glu Val Gln Gln Ala Tyr Leu Ala Tyr Leu Gln Ala
            100                 105                 110

Ser Asn Glu Ser Gln Arg Lys Glu Ala Asp Lys Lys Ile Lys Glu Ala
        115                 120                 125

Thr Gln Arg Lys Asp Glu Ala Glu Ala Ala Phe Ala Thr Ile Arg Thr
    130                 135                 140

Thr Ile Val Val Pro Glu Pro Ser Glu Leu Ala Glu Thr Lys Lys Lys
145                 150                 155                 160

Ala Glu Glu Ala Lys Ala Glu Glu Lys Val Ala Lys Arg Lys Tyr Asp
                165                 170                 175

Tyr Ala Thr Leu Lys Leu Ala Leu Ala Lys Lys Glu Val Glu Ala Lys
            180                 185                 190

Glu Leu Glu Ile Glu Lys Leu Gln Tyr Glu Ile Ser Thr Leu Glu Gln
        195                 200                 205

Glu Val Ala Thr Ala Gln His Gln Val Asp Asn Leu Lys Lys Leu Leu
    210                 215                 220

Ala Gly Ala Asp Pro Asp Asp Gly Thr Glu Val Ile Glu Ala Lys Leu
225                 230                 235                 240

Lys Lys Gly Glu Ala Glu Leu Asn Ala Lys Gln Ala Glu Leu Ala Lys
                245                 250                 255

Lys Gln Thr Glu Leu Glu Lys Leu Leu Asp Ser Leu Asp Pro Glu Gly
            260                 265                 270

Lys Thr Gln Asp Glu Leu Asp Lys Glu Ala Glu Glu Ala Glu Leu Asp
        275                 280                 285

Lys Lys Ala Asp Glu Leu Gln Asn Lys Val Ala Asp Leu Glu Lys Glu
    290                 295                 300

Ile Ser Asn Leu Glu Ile Leu Leu Gly Gly Ala Asp Pro Glu Asp Asp
305                 310                 315                 320

Thr Ala Ala Leu Gln Asn Lys Leu Ala Ala Lys Lys Ala Glu Leu Ala
                325                 330                 335

Lys Lys Gln Thr Glu Leu Glu Lys Leu Leu Asp Ser Leu Asp Pro Glu
            340                 345                 350

Gly Lys Thr Gln Asp Glu Leu Asp Lys Glu Ala Glu Glu Ala Glu Leu
        355                 360                 365

Asp Lys Lys Ala Asp Glu Leu Gln Asn Lys Val Ala Asp Leu Glu Lys
    370                 375                 380

Glu Ile Ser Asn Leu Glu Ile Leu Leu Gly Gly Ala Asp Ser Glu Asp
385                 390                 395                 400
```

-continued

Asp Thr Ala Ala Leu Gln Asn Lys Leu Ala Thr Lys Ala Glu Leu
              405                 410                 415

Glu Lys Thr Gln Lys Glu Leu Asp Ala Ala Leu Asn Glu Leu Gly Pro
         420                 425                 430

Asp Gly Asp Glu Glu Thr Pro Ala Pro Ala Pro Gln Pro Glu Gln
         435                 440                 445

Pro Ala Pro Ala Pro Lys Pro Glu Gln Pro Ala Pro Ala Pro Lys Pro
450                 455                 460

Glu Gln Pro Ala Pro Ala Pro Lys Pro Glu Gln Pro Ala Pro Ala Pro
465                 470                 475                 480

Lys Pro Glu Gln Pro Ala Lys Pro Glu Lys Pro Ala Glu Glu Pro Thr
              485                 490                 495

Gln Pro Glu Lys Pro Ala Thr Pro Lys Thr Gly Trp Lys Gln Glu Asn
         500                 505                 510

Gly Met Trp Tyr Phe Tyr Asn Thr Asp Gly Ser Met Ala Thr Gly Trp
         515                 520                 525

Leu Gln Asn Asn Gly Ser Trp Tyr Tyr Leu Asn Ala Asn Gly Ser Met
         530                 535                 540

Ala Thr Gly Trp Val Lys Asp Gly Asp Thr Trp Tyr Tyr Leu Glu Ala
545                 550                 555                 560

Ser Gly Ala Met Lys Ala Ser Gln Trp Phe Lys Val Ser Asp Lys Trp
              565                 570                 575

Tyr Tyr Val Asn Ser Asn Gly Ala Met Ala Thr Gly Trp Leu Gln Tyr
         580                 585                 590

Asn Gly Ser Trp Tyr Tyr Leu Asn Ala Asn Gly Asp Met Ala Thr Gly
         595                 600                 605

Trp Leu Gln Tyr Asn Gly Ser Trp Tyr Tyr Leu Asn Ala Asn Gly Asp
610                 615                 620

Met Ala Thr Gly Trp Ala Lys Val Asn Gly Ser Trp Tyr Tyr Leu Asn
625                 630                 635                 640

Ala Asn Gly Ala Met Ala Thr Gly Trp Ala Lys Val Asn Gly Ser Trp
              645                 650                 655

Tyr Tyr Leu Asn Ala Asn Gly Ser Met Ala Thr Gly Trp Val Lys Asp
         660                 665                 670

Gly Asp Thr Trp Tyr Tyr Leu Glu Ala Ser Gly Ala Met Lys Ala Ser
         675                 680                 685

Gln Trp Phe Lys Val Ser Asp Lys Trp Tyr Tyr Val Asn Gly Leu Gly
         690                 695                 700

Ala Leu Ala Val Asn Thr Thr Val Asp Gly Tyr Lys Val Asn Ala Asn
705                 710                 715                 720

Gly Glu Trp

<210> SEQ ID NO 124
<211> LENGTH: 11
<212> TYPE: PRT
<213> ORGANISM: Streptococcus pneumoniae

<400> SEQUENCE: 124

Pro Ala Pro Lys Pro Glu Gln Pro Ala Glu Gln
1               5                   10

<210> SEQ ID NO 125
<211> LENGTH: 7
<212> TYPE: PRT
<213> ORGANISM: Artificial

<220> FEATURE:
<223> OTHER INFORMATION: Synthetic construct

<400> SEQUENCE: 125

Ile Glu Lys Lys Ile Glu Gly
1               5

<210> SEQ ID NO 126
<211> LENGTH: 13
<212> TYPE: PRT
<213> ORGANISM: Artificial
<220> FEATURE:
<223> OTHER INFORMATION: Synthetic construct

<400> SEQUENCE: 126

Lys Tyr Val Lys Gln Asn Thr Leu Lys Leu Ala Arg Lys
1               5                   10

<210> SEQ ID NO 127
<211> LENGTH: 51
<212> TYPE: PRT
<213> ORGANISM: Artificial
<220> FEATURE:
<223> OTHER INFORMATION: Synthetic construct

<400> SEQUENCE: 127

Gly Gly Ile Glu Lys Lys Ile Glu Gly Ile Glu Lys Lys Ile Glu Gly
1               5                   10                  15

Ile Glu Lys Lys Ile Glu Gly Ile Glu Lys Lys Ile Glu Gly Ile Glu
                20                  25                  30

Lys Lys Ile Ala Lys Met Glu Lys Ala Ser Ser Val Phe Asn Val Val
            35                  40                  45

Asn Ser Lys
    50

<210> SEQ ID NO 128
<211> LENGTH: 67
<212> TYPE: PRT
<213> ORGANISM: Artificial
<220> FEATURE:
<223> OTHER INFORMATION: Synthetic sequence

<400> SEQUENCE: 128

Gly Gly Ile Glu Lys Lys Ile Glu Gly Ile Glu Lys Lys Ile Glu Gly
1               5                   10                  15

Ile Glu Lys Lys Ile Glu Gly Ile Glu Lys Lys Ile Glu Gly Ile Glu
                20                  25                  30

Lys Lys Ile Ala Lys Met Glu Lys Ala Ser Ser Val Phe Asn Val Val
            35                  40                  45

Asn Ser Lys Pro Ala Pro Ala Pro Lys Pro Glu Gln Pro Ala Glu Gln
    50                  55                  60

Pro Lys Pro
65

<210> SEQ ID NO 129
<211> LENGTH: 48
<212> TYPE: PRT
<213> ORGANISM: Artificial
<220> FEATURE:
<223> OTHER INFORMATION: Synthetic construct

<400> SEQUENCE: 129

Gly Gly Ile Glu Lys Lys Ile Glu Gly Ile Glu Lys Lys Ile Glu Gly

```
              1               5                  10                 15
Ile Glu Lys Lys Ile Glu Gly Ile Glu Lys Lys Ile Glu Gly Ile Glu
                 20                 25                 30

Lys Lys Ile Ala Lys Tyr Val Lys Gln Asn Thr Leu Lys Leu Ala Arg
         35                 40                 45
```

<210> SEQ ID NO 130
<211> LENGTH: 67
<212> TYPE: PRT
<213> ORGANISM: Artificial
<220> FEATURE:
<223> OTHER INFORMATION: Synthetic construct

<400> SEQUENCE: 130

```
Gly Gly Ile Glu Lys Lys Ile Glu Gly Ile Glu Lys Lys Ile Glu Gly
1               5                  10                 15

Ile Glu Lys Lys Ile Glu Gly Ile Glu Lys Lys Ile Glu Gly Ile Glu
                20                 25                 30

Lys Lys Ile Ala Lys Met Glu Lys Ala Ser Ser Val Phe Asn Val Val
         35                 40                 45

Asn Ser Lys Pro Ala Pro Ala Pro Lys Pro Glu Gln Pro Ala Glu Gln
     50                 55                 60

Pro Lys Pro
65
```

<210> SEQ ID NO 131
<211> LENGTH: 79
<212> TYPE: PRT
<213> ORGANISM: Artificial
<220> FEATURE:
<223> OTHER INFORMATION: Synthetic construct

<400> SEQUENCE: 131

```
Ser Val Ala Met Pro Ser Tyr Ile Gly Ser Ser Leu Glu Gln Thr Lys
1               5                  10                 15

Asn Asn Leu Ile Gln Thr Val Gly Ile Lys Glu Ala Asn Ile Glu Val
                20                 25                 30

Val Glu Val Thr Thr Ala Pro Ala Gly Ser Ala Glu Gly Met Val Val
         35                 40                 45

Glu Gln Ser Pro Arg Ala Gly Glu Lys Val Asp Leu Asn Lys Thr Arg
     50                 55                 60

Val Lys Ile Ser Ile Tyr Lys Pro Lys Thr Thr Ser Ala Thr Pro
65              70                 75
```

<210> SEQ ID NO 132
<211> LENGTH: 31
<212> TYPE: PRT
<213> ORGANISM: Artificial
<220> FEATURE:
<223> OTHER INFORMATION: Synthetic construct

<400> SEQUENCE: 132

```
Ala Glu Asp Gln Lys Glu Glu Asp Arg Arg Asn Tyr Pro Thr Asn Thr
1               5                  10                 15

Tyr Lys Thr Ala Glu Leu Glu Lys Ala Glu Ser Asp Val Glu Val
                20                 25                 30
```

<210> SEQ ID NO 133
<211> LENGTH: 268
<212> TYPE: PRT
<213> ORGANISM: Streptococcus pneumoniae -continued

```
<400> SEQUENCE: 133

Met Ser Asp Lys Ile Ile His Leu Thr Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
            115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Asp Leu Lys Lys Ala Val Asn Glu Pro Glu Lys Pro Ala Glu Glu
            165                 170                 175

Thr Pro Ala Pro Ala Pro Lys Pro Glu Gln Pro Ala Glu Gln Pro Lys
            180                 185                 190

Pro Ala Pro Ala Pro Gln Pro Ala Pro Ala Pro Lys Pro Glu Lys Thr
        195                 200                 205

Asp Asp Gln Gln Ala Glu Glu Asp Tyr Ala Arg Arg Ser Glu Glu Glu
        210                 215                 220

Tyr Asn Arg Leu Pro Gln Gln Gln Pro Pro Lys Ala Glu Lys Pro Ala
225                 230                 235                 240

Pro Ala Pro Lys Pro Glu Gln Pro Val Pro Ala Pro Lys Pro Glu Gln
            245                 250                 255

Pro Val Pro Ala Pro Lys Thr Gly Trp Lys Gln Glu
            260                 265
```

PROLINE-RICH PEPTIDES PROTECTIVE AGAINST *S. PNEUMONIAE*

FIELD OF THE INVENTION

The invention relates to multimeric lipopeptides consisting of a peptide chain comprising a parallel coiled-coil domain, a proline-rich peptide antigen, and a lipid moiety, all covalently linked, which aggregate to synthetic virus-like particles. These synthetic virus-like particles carrying proline-rich antigens are useful as vaccines against infectious diseases caused by Gram-positive bacteria such as *Streptococcus pneumoniae*.

BACKGROUND OF THE INVENTION

Gram-positive bacteria, including *Streptococci* or *Staphylococci* are important pathogens and the etiological agent of a number of serious diseases including pneumonia, sepsis, meningitis, wound infections, endocarditis, acute rheumatic fever, neonatal sepsis or toxic shock syndrome. Therefore there is a need to develop vaccines against these pathogens. Vaccines are already available for some *S. pneumoniae* serotypes; these have shortcomings such as a highly complex manufacturing process.

*S. pneumoniae* is a highly diverse polysaccharide encapsulated alpha-hemolytic *Streptococcus* that frequently colonizes the human nasopharynx and can cause non-invasive pneumococcal diseases such as otitis media, sinusitis and non-bacteraemic pneumonia, and more severe invasive diseases such as bacteraemia/sepsis, meningitis and bacteraemic pneumonia, primarily among young children and the elderly.

The polysaccharide capsule is a major determinant of virulence during invasion and prevents C3b opsonisation and non-opsonic killing by neutrophils. Currently licensed vaccines contain capsular polysaccharide antigens formulated either alone in pneumococcal polysaccharide vaccines (PPSV) or conjugated to a carrier protein such as modified diphtheria toxin CRM 197 in pneumococcal conjugate vaccines (PCV). There are more than 90 different capsular serotypes in 40 serogroups.

Polysaccharide pneumococcal vaccines can provide serotype-specific protection but cross-protection is low even within the same serogroup. Serotype replacement has been observed after introduction of the conjugate vaccine Prevnar® 7 in the U.S. in 2000. Among the emerging serotypes are also multi-drug resistant capsule-switch variants. Therefore there is a need for next generation pneumococcal vaccines that target other antigens than the capsule.

One potential antigen for inclusion into a next generation pneumococcal vaccine is Pneumococcal Surface Protein A (PspA). PspA is a monomeric polymorphic cholin-binding protein and contains an N-terminal alpha-helical part, which forms an antiparallel coiled-coil with itself, a proline-rich region, which is sometimes interspersed by a relatively conserved non-proline block, and a C-terminal region containing multiple repeats of a choline binding domain.

The N-terminal region of PspA contains immunodominant epitopes. Recombinant proteins comprising this region and bacterial vectors expressing this region have shown protective potential in various models. For example, Langermann et al. have prepared recombinant Bacille Calmette-Guérin (rBCG) vectors expressing PspA. In order to be able to anchor the PspA in the bacterial membrane, a PspA-derived gene segment was fused to Mtb19 lipoprotein (see Langermann S. et al., *J. Exp. Med.* 1994, 180, 2277-2286).

There is a safety concern associated with the use of PspA as a vaccine antigen because the N-terminal region may resemble human myosin and thus immunization with an immunogen encompassing this region may lead to tissue cross-reactive antibodies. Therefore recent efforts have been made to use other regions of PspA as antigen. Another PspA region that may be suitable for inclusion into a next generation pneumococcal vaccine is the proline-rich region. Although the proline-rich region (PRR) of PspA is polymorphic, it contains several conserved motifs, including short amino acid motifs like PKP, PAPAP, PEKP, and a highly conserved non-proline block (NPB) that is present in some PspA molecules (Brooks-Walter, A. et al., *Infect Immun* 1999, 67, 6533-6542; Hollingshead, S. K. et al., *Infect Immun*, 2000, 68, 5889-5900; Daniels, C. C. et al., *Infect Immun*, 2010, 78, 2163-2172.). Although the PRR does not contain immunodominant epitopes, antibodies against this part of PspA have been detected in children using an enzyme immunoassay (EIA) with a thioredoxin (Trx) fusion protein as antigen (Melin, M. et al., *Vaccine* 2012, 30, 7157-7160). Because the NPB is highly conserved the authors hypothesize that antibodies to the PRR may cross-react with a majority of strains through their recognition of NPB epitopes.

The PRR of PspA has a small size (up to around 100 amino acids) and therefore may not be sufficiently immunogenic when used as an antigen alone. *Escherichia coli* Trx fusion proteins have been produced and their potential for protection has been demonstrated in a mouse model of intravenous infection (WO 2007/089866 and Daniels, C. C. et al., *Infect Immun*, 2010, 78, 2163-2172). However, Trx fusion proteins may not be suitable for human use as a vaccine because of a potential for the induction of immune responses to non-protective Trx epitopes and poor structural representation of native PR epitopes.

Moreover NPB or proline-rich (PR) sequences may also contain non-protective epitopes, and hence it may be critical to concentrate immune responses to protective epitopes for efficacy.

Similar PR sequences can be found in other pneumococcal proteins, including the surface proteins PspC (also known as CbpA or Hic), and the PhtX proteins PhtA, PhtB, PhtD and PhtE, and proline-rich regions derived from such other pneumococcal proteins may be suitable for inclusion into a next generation pneumococcal vaccine, like proline-rich sequences from PspA.

Several immunogenic bacterial surface proteins from other Gram-positive bacteria contain proline-rich sequences that can likewise be targeted by vaccines against these pathogens. These proteins include surface proteins from other *Streptococci* such as the M6, SclA and SclB proteins of *S. pyogenes*, CBeta (bac) and BibA of *S. agalactiae* or the P1 adhesin of *S. mutans*, or proteins from *S. aureus*.

Synthetic bacterial lipopeptide analogs have received wide attention in vaccine research, both for their adjuvant effects and as carriers for peptide antigens (Ghielmetti M. et al., *Immunobiology* 2005, 210, 211-215). Many lipopeptide constructs have been reported, in which a lipid with known adjuvant effects has been coupled to a peptide to generate self-adjuvanting vaccine candidates. Particularly well studied are tripalmitoyl-S-glyceryl cysteine (N-palmitoyl-S-(2,3-bis-(O-palmitoyloxy)-propyl)-cysteinyl- or Pam3Cys) and dipalmitoyl-S-glyceryl cysteine (2,3-bis-(O-palmitoyloxy)-propyl)-cysteinyl- or Pam2Cys). These lipid moieties are found in lipoprotein components of the inner and outer membranes of gram-negative bacteria. Patent application WO 98/07752 describes the use of lipopeptides for drug targeting purposes, wherein the peptide portion may be a collagen-like sequence capable of inducing triple helical structures. Patent application WO 2008/068017 describes synthetic virus-like particles comprising helical lipopeptide bundles and having a spherical or spheroidal structure with a lipid core and a peptidic outer surface. The peptide chain of the lipopeptides comprises a coiled-coil domain. The properties of the coiled-coil domain in the peptide chain of the lipopeptide building blocks determine the number of building blocks combining to form the synthetic virus-like particle.

SUMMARY OF THE INVENTION

The invention relates to lipopeptide building blocks consisting of (1) a peptide chain comprising a parallel coiled-coil domain which, as a self-standing lipid-free peptide, forms a parallel dimeric, trimeric or higher order oligomeric helical bundle, (2) a proline-rich (PR) peptide antigen comprising at least one negatively and at least one positively charged amino acid, and wherein at least 15% of the amino acids are proline, optionally linked to a further antigen, and (3) a lipid moiety comprising two or three long hydrocarbyl chains; wherein the peptide chain, the PR peptide antigen and the lipid moiety are covalently linked, either directly or through a linker. Preferably, the peptide chain comprising a parallel coiled coil is linked at one end to the PR peptide antigen and at the other end to the lipid moiety.

These lipopeptide building blocks aggregate to helical lipopeptide bundles and synthetic virus-like particles (SVLP). The presentation of the PR antigen on the SVLP surface enhances the immune response to PR epitopes.

Preferred are lipopeptide building blocks comprising PR peptide antigens derived from *Streptococci* and/or *Staphylococci*, more preferably from *Streptococcus pneumoniae*.

The invention further relates to processes of production of lipopeptide building blocks, helical lipopeptide bundles and synthetic virus-like particles; to the use of lipopeptide building blocks, helical lipopeptide bundles and synthetic virus-like particles carrying PR peptide antigens in the preparation of vaccines; and to methods of vaccination using such vaccines. The invention likewise relates to pharmaceutical preparations containing synthetic virus-like particles carrying PR antigens.

The compositions of the invention comprising PR peptide antigens derived from *Streptococci* and/or *Staphylococci*, in particular from *S. pneumoniae*, are useful for inducing immune responses against *S. pneumoniae* or other Gram-positive bacteria, and for the prevention or treatment of infectious diseases such as pneumococcal diseases caused by *S. pneumoniae*.

DETAILED DESCRIPTION OF THE INVENTION

Figure 1:
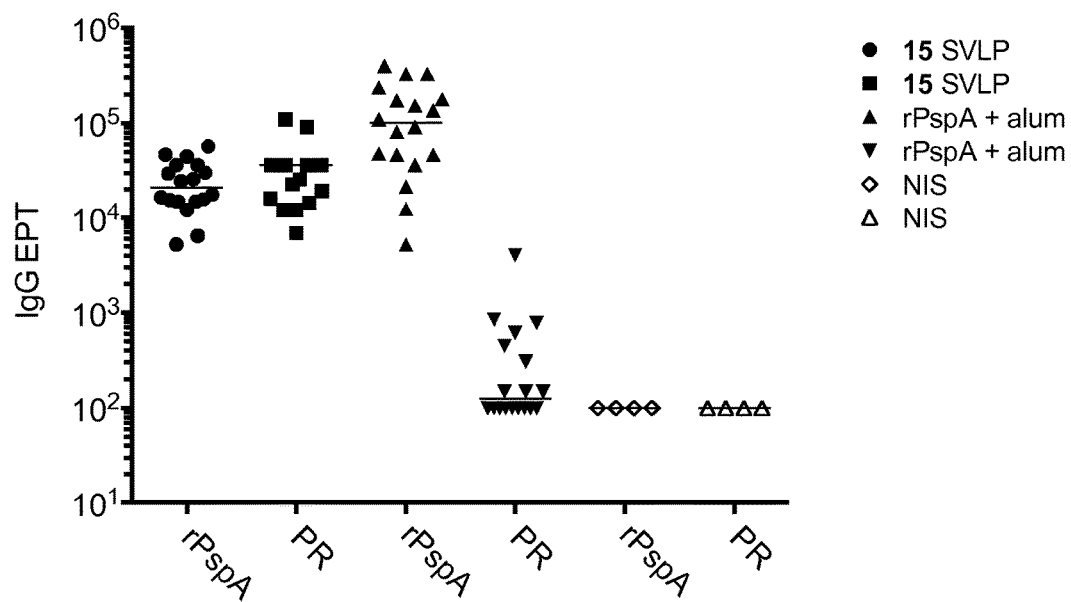
FIG. 1: IgG ELISA endpoint titers in sera from BALB/c mice immunized two times with lipopeptide 15 (closed circles and squares) or alum adjuvanted recombinant PspA (rPspA, closed triangles) and sera from non-immunized controls (open symbols). Symbols indicate endpoint titers sera from individual mice, lines indicate median values. Titers were measured against a peptide representing the proline-rich region (PR peptide) and recombinant PspA protein comprising the entire N-terminal alpha-helical part, the proline-rich region and the non-proline block (rPspA).

The invention relates to lipopeptide building blocks consisting of
(1) a peptide chain (PC) comprising a parallel coiled-coil domain which, as a self-standing lipid-free peptide, forms a parallel dimeric, trimeric or higher order oligomeric helical bundle,
(2) a proline-rich (PR) peptide antigen, comprising at least one negatively and at least one positively charged amino acid, and wherein at least 15% of the amino acids are proline, optionally linked to a further antigen, and
(3) a lipid moiety (LM) comprising three or preferably two long hydrocarbyl chains, wherein the peptide chain, the PR peptide antigen and the lipid moiety are covalently linked, either directly or through a linker, in particular two different linkers.

Preferably, the peptide chain comprising a parallel coiled coil is linked at one end to the PR peptide antigen and at the other end to the lipid moiety.

The peptide chain (PC) comprises a parallel coiled-coil domain. Such coiled-coil domains will associate into a defined helical bundle, e.g. into a dimeric, trimeric, tetrameric, pentameric, hexameric or heptameric bundle. Parallel coiled-coil domains differ from antiparallel coiled-coils, wherein a monomeric peptide chain loops back to form a helical substructure by aligning two (or more) partial domains of the monomeric peptide in an antiparallel alignment. The parallel coiled-coil domain may contain between 12 and 120 amino acid residues, preferably between 21 and 80 amino acid residues. Coiled-coil domains contain two or more consecutive repeat patterns (usually heptad repeats in which the seven structural positions are labeled a-g, with a and d denoting hydrophobic residues), which as self-standing lipid-free peptides possess the property of self-assembly into a parallel coiled-coil helical bundle (Lupas A. N., Gruber M.; The structure of alpha-helical coiled coils, *Adv. Protein Chem.* 2005, 70, 37-78). The peptide chain must multimerize to form a parallel coiled-coil helical bundle of defined oligomerization state (e.g. dimer, trimer, tetramer, pentamer, hexamer or heptamer, in particular dimer, trimer, tetramer or pentamer). Preferred peptide sequences are non-human sequences to avoid the risk of autoimmune disorders when applied in the vaccination of humans.

The lipopeptide building block further comprises a proline-rich (PR) peptide antigen comprising at least one negatively and at least one positively charged amino acid. Charged amino acids considered herein are amino acids with side chains that are positively or negatively charged at physiological pH. Among the naturally occurring amino acids the most frequent positively charged amino acids considered here are lysine, arginine and histidine; the most frequent negatively charged amino acids are glutamic acid and aspartic acid. A peptide is considered "proline-rich" if at least 15% of the amino acids are proline. Preferred are proline-rich peptides comprising at least one glutamic acid residue and at least one lysine or arginine residue.

Preferred PR peptide antigens are derived from *Streptococci* and/or *Staphylococci*, e.g. from Gram-positive bacteria selected from the group consisting of *Streptococcus pyogenes, Streptococcus agalactiae, Streptococcus mutans,*

Streptococcus suis, Streptococcus equi, Streptococcus dysgalactiae, Peptostreptococcus magnus and Staphylococcus aureus.

Preferably this PR peptide antigen is derived from proteins PspA and/or PspC or other proteins that are protective against pneumococcal infection, including PhtX proteins.

"Derived" means that the amino acid sequence or a substantial portion (i.e. 50% or more) of the amino acid sequence of the peptide antigen originates from one or more naturally occurring protein(s), whereas 0% up to 50% of the amino acid sequence is designed de novo. Included are also PR peptide antigens that comprise combinations of proline-rich sequences from different PspA/PspC molecules and/or from other proteins containing proline-rich segments. "Proline-rich segment" means that at least 15% of the amino acids contained in the segment are proline.

Proline-rich (PR) peptide antigens of particular interest are derived from *S. pneumoniae* and are located immediately after the C-terminal end of the helical region of PspA or PspC and before the non-proline block (if the PspA or PspC sequence comprises a non-proline block) or the repeat region. Alternatively the PR peptide antigen is located in the central region of a pneumococcal polyhistidine triad protein (PhtX). Alternatively the PR peptide antigen is located in a region of PR proteins of Gram-positive bacteria selected from the group consisting of *Streptococcus pyogenes, Streptococcus agalactiae, Streptococcus mutans, Streptococcus suis, Streptococcus equi, Streptococcus dysgalactiae, Peptostreptococcus magnus* and *Staphylococcus aureus*, such as the central region of the P1 adhesin of *Streptococcus mutans*.

Protective PR peptide antigens are identified by sequencing PspA and/or PspC and/or other genes from clinical isolates, selecting a portion of the PR region, synthesizing the PR peptide, and conjugating it to a peptide chain (PC) to be incorporated or being part of a lipopeptide.

The efficacy of PR peptide antigens is tested by administering lipopeptide conjugates and synthetic virus-like particles obtained therefrom and observing the activity and efficacy in animal models of pneumococcal sepsis or other diseases caused by streptococcal infection.

The PR peptide antigen is optionally linked to a further antigen. Further antigens considered are other pneumococcal peptides or polysaccharides, in particular the peptides with an amino acid sequence SEQ ID NO: 113 to 119, and other antigens described below.

The PR peptide antigen is conjugated directly or through a linker, either at the N- or C-terminus of the PR peptide antigen, and is connected either to the N- or to the C-terminal of the peptide chain (PC) comprising the coiled coil domain, or optionally to an amino acid side chain. Alternatively the PR peptide antigen is conjugated to the peptide chain (PC) comprising the coiled coil domain through a side chain residue of the PR peptide antigen, such as a terminal or internal aspartic acid, glutamic acid, lysine, ornithine or cysteine side chain. Linkers considered are short peptides of 2 to 20 amino acids, hydroxyalkyl- or aminoalkyl-carboxylic acids, substituted or unsubstituted polyalkylenoxy glycols, preferably containing one to twelve $C_2$ and/or $C_3$ alkylenoxy units, polyalkylenoxy glycol block co-polymers (e.g. pluronics), mono-, di-, tri- and oligosaccharides, which may comprise acetyl, glycerol-phosphate or other substituents at one or more positions, polysaccharides such as poly(sialylic acid) and derivatives (e.g. peptide conjugates) thereof, proteinogenic or non-proteinogenic amino acids, and $C_1$-$C_8$ saturated or unsaturated hydrocarbons, and may comprise one or more of the following functional groups: a disulphide bond, amine, amide, acetal, ester, ether, thioether, hydrazone, hydrazide, imine, oxime, urea, thiourea, carbonate, iminocarbonate, amidine, amide, imide, an alkyl succinimide, which may also be hydrolyzed to an amide, sulphonamide, sulfone, or a heterocyclic ring comprising one or more atoms selected from nitrogen and oxygen, preferably a triazole. Also considered are combinations of the aforementioned linkers, including those used in the Examples.

Any method used for conjugating peptides or other antigens to an antigen delivery system such as carrier protein, polymer, dendrimer, nanoparticle or virus-like particle, can be used to conjugate the PR peptide antigens to the peptide chain (PC) comprising the parallel coiled-coil domain. Such methods are well-known to those skilled in the art, see for example Hermanson, G.T, Bioconjugate Techniques, $2^{nd}$ edition, Academic Press, 2008.

PR peptide antigens consist of 5-200 amino acids, preferably 8-80 amino acids. Multiple PR peptide conjugates can be used in combination in a vaccine formulation. PR peptide antigens can also be fused together in order to produce a longer artificial PR peptide. PR conjugates can also be combined with conjugates comprising other pneumococcal peptides or polysaccharides. Amino acids and derivatives thereof comprising a functional group (e.g. an amino-, halo-, hydrazino-, hydroxylamino- or sulfhydryl group) can be incorporated into the PR peptide in order to facilitate conjugation of the PR peptide and enhance stability.

The peptide chain (PC) may further comprise an amino acid sequence which includes one or more T-helper cell epitopes, and/or strings of polar residues that promote the solubility of the lipopeptide building block in water.

T-helper epitopes that may be incorporated into the peptide chain (PC) include those listed in Table 1 below, and variants thereof in which one, two, or three amino acids are replaced by other amino acids or are deleted.

TABLE 1

| T-helper epitope | SEQ ID NO: | Sequence [a] |
|---|---|---|
| TT830-843 | 1 | QYIKANSKFIGITE |
| TT1064-1079 | 2 | IREDNNITLKLDRCNN |
| TT1084-1099 | 3 | VSIDKFRIFCKANPK |
| TT947-968 | 4 | FNNFTVSFWLRVPKVSASHLET |
| TT1174-1189 | 5 | LKFIIKRYTPNNEIDS |
| DTD271-290 | 6 | PVFAGANYAAWAVNVAQVID |
| DTD321-340 | 7 | VHHNTEEIVAQSIALSSLMV |
| DTD331-350 | 8 | QSIALSSLMVAQAIPLVGEL |
| DTD351-370 | 9 | VDIGFAAYNFVESIINLFQV |
| DTD411-430 | 10 | QGESGHDIKITAENTPLPIA |
| DTD431-450 | 11 | GVLLPTIPGKLDVNKSKTHI |
| TT632-651 | 12 | TIDKISDVSTIVPYIGPALN |
| CTMOMP36-60 | 13 | ALNIWDRFDVFCTLGATTGYLKGNS |
| TraT1 | 14 | GLQGKIADAVKAKG |
| TraT2 | 15 | GLAAGLVGMAADAMVEDVN |
| TraT3 | 16 | STETGNQHHYQTRVVSNANK |

TABLE 1 -continued

| T-helper epitope | SEQ ID NO: | Sequence [a] |
|---|---|---|
| HbcAg50-69 | 17 | PHHTALRQAILCWGELMTLA |
| HbSAg19-33 | 18 | FFLLTRILTIPQSLD |
| HA307-319 | 19 | PKYVKQNTLKLAT |
| MA17-31 | 20 | YSGPLKAEIAQRLEDV |
| MVF258-277 | 21 | GILESRGIKARITHVDTESY |
| MVF288-302 | 22 | LSEIKGVIVHRLEGV |
| CS.T3* | 23 | IEKKIAKMEKASSVFNWNS |
| SM Th | 24 | KWFKTNAPNGVDEKIRI |
| PADRE1 [b] | 25 | aKFVAAWTLKAAa |
| PADRE2 [b] | 26 | aK-Chx-VAAWTLKAAa |

[a] References: SEQ ID NO: 1-5 and 17-20: Eur. J. Immunol. 2001, 31, 3816-3824; SEQ ID NO: 6-12: JID 2000, 181, 1001-1009; SEQ ID NO: 13-16, 21-22 and 24: U.S. 5,759,551; SEQ ID NO: 23: Nature 1988, 336, 778-780; SEQ ID NO: 25-26: Immunity 1994, 1, 751-761.
[b] "a" denotes D-Ala and "Chx" denotes cyclohexylalanine.

The total length of the peptide chain (PC) is preferably between 21 and 200 amino acid residues, more preferably between 21 and 120 amino acid residues.

The lipid moiety (LM) contains a lipid anchor with two or three, preferably two, long hydrocarbyl chains and a structure combining these hydrocarbyl chains and connect it to the peptide chain (PC), either directly or via a linker. The lipid moiety can also be connected to the PR peptide again, which in turn is conjugated to the peptide chain comprising the parallel coiled-coil, however, connection of the lipid moiety to the peptide chain is preferred. Preferred lipid moieties are lipids containing two or three, preferably two extended hydrocarbyl chains.

"Long hydrocarbyl" means a straight alkyl or alkenyl group of at least 7 carbon atoms, for example straight alkyl or alkenyl consisting of between 8 and 50 C atoms, preferably between 8 and 25 C atoms. Alkenyl has preferably one, two or three double bonds in the chain, each with E or Z geometry, as is customarily found in natural fatty acids and fatty alcohols. Also included in the definition of "long hydrocarbyl" is branched alkyl or alkenyl, for example alkyl bearing a methyl or ethyl substituent at the second or third carbon atom counted from the end of the chain, as e.g. as in 2-ethyl-hexyl.

"Lower alkyl" means alkyl with 1 to 7 carbon atoms ($C_1$-$C_7$), preferably 1 to 4 carbon atoms ($C_1$-$C_4$), such as methyl, ethyl, n-propyl, iso-propyl, n-butyl, sec-butyl, iso-butyl or tert-butyl.

Particular preferred lipid moieties according to the invention are those of formula $Z^1$ to $Z^8$

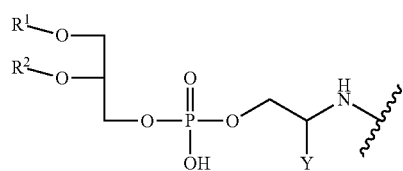

$Z^1$

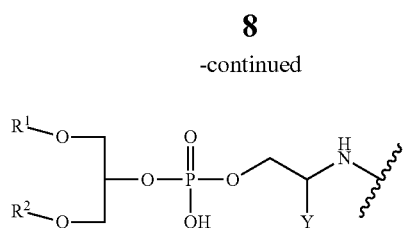

$Z^2$ wherein $R^1$ and $R^2$ are long hydrocarbyl or long hydrocarbyl-C=O and Y is H or COOH,

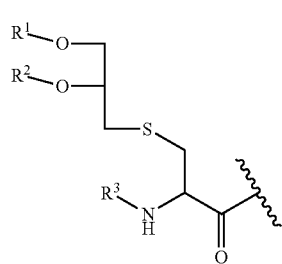

$Z^3$ wherein $R^1$, $R^2$ and $R^3$ are long hydrocarbyl or long hydrocarbyl-C=O or $R^1$ and $R^2$ are long hydrocarbyl or long hydrocarbyl-C=O and $R^3$ is H or acetyl or lower alkyl-C=O,

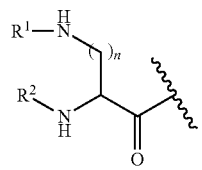

$Z^4$

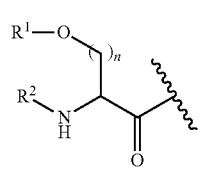

$Z^5$ wherein $R^1$ and $R^2$ are long hydrocarbyl or long hydrocarbyl-C=O and n is 1, 2, 3 or 4,

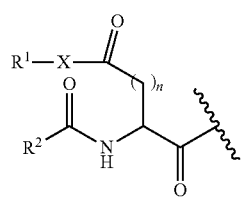

$Z^6$ wherein $R^1$ and $R^2$ are long hydrocarbyl, X is O or NH, and n is 1, 2, 3 or 4, or

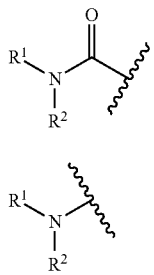

Z⁷

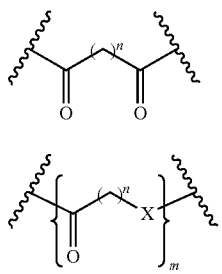

Z⁸ wherein R¹ and R² are long hydrocarbyl.

The lipid moiety contains at least two long hydrocarbyl chains such as found in fatty acids, e.g. as in $Z^1$ to $Z^8$. One preferred lipid moiety is a phospholipid of various types, e.g. of formula $Z^1$ or $Z^2$, that possess either ester- or ether-linked extended alkyl or alkenyl chains, such as either enantiomer of 1,2-dipalmitoyl-sn-glycero-3-phosphoethanolamine, or achiral analogues such as 1,3-dipalmitoyl-glycero-2-phosphoethanolamine. A preferred lipid moiety is a tri- or di-palmitoyl-S-glycerylcysteinyl residue (type $Z^3$) or lipid moieties of types $Z^4$ to $Z^8$. Most preferred are the lipid moieties described in the Examples.

The peptide chain (PC) is covalently linked to the lipid moiety (LM) at or near one terminus, i.e. the N terminus or the C terminus, preferably the N terminus. The lipid moiety may be directly attached as in

LM-PC        (1)

or via a linker (L) as in

LM-L-PC        (2).

If the peptide chain (PC) and the lipid moiety (LM) are directly linked, this is preferably accomplished through an amide bond between a lipid moiety carbonyl function and an amino function, e.g. the N terminal amino function, of the peptide chain (PC). Particular lipid moieties $Z^1$, $Z^2$ and $Z^8$ are preferably connected through an amide bond between their amine function and a carboxy function, e.g. the C terminal carboxy function, of the peptide chain (PC).

It will be apparent to those knowledgeable in this area, that a large variety of suitable linkers and coupling strategies exist, which include but are not limited to linkers based on dicarboxylic acid derivatives, linkers containing one or multiple ethylene glycol units, amino acid residues (including α-, β-, γ-, δ-amino acids), or sugar (carbohydrate) units, or containing heterocyclic rings. Particular linkers considered are linkers $L^1$ to $L^{16}$, wherein n is between 1 and 45 and m is between 1 and 45, for example wherein n is between 1 and 20 and m is between 1 and 20, shown with the connecting functional group C=O and/or X wherein X is O or NH:

L¹

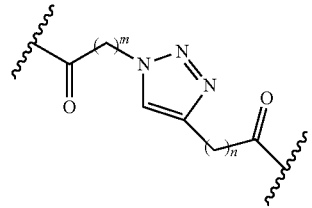

L²

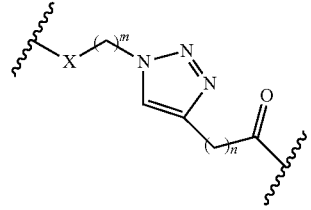

L³

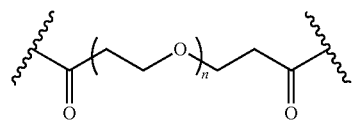

L⁴

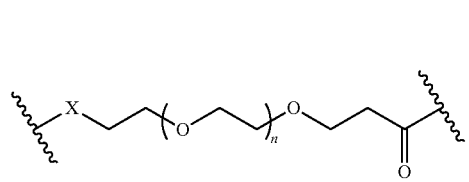

L⁵

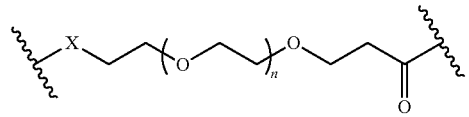

L⁶

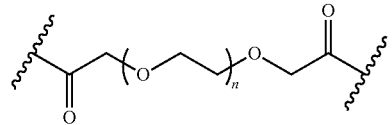

L⁷

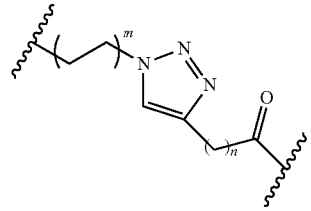

L⁸

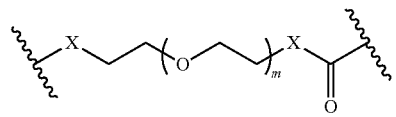

L⁹

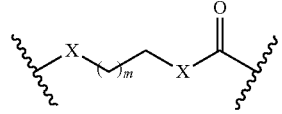

L¹⁰

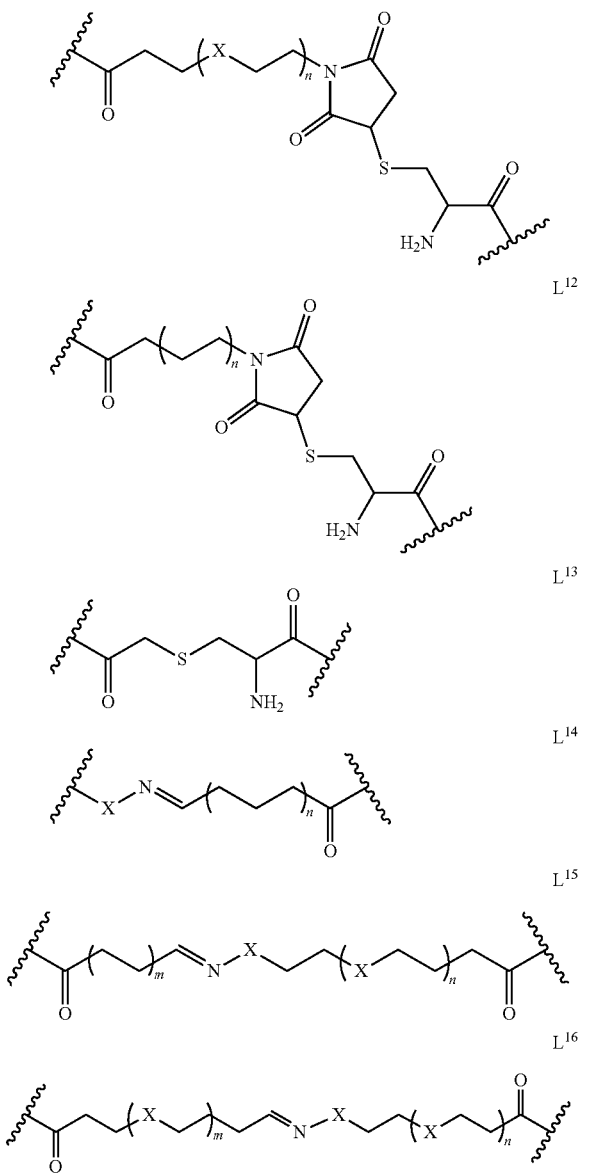

Most preferred are the linkers described in the Examples.

Particular linkers $L^1$ to $L^{16}$ may be connected to LM and PC as follows:

A carbonyl function shown for $L^1$ to $L^{16}$ may be connected to an amino function of a suitable lipid moiety (LM) and/or an amino function, e.g. the N terminal amino function, of the peptide chain (PC) through an amide bond. Alternatively a carbonyl function shown for $L^1$ to $L^{16}$ may be connected to a lipid moiety (LM) by replacement of the corresponding carbonyl function in particular lipid moieties $Z^3$ to $Z^7$.

A functional group X shown for $L^1$ to $L^{16}$ (with the meaning NH or O) may be connected to a carbonyl function of a suitable lipid moiety (LM) and/or a carboxy function, e.g. the C terminal carboxy function, of the peptide chain (PC) through an amide bond (for X=NH) or through an ester bond (for X=O).

The terminal $CH_2$ group of $L^8$ may be connected to an amino function of a suitable lipid moiety (LM), an amino function, e.g. the N terminal amino function, of the peptide chain (PC), or a carbonyl function of a suitable lipid moiety (LM).

"Near one terminus" as understood in this connection means that the lipid moiety or the linker is bound to the first, second, third, fourth or fifth amino acid calculated from the N terminal or C terminal end, respectively, of the peptide. The lipid moiety may be attached, directly or through a linker, to the backbone of the peptide structure or to the side chain of one of these amino acids near to the terminus.

"Coiled-coil domains" are designed by careful selection of appropriate amino acid sequences that form a thermodynamically stable, alpha-helical, parallel bundle of helices by spontaneous self-association.

A coiled-coil domain includes peptides based on canonical tandem heptad sequence repeats that form right handed amphipathic α-helices, which then assemble to form helical bundles with left-handed supercoils. Also included are peptides built from non-canonical, non-heptad-based repeats that form coiled-coils that are not necessarily left-handed or even regular supercoils.

Canonical coiled-coils occur widely in naturally occurring biologically active peptides and proteins, and have also been designed de novo. A set of rules has been elucidated for designing coiled-coil peptides that adopt helical bundles of defined oligomerization state, topology and stability (e.g. dimer, trimer, tetramer, pentamer, hexamer or heptamer).

These rules allow designers to build a peptide sequence compatible with a given target structure. Most important, the sequences of canonical coiled-coil peptides contain a characteristic seven-residue motif, which is repeated typically 3-10 times. The positions within one heptad motif are traditionally denoted abcdefg, with mostly (but not exclusively) hydrophobic residues occurring at sites a and d and generally polar, helix-favoring residues elsewhere. Tandem heptad motifs along a peptide chain have an average separation between the a and d residues that allows them to fall on one face of the alpha-helix. When two or more helices pack together into a coiled-coil bundle the hydrophobic faces of the helices associate and wrap around each other in order to maximize contacts between hydrophobic surfaces. The type of residue that may occur at each position within a heptad repeat will influence the stability and oligomerization state of the helical bundle. In general, mostly hydrophobic residues (Ala, Ile, Leu, Met, Val), or aromatic hydrophobic side chains (Phe, Trp and Tyr), are used at the a and d sites. The remaining b, c, e, f and g sites tend to be more permissive than the a and d sites, though polar and helix-favoring residues (Ala, Glu, Lys and Gln) are favored. The choice of residues at the a and d sites can influence the oligomerization state of the coiled coil (i.e. dimer vs. trimer). Thus, dimers are favored when non-β-branched residues (e.g. Leu) occur at the d positions; at these sites β-branched residues (Val and Ile) disfavor dimers. On the other hand, in dimers β-branched residues (Ile, Val) are preferred at the a sites. Another rule is that a=d=Ile or Leu favors trimers, which is useful in designing coiled coils that specifically form parallel trimers. These and other design rules are discussed in more detail in Woolfson, D. N., Adv. Prot. Chem. 2005, 70, 79-112.

The heptad motif codes for amphipathic alpha-helices that oligomerize through their hydrophobic faces. The coiled-coil domain includes at least three tandem heptad repeat motifs. The upper number of heptad repeats in each chain will influence the stability of the helical bundle. It is limited mainly by the feasibility of chemical synthesis of long peptides, but sequences containing more than three heptad repeats (e.g. four, five, six, seven and eight heptad repeats) are preferred. Examples discussed below form trimeric alpha-helical coiled-coils, but the invention likewise concerns dimeric, tetrameric, pentameric, hexameric and heptameric coiled-coil domains.

Coiled-coil domains according to the invention may have longer repeat units, for example 11-residue repeats and 15-residue repeats such as are present in naturally occurring coiled-coils. Thus the helical bundles required for the formation of aggregate structures may also arise when using coiled-coil motifs with periodicities other than seven. Coiled coils with unusual periodicities are also possible. In many naturally occurring coiled-coils the unbroken heptad repeat pattern may contain various discontinuities. Two common discontinuities are insertions of one residue into the heptad pattern, as well as insertions of three or four residues. For example, a one residue insertion is seen in the trimeric coiled coil of influenza hemagglutinin. Other naturally occurring coiled coils display a periodicity other than seven, for example, the regular periodicity of 11 residues (termed hendecads) found in the surface layer protein tetrabrachion of *Staphylothermus marinus*.

Other examples of coiled-coil peptide sequences occurring naturally in viral coat proteins are coiled-coil motifs forming trimeric helical bundles in the gp41 coat protein of HIV-1, and the F-glycoprotein of RSV. These coiled-coil domains are included in the definition of coiled-coil domain according to the invention.

The preferred coiled-coil peptides should contain between 3-8 tandemly linked heptad motifs. The heptad motifs within the coiled-coil may have identical sequences, or they may each have different sequences. In all cases, the seven positions of the seven amino acid residues within one heptad motif are designated with letters: a b c d e f g. The coiled-coil peptide, therefore, comprises an amino acid sequence having the positions $(abcdefg)_{3-8}$.

Preferred are coiled-coil peptide sequences containing between 3-8 tandemly linked heptad motifs, wherein positions a and d in each heptad motif (abcdefg) contain alpha-amino acids belonging to the Group 1 and/or to the Group 2 as defined hereinbelow. In addition, not more than two of all the a and d positions may be occupied by any amino acid residue belonging to the Group 3, and not more than one of all the a and d positions may be occupied by any amino acid residue belonging to the Group 4 or Group 5 or by glycine. In addition, in positions b, c, e, f and g, alpha-amino acids belonging to the Groups 3, 4 and 5 are preferred, but amino acids belonging to the Groups 1 and 2 are allowed, with the addition that not more than one of these positions within any one heptad motif may be glycine, but none may be proline.

Group 1 comprises alpha-amino acid residues with small to medium sized hydrophobic side chains. A hydrophobic residue refers to an amino acid side chain that is uncharged at physiological pH and that is repelled by aqueous solution. These side chains generally do not contain hydrogen bond donor groups, such as primary and secondary amides, primary and secondary amines and the corresponding protonated salts thereof, thiols, alcohols, ureas or thioureas. However, they may contain hydrogen bond acceptor groups such as ethers, thioethers, esters, tertiary amides, or tertiary amines. Genetically encoded amino acids in this group include alanine, isoleucine, leucine, methionine and valine.

Group 2 comprises amino acid residues with aromatic or heteroaromatic side chains. An aromatic amino acid residue refers to a hydrophobic amino acid having a side chain containing at least one ring having a conjugated aromatic π(pi)-electron system. In addition it may contain additional hydrophobic groups such as lower alkyl, aryl or halogen, hydrogen bond donor groups such as primary and secondary amines, and the corresponding protonated salts thereof, primary and secondary amides, alcohols, and hydrogen bond acceptor groups such as ethers, thioethers, esters, tertiary amides or tertiary amines. Genetically encoded aromatic amino acids include phenylalanine and tyrosine. A heteroaromatic amino acid residue refers to a hydrophobic amino acid having a side chain containing at least one ring having a conjugated aromatic π-system incorporating at least one heteroatom such as O, S and N. In addition such residues may contain hydrogen bond donor groups such as primary and secondary amides, primary and secondary amines and the corresponding protonated salts thereof, alcohols, and hydrogen bond acceptor groups such as ethers, thioethers, esters, tertiary amides or tertiary amines. Genetically encoded heteroaromatic amino acids include tryptophan and histidine.

Group 3 comprises amino acids containing side chains with polar non-charged residues. A polar non-charged residue refers to a hydrophilic side chain that is uncharged at physiological pH, but that is not repelled by aqueous solutions. Such side chains typically contain hydrogen bond donor groups such as primary and secondary amides, primary and secondary amines, thiols, and alcohols. These groups can form hydrogen bond networks with water molecules. In addition, they may also contain hydrogen bond acceptor groups such as ethers, thioethers, esters, tertiary amides, or tertiary amines. Genetically encoded polar non-charged amino acids include asparagine, cysteine, glutamine, serine and threonine.

Group 4 comprises amino acids containing side chains with polar cationic residues and acylated derivatives thereof, such as acylamino-derived residues and urea-derived residues. Polar cationic side chains refer to a basic side chain, which is protonated at physiological pH. Genetically encoded polar cationic amino acids include arginine, lysine and histidine. Citrulline is an example for a urea-derived amino acid residue.

Group 5 comprises amino acids containing side chains with polar anionic residues. Polar anionic refers to an acidic side chain, which is deprotonated at physiological pH.

Genetically encoded polar anionic amino acids include aspartic acid and glutamic acid. A particular polar cationic residue is —$(CH_2)_a COOH$ wherein a is 1 to 4.

More preferred are coiled-coil peptide sequences containing between 3 to 8 tandemly linked heptad motifs, wherein each heptad motif (abcdefg) may have any one of the following sequences:
1xx1xxx (referring respectively to the positions abcdefg);
1xx2xxx (referring respectively to the positions abcdefg);
2xx1xxx (referring respectively to the positions abcdefg); or
2xx2xxx (referring respectively to the positions abcdefg);

wherein 1 is a genetically encoded amino acid from Group 1, 2 is a genetically encoded amino acid from Group 2, and wherein x is a genetically encoded amino acid from Groups 1, 2, 3, 4 or 5 or glycine.

Equally preferred are coiled-coil peptide sequences identified in naturally occurring peptides and proteins, but excluding those of human origin. These are, for example, coiled-coils identified in viral and bacterial proteins.

The invention also relates to synthetic virus-like particles carrying PR peptide antigens, and to a method of preparing such synthetic virus-like particles involving dissolving the lipopeptide building blocks in a suitable carrier, preferably an aqueous buffer system (e.g. buffered saline or unbuffered saline). The solvent may be removed after preparation of the synthetic virus-like particles, for example by lyophilization or spray drying.

The invention further relates to a method of eliciting an immune response wherein an immunogenically effective amount of a synthetic virus-like particle carrying PR peptide antigens as described herein is administered to an animal. Any animal can be used, although warm-blooded animals, especially humans are considered here the most.

The invention also relates to a vaccine (or likewise to any other pharmaceutical preparation or medicine) comprising as principal or further active ingredient one or more synthetic virus-like particles carrying PR peptide antigens, alone or in combination with a pharmaceutically acceptable carrier.

The vaccine may also comprise one or more adjuvants such as a mineral salt (e.g. aluminium hydroxide, aluminium phosphate, aluminium sulfate, calcium phosphate), monophosphoryl lipid A (MPL), plant extracts containing saponins (e.g. QS-21), imidazo-quinolines (e.g. Imiquimod), muramyl dipeptides and tripeptides, lipopeptides, oil-in-water emulsions (e.g. Montanide ISA 720), cytokines (e.g. IL-2 or GM-CSF), mycobacterial and bacterial derivatives (e.g. Freund's complete adjuvant), BCG, nucleic acid derivatives (e.g. polyIC) and other adjuvants known to those skilled in the art.

Some components of the vaccine may also be encapsulated in or attached to bio-degradable polymers, which may for example be useful for controlled release, for example polylactic acid, poly-epsilon-caprolactone, polyhydroxybutyric acid, polyorthoesters, polyacetals, polydihydropyrans, polycyanoacrylates, and cross-linked or amphipathic block copolymers of hydrogels, or may be formulated in liposomes.

The vaccine is prepared in a manner known per se, for example by means of conventional dissolving and lyophilizing processes and/or may comprise excipients, for example preservatives, stabilizers, wetting agents, tonicity adjusting agents and/or emulsifiers, solubilizers, salts for regulating osmotic pressure and/or buffering substances to stabilize the pH.

The vaccine may be in liquid form or solid (e.g. lyophilized) form and can be sterilized by conventional, well-known sterilization techniques or sterile filtered. The resulting aqueous solution can be packaged for use as it is, or lyophilized, spray dried, or the solvent can be removed in another way. The solid form may be combined with a sterile diluent (e.g. water) prior to administration or may be administered as it is. Likewise the vaccine may comprise an emulsion, dispersion or suspension or any other form suitable for the intended route of administration.

The vaccine may be administered by any suitable enteral or parenteral route such as the intranasal, oral, sublingual, intramuscular, intradermal, transdermal, and subcutaneous or transcutaneous route. Other routes are known in the art that could also be employed.

A device may be used for administration such as conventional needles and syringes, micro needles, ballistic devices for administration of solids (e.g. as in WO 99/27961), patches (e.g. as in WO 98/20734), needle free injection systems (e.g. as in WO 01/054539), spray devices and the like, depending on the dose form and administration route. The device may be pre-filled or coated with the vaccine.

The vaccine comprises from approximately 0.05% to approximately 50% of the active ingredient in an appropriate dose form. Unit dose forms for parenteral administration are, for example, ampoules, pre-filled syringes or vials, e.g. vials containing from about 0.0001 mg to about 0.75 g of the active ingredient in a dose volume between approximately 0.25 ml and 1.5 ml.

The dosage of the active ingredient depends upon the intended recipient (e.g. species), its age, weight, and individual condition, and the administration route. An optimal dosage for a particular active ingredient and a particular target population can be determined by standard studies involving observation of appropriate immune responses in subjects.

The amount of vaccine sufficient to confer immunity to pathogenic *pneumococci* or other Gram-positive bacteria is determined by methods well known to those skilled in the art. This quantity will be determined based upon the characteristics of the vaccine recipient and the desired level of immunity to a disease caused by infection with *pneumococci* or other Gram-positive bacteria.

The vaccine may be administered as a single dose or as two or more doses at adequately spaced time points. The vaccine may also be administered together with other vaccines. For example, the vaccine may be used in prime-boost regimens in combination with other vaccines.

The vaccine is used for prophylactic or therapeutic purposes, or both, for the prevention and/or treatment of bacteraemia and other diseases caused by *S. pneumoniae* infections, such as pneumonia, acute sinusitis, otitis media, meningitis, bacteraemia, septicemia, osteomyelitis, septic arthritis, endocarditis, peritonitis, pericarditis, cellulitis or brain abscesses, or carriage. The vaccine is likewise useful for prophylactic or therapeutic purposes, or both, for the prevention and/or treatment of diseases caused by Group A *Streptococci* or *S. mutans*, such as pharyngitis, pyoderma, rheumatic fever, glomerulonephritis or caries.

For example, the vaccine protects against bacteraemia, pneumonia and meningitis, or against invasive pneumococcal disease (IPD), an infection in which *S. pneumoniae* can be isolated from the blood or another normally sterile site, or against bacteraemia, pneumonia and otitis media. Alternatively the vaccine protects against pharyngitis, pyoderma, rheumatic fever and glomerulonephritis or caries.

The vaccine may be administered to different target populations, including populations that are naive or have failed to respond previously to infection or vaccination, elderly persons suitably aged (e.g. over 65, 75 or 85 years old), adults at elevated risks such as people working in health institutions, young adults with a risk factor, immune-compromised persons or pediatric populations.

The invention furthermore relates to a method of making a vaccine comprising mixing synthetic virus-like particles carrying PR peptide antigens with synthetic virus-like particles carrying other antigens or antigens not carried by synthetic virus-like particles.

The invention also relates to antibodies to synthetic virus-like particles carrying protective PR peptide antigens, especially to antibodies to PR peptide antigens. Antibodies to PR peptide antigens can cross-react with a broad variety of genetically diverse strains and different capsular serotypes, and extend the median survival time in a model of passive transfer.

Protective antibodies to PR peptide antigens can have opsonophagocytic activity (OPA). Antibodies with OPA may be detected in vitro by a suitable assay, for example an opsonophagocytic killing assay (OPKA) using a cell line or whole blood from a donor. Protective antibodies can also mediate protection by other mechanisms that do not involve OPA.

The invention also relates to the use of protective antibodies to PR peptides as described herein for the manufacture of a pharmaceutical preparation or medicine for therapeutic and/or prophylactic purposes and also for the manufacture of a diagnostic kit.

Not all PR peptides may be equally protective as vaccine antigens. Protective PR peptides are preferred. They may be identified by using well-known methods such as challenge studies in a suitable animal model of streptococcal diseases. For example, in a pneumococcal sepsis model, mice may be immunized with synthetic virus-like particles carrying PR peptide antigens as described herein, and subsequently challenged intravenously with a lethal dose of *S. pneumoniae*. In this model mice immunized with synthetic virus-like particles carrying protective PR peptide antigens then have significantly longer survival time compared to that of immunized control mice.

PR peptide antigens can also be derived from other pathogenic *streptococci* such as *S. pyogenes*, *S. agalactiae*, *S. mutans*, *S. equi*, *S. suis*, *S. dysgalactiae*, *Peptostreptococcus magnus* or other pathogenic Gram-positive bacteria, such as *Staphylococcus aureus*, and synthetic virus-like particles carrying these PR peptide antigens are likewise useful for vaccines against these bacteria.

Preferred PR peptide antigen sequences from *S. pneumoniae* PspA and PspC are collected in Table 2 below. Peptide antigen P3 is a synthetic construct combining two sequences.

TABLE 2

| Name | SEQ ID NO: | Sequence |
| --- | --- | --- |
| P1 | 27 | PAPKPEQPAEQPKPAPAPQPAPAPKPEKT |
| P2 | 28 | PKPEQPAPAPKPEQPAKPEKPA |
| P3 | 29 | PAPKPEQPAEQPKPEQPAPAPKPEQPAKPEKP |
| P4 | 30 | PAPKPEQPAEQPKPA |
| P5 | 31 | PAPQPAPAPKPEKT |
| P6 | 32 | QPAEQPKPAPAPQPAP |
| P7 | 33 | PAPAPKPEQPAEQPKP |
| P8 | 34 | PAPEAPAEQPKPAPAPQPAPAPKPEKPAEQPKPEKT |
| P9 | 35 | PAEQPKPAPAPQPAPAPKPEKPAEQ |
| P10 | 36 | PKPAPAPQPAPAPKPEKPAEQPKPEKT |
| P11 | 37 | KAEKPAPAPQPEQPAPAPKT |
| P12 | 38 | PAPAPQPEQPAPAPQPEQPAPAPKPEQPAPAPKPEQPTPA |
| P13 | 39 | PAPAPQPEQPAPAPKPEQPAPAPKPEQPTPAPKPEQPTPAPKT |
| P14 | 40 | PEQPAPAPKPEQPAPAPKPEQPTPAPKPEQPTPAPKT |
| P15 | 41 | PKPEQPTPAPKPEQPTPAPKT |
| P16 | 42 | PKPEQPAEQPKPAPAPQ |
| P17 | 43 | PKPEQPAPAPKPEQPAKPEKPAEEPTQPEKPATPKT |
| P18 | 44 | PKPEQPAKPEKPAEEPTQPEKPATPKT |
| P19 | 45 | PAPAPQPAPAPKPAPAPQPEKPAEQPKAEKPA |
| P20 | 46 | PETPAPAPKPETPAPAPEAPAPAPAPKPEQPAPAPKPEKSA |
| P21 | 47 | PAPAPKPEQPAPAPKPEKSA |
| P22 | 48 | PKPEQPAPAPKPEKSA |
| P23 | 49 | KAEKPAPAPKPEQPVPAPKT |
| P24 | 50 | PAPAPKPAPAPQPEKPAPAPAPKPEKSA |
| P25 | 51 | PAPEQPTEPTQPEKPAEETPAPKPEKPAEQPKAEKT |
| P26 | 52 | PAPKPEKPAEQPKAEKT |
| P27 | 53 | PAPAPKPEQPAEQPKPAPAPQPEKPAEEPENPAPAP |
| P28 | 54 | APAPKPETPAPAPEAPAPAPAPKPEQPAPAPKPEKS |
| P29 | 55 | APAPETPAPEAPAEQPKPAPAPQPAPAPKPEKPAEQPKPEKT |
| P30 | 56 | PAPEQPTEPTQPEKPAEETPAPKPEKPAEQPKAEKT |
| P31 | 57 | APAPKPETPAPAPEAPAPAPAPKPEQPAPAPKPEKS |
| P32 | 58 | APAPETPAPEAPAEQPKPAPAPQPAPAPKPEKPAEQPKPEKT |
| P33 | 59 | APAPKPETPAPAPEAPAPAPAPKPEQPAPAPKPEKS |
| P34 | 60 | APAPETPAPEAPAEQPKPAPAPQPAPAPKPEKPAEQPKPEKT |
| P35 | 61 | APAPETPAPEAPAEQPKPAPAPQPAPAPKPEKPAEQPKAEKPA |
| P36 | 62 | PQPEQPAPAPKPEQPAPAPKPEQPTPAPKPEHP |
| P37 | 63 | PAPAPQPEQPAPAPQPEQPAPAPKPEQPAPAPKPE |
| P38 | 64 | PAPQPEQPAPAPKPEQPAPAPKPEQPTPAPKPP |
| P39 | 65 | PAPAPAPKPEQPAPAPAPKPEQPAPAPAPKPEQPA |
| P40 | 66 | PAPAPKPEQPAPAPAPKPEQPAPAPAPKPEQPT |
| P41 | 67 | PAPAPQPEQPAPAPKPEQPAPAPKPEQPTPAPKPE |
| P42 | 68 | PAPAPKPEQPAEQPKPAPAPQPAPAPKPEKQ |
| P43 | 69 | PAPAPQPEQPAPAPQPEQPAPAPKPEQPAPAPKPA |
| P44 | 70 | PKPEQPTPAPKPEQPTPAPKPEQPTPAPKPEQPT |
| P45 | 71 | PEKPAPAPEKPAPAPEKPAPA |
| P46 | 72 | PAPKPAPAPKPAPAPAPKPEKPA |
| P47 | 73 | PAPAPTPEAPAPAPAPKP |
| P48 | 74 | PKPEQPAKPEKPAEEPTQPEKPA |
| P49 | 75 | PAKPEKPAEEPTQPEKPA |
| P50 | 76 | PAPAPKPEQPAKPEKPAEEPTQPEKPA |
| P51 | 77 | PKPEQPAPAPNPEQPAKPEKPAEEPTQPEKPA |
| P52 | 78 | PKPEQPAPAPAPKPEQPAPAPAPKPEQPA |
| P53 | 79 | PKPEQPAPAPKPEQPAKPEKPAEEPTQPEKPA |
| P54 | 80 | PKPEQPAPAPAPKPEQPAKPEKPAEEPTQPEKPA |

TABLE 2 -continued

| Name | SEQ ID NO: | Sequence |
|---|---|---|
| P55 | 81 | PAPAPQPEQPAPAPKPEQPAPAPKPEQPAPAPKPEQPA |
| P56 | 82 | PAPAPKPEQPTPAPKPEQPTPAPKPEQPAPAPKPEQPAPAPKP |
| P57 | 83 | PARALQPEQPAPAPKPEQPTPAPKPEQPTPAPKPEQPAPAPKP |

In the preferred PR peptides of SEQ ID NO: 27 to 83, one, two or three amino acids may be replaced by other amino acids.

Alternative PR peptide antigen sequences from *S. pneumoniae* and from *S. pyogenes, S. agalactiae, S. mutans, S. suis, S. equi, S. dysgalactiae, Peptostreptococcus magnus* and *Staphylococcus aureus* proteins are collected in Table 3 below.

TABLE 3

| Name | SEQ ID NO: | Sequence[a) |
|---|---|---|
| P58 | 84 | SRLEQPSLQPTPEPSPGPQPAPN |
| P59 | 85 | RPEEPSPQPTPEPSPSPQPAPSNP |
| P60 | 86 | HWVPDSRPEQPSPQSTPEPSPSPQPAPNPQPAPSNP |
| P61 | 87 | PKSNQIGQPTLPNNSLATPSPSLPINPGTSHE |
| P62 | 88 | PEVTPTPETPEQPGEKAPEKSPEVTPTPETPEQP |
| P63 | 89 | PEVTPTPETPEQPGEKAPEK |
| P64 | 90 | PEKSPEVTPTPETPEQP |
| P65 | 91 | KAPEKSPEVTPTPEMP |
| P66 | 92 | PGKPAPKTPEVPQKPDTAPHTPKTP |
| P67 | 93 | KPSAPKAPEKAPAPKAPK |
| P68 | 94 | PAPKAPKASEQSSNPKAPAPKSAP |
| P69 | 95 | PGPAGPRGLQGPQGPRGDKGET |
| P70 | 96 | PQAPSTPEKQPEVPESP |
| P71 | 97 | PETPDAPSTPKDEPQAP |
| P72 | 98 | PAPVEPSYEAEPTPPTRTPDQAEPNKPT |
| P73 | 99 | PTYETEKPLEPAPVEPSYEAEPT |
| P74 | 100 | KPTAPTKPTYETEKPLKPAPVAPNYEKEPT |
| P75 | 101 | KPVVPEQPDEPGEIEPIP |
| P76 | 102 | PEVPSEPETPTPPTPEVPAEPGKPVPPAK |
| P78 | 103 | KYTPKKPNKPIYPEKPKDKTPPTKPDHS |
| P79 | 104 | PEKPVEPSEPST |
| P80 | 105 | KPVEPSEPSTPDVPSNPSNPSTPDVPSTPDVPSNPSTPEVPSNP |
| P81 | 106 | PQVEPNVPDTPQEKPLT |
| P82 | 107 | KPLTPLAPSEPSQPSIPETPLIPSEPSVPET |
| P83 | 108 | PEVKPDVKPEAKPEAKPA |

TABLE 3 -continued

| Name | SEQ ID NO: | Sequence[a) |
|---|---|---|
| P84 | 109 | KPEAKPEAKPA |
| P85 | 110 | PDVKPEAKPEAKPDVKPEAK |
| P86 | 111 | PETPDTPKIPELPQ |
| P87 | 112 | PDTPQAPDTPHVPESPKTPE |

[a) SEQ ID NO of proteins from *S. pneumoniae*: 84-87; *S. pyogenes*: 88-92, 95; *S. equi*: 93-94; *S. suis*: 96-97; *S. mutans*: 98-100; *S. aureus*: 101-103; *Peptostreptococcus magnus*: 104; *S. dysgalactiae*: 105-107; *S. agalactiae*: 108-112.

In the preferred PR peptides of SEQ ID NO: 84 to 112, one, two or three amino acids may be replaced by other amino acids.

Additional sequences, which, when administered alone, offer limited protective potential, may be conjugated to PR peptide antigens, in particular sequences derived from regions of PspA or PspC, or other proteins, which do not comprise proline in every $3^{rd}$ or $4^{th}$ position and/or comprise less than 15% proline, in particular the sequences:

(SEQ ID NO: 113)
QQAEEDYARRSEEEYNRLPQQQPPKAEKP,
(non-proline block)
and (SEQ ID NO: 114)
AEDQKEEDRRNYPTNTYKTLELEIAESDVEV.
(helical peptide from PspC)

Other sequences that may be combined with PR peptide antigens include sequences derived from bacterial surface proteins that do not contain a proline rich region, including:

Sequences from StkP, preferably the C-terminal 79-82 amino acids, (SEQ ID NO: 115)
SVAMPSYIGSSLEFTKNNLIQIVGIKEANIEVVEVTTAPAGSAEGMVVEQ

SPRAGEKVDLNKTRVKISIYKPKTTSATP, and fragments thereof;

sequences from PsaA, preferably amino acids 250-309:

(SEQ ID NO: 116)
SLFVESSVDDRPMKTVSQDTNIPIYAQIFTDSIAEQGKEGDSYYSMMKYN

LDKIAEGLAK;

sequences from cholesterol dependent cytolysins, such as the $4^{th}$ domain of Ply, amino acids 360-471:

(SEQ ID NO: 117)
NGDLLLDHSGAYVAQYYITWNELSYDHQGKEVLTPKAWDRNGQDLTAHFT

TSIPLKGNVRNLSVKIRECTGLAWEWWRTVYEKTDLPLVRKRTISIWGTT

LYPQVEDKVEND, and fragments thereof;

streptococcal polyhistidine triad proteins, for example fragments from the C-terminal half of *S. pneumoniae* PhtD, e.g. the amino acids 680-770:

(SEQ ID NO: 118)
VEHPNERPHSDNGFGNASDHVRKNKVDQDSKPDEDKEHDEVSEPTHPESD

EKENHAGLNPSADNLYKPSTDTEETEEEAEDTTDEAEIPQV, or the amino acids 771-839:

(SEQ ID NO: 119)
ENSVINAKIADAEALLEKVTDPSIRQNAMETLTGLKSSLLLGTKDNNTIS

AEVDSLLALLKESQPAPIQ, or fragments thereof.

In the preferred sequences SEQ ID NO: 113-119, one, two or three amino acids may be replaced by other amino acids.

Further sequences include the sequences described in PCT/US2012/022127 or US 2005/0020813 A1. Alternative sequences include sequences described in EP 0280576 A2.

Additional antigens may be combined with synthetic virus-like particles carrying PR peptide antigens. For example, S. pneumoniae proteins identified in WO 98/18931, WO 98/18930, U.S. Pat. Nos. 6,699,703, 6,800,744, WO 97/43303, and WO 97/37026; Lyt family (LytX), Pht family (PhtX), Sp128, type 1 or type 2 pilus proteins, other streptococcal antigens such as those identified in WO 1993/005155, WO 2002/034771, WO 2002/083859, WO 2002/34771, WO 2003/093306, WO 2004/041157, or WO 2005/002619; or other antigens such as Sp101, Sp130, Sp125 or Sp133, may be combined with synthetic virus-like particles carrying pneumococcal PR peptide antigens.

Saccharide antigens may also be combined with synthetic virus-like particles carrying PR peptide antigens, such as capsular saccharides of S. pneumoniae serotypes 1, 3, 4, 5, 6A, 6B, 7F, 8, 9V, 14, 18C, 19A, 19F, 22F, 23F or 33F. Alternatively other saccharides may be combined with PR peptide antigens, such as saccharides derived from other S. pneumoniae serotypes, and/or saccharides from other Gram-positive bacteria (e.g. saccharides derived from S. agalactiae, S. pyogenes, and/or S. aureus).

Likewise proteins from other Gram-positive bacteria may be combined with synthetic virus-like particles carrying PR peptide antigens, e.g. one or more proteins from S. pyogenes, including M protein, fibronectin binding protein (SfbI), Streptococcal heme-associated protein (Shp), or proteins identified in Streptolysin S (SagA), and/or one or more proteins from S. aureus, such as Alpha-toxin, Clumping factor A (ClfA), Collagen binding protein (CNA), Fibronectin-binding protein A (FbA), Extracellular Fibrinogen-binding Protein (Efb), Iron regulated surface determinant (Isd) proteins, Penicillin binding protein 2a (PBP2a), Serine Aspartate repeat proteins (Sdr) and/or binder of IgG (Sbi). Likewise also peptide antigens derived from such proteins may be combined with synthetic virus-like particles carrying PR peptide antigens.

EXAMPLES

Abbreviations:
Boc, t-butoxycarbonyl;
BSA, bovine serum albumin;
DIEA, diisopropylethylamine;
DMF, N,N-dimethylformamide;
EDT, ethanedithiol;
Fmoc, 9-fluorenylmethoxycarbonyl;
HATU, 2-(1H-9-azabenzotriazole-1-yl)-1,1,3,3-tetramethyluronium hexafluorophosphate;
HBTU, 2-[1H-benzotriazole-1-yl]-1,1,3,3-tetramethyluronium hexafluorophosphate;
HOBt, N-hydroxybenzotriazole;
Pbf, 2,2,4,6,7-pentamethyldihydrobenzofuran-5-sulfonyl;
NMP, N-methylpyrrolidone;
MBHA, methylbenzhydrylamine;
OD, optical density;
iPr$_2$O, diisopropylether;
PCR, polymerase chain reaction
PyBOP, (benzotriazol-1-yloxy)-tripyrrolidinophosphonium-hexafluorophosphate;
PEO6, N-Fmoc-21-amino-4,7,10,13,16,19-hexaoxaheneicosanoic acid
r.t., room temperature;
RP-HPLC, reversed-phase high performance liquid chromatography;
TA, thioanisole;
TIS, triisopropylsilane;
Trt, trityl;
TFA, trifluoroacetic acid;
TFE, 2,2,2-trifluoroethanol;
$t_R$, retention time;
SD, standard deviation.

Example 1

Design and Synthesis of PR Peptides

The proline-rich region of the PspA from a highly virulent serotype 1 clinical isolate SP1577 (Leimkugel et al., *JID*, 2005, 192, 192-199) was amplified and sequenced using two primers (LSM13 and SKH2) according to Hollingshead, Becker et al., *Infect Immun*, 2000, 68, 5889-5900.

(SEQ ID NO: 120)
LSM13: 5'-GCAAGCTTATGATATAGAAATTTGTAAC-3'

(SEQ ID NO: 121)
SKH2: 5'-CCACATACCGTTTTCTTGTTTCCAGCC-3'

Amplification of the proline-rich region was carried out by PCR using the primers LSM13 and SKH2 and GoTaq Polymerase (PCR conditions: Annealing 48° C. for 1 min, Elongation 72° C. for 3 min, 30 cycles). The obtained fragments, which were around 1.2 kb in size, were isolated from the PCR reaction and sequenced using the primers LSM13 and SKH2. Around 1,100 bases of the pspA gene could be read. The translated nucleotide sequence is shown below. The proline-rich region, including non-proline block is shown in italics.

(SEQ ID NO: 122)
XXLGAGFVXX XPTXXXXXEA PVASQXKAEK DXDAXKRDAE

NXKKALEEAK XXQKKYEDDQ KKTEEKXKKE KEASKEEQAA

NLKYQQELVK YASEKDSVKK AKILKEVEEA EKEHKKKRAE

FEKVRSEVIP SAEELKKTRQ KAEEAKAKEA ELIKKVEEAE

KKVTEAKQKL DAERAKEVAL QAKIAELENE VYRLETELKG

IDESDSEDYV KEGLRAPLQS ELDAKRTKLS TLEELSDKID

ELDAEIAKLE KNVEYFKKTD AEQTEQYLAA AEKDLADKKA

ELEKTEADLK KAVNEPEKPA EET*PAPAPKP EQPAEQPKPA*

*PAPQPAPAPK PEKTDDQQAE EDYARRSEEE YNRLPQQQPP*

*KAEKPAPAPK PEQPVPAPKT GWKQENGMWC R*

From this sequence the P1 PR Sequence (PAPKPEQ-PAEQPKPAPAPQPAPAPKPEKT, SEQ ID NO:27) was selected. P1 is located between the helical/coiled-coil region and the non-proline block of the SP1577 PspA.

In order to enable conjugation to SVLP lipopeptides, the following maleimidopeptides were designed and synthesized:

Maleimidopeptide 1:

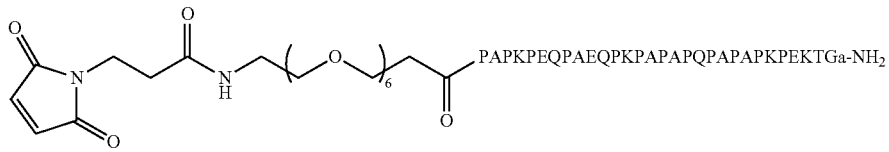

(1)

In maleimidopeptide 1 3-maleimidopropionic acid is coupled to the N-terminus in P1 (SEQ ID NO:27) via an 21-amino-3,6,9,12,15,18-hexaoxaheneicosan-21-oic acid linker, and a glycine is added to the C-terminus P1, followed by a D-alanine residue ("a") as the amide ("NH$_2$") in order to confer stability towards exoproteases.

The synthesis of maleimidopeptide 1 was carried out using Fmoc Solid Phase Peptide Synthesis (SPPS) methods as follows:

The peptide PAPKPEQPAEQPKPAPAPQPAPAPKPEK-TGa (SEQ ID NO:27 extended by glycine-D-alanine) was assembled on an ABI 433A peptide synthesizer using Rink Amide MBHA resin (loading: 0.69 mml/g) (362 mg, 0.25 mmol) and standard Fmoc-SPPS protocols. The following amino acids were used (in the correct order): Fmoc-Ala-OH, Fmoc-D-Ala-OH, Fmoc-Glu(OtBu)-OH, Fmoc-Gln(Trt)-OH, Fmoc-Gly-OH, Fmoc-Lys(Boc)-OH, Fmoc-Pro-OH and Fmoc-Thr(tBu)-OH. After assembly and removal of the N-terminal Fmoc protecting group, the resin was washed with N-methyl-2-pyrrolidone (NMP) and CH$_2$Cl$_2$. For coupling of the maleimide, a portion of the resin (ca. 0.1 mmol) was washed with DMF and a solution of Fmoc-PEO6-OH (115 mg, 0.2 mmol) PyBOP (104 mg, 0.2 mmol), HOBt (27 mg, 0.2 mmol) and DIEA (66 µl, 0.4 mmol) in 4.5 ml DMF was prepared, mixed for 30 seconds and added to the resin under argon. The mixture was shaken for 16 h. The resin was filtered and washed 4× with DMF. The Fmoc group was then removed by treatment with 20% piperidine in DMF (6×2 min.). The resin was then washed again with DMF and a solution of 3-maleimidopropionic acid (34 mg, 0.2 mmol), PyBOP (104 mg, 0.2 mmol), HOBt (27 mg, 0.2 mmol) and DIEA (66 µl, 0.4 mmol) in DMF was prepared and added to the resin under argon. The resin was shaken for 3 h, filtered, washed sequentially 4 times with DMF, CH$_2$Cl$_2$ and MeOH, and dried over night in vacuo over KOH pellets. For cleavage of the peptide from the resin and removal of side-chain protecting groups, TFA/TIS/TA/phenol 85:5:5:5 (10 ml) was prepared and added to the dry resin under argon atmosphere. The resin was shaken for 3 h, filtered and the maleimidopeptide 1 was precipitated with iPr$_2$O, pre-chilled to −20° C. (50 ml). The peptide was then washed 4 times with iPr$_2$O, air-dried over night and purified by RP-HPLC using a preparative C18 column (Agilent Zorbax SB300 PrepHT, 250×21.5 mm) and a linear gradient of 10-40% MeCN in H$_2$O (+0.1% TFA) in 16 min. and lyophilized to afford 1 as a white powder. The peptide was analyzed by analytical RP-HPLC using an Agilent XDB-C18 column (250×4.6 mm) and a linear gradient of 10-100% MeCN in H$_2$O (+0.1% TFA) in 25 min: Purity>97%; t$_R$=8.53 min.

ESI-MS: MW calculated for C$_{163}$H$_{259}$N$_{41}$O$_{51}$: 3609.1 Da. MW found: 3609.7 (±0.02%).

Maleimidopeptide 2:

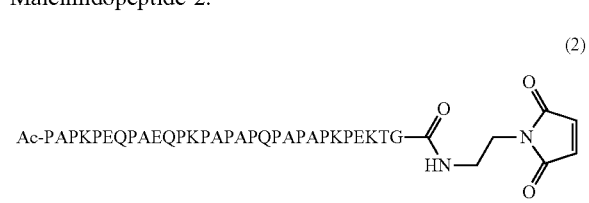

(2)

In this maleimidopeptide a glycine is added to the C-terminus in P1 (SEQ ID NO:27) and the maleimide is coupled to the glycine P1 via an amino ethyl spacer. The N-terminus is acetylated.

The peptide chain in maleimidopeptide 2 was assembled using Fmoc SPPS on an ABI 433A as described for 1, except that 2-chlorotrityl resin preloaded with Fmoc-Gly-OH to a resin substitution level of 0.6 mmol/g (416 mg, 0.25 mmol) was used instead of Rink amide MBHA resin as the solid phase support. Following assembly and removal of the N-terminal Fmoc protecting group, the resin was acetylated by treatment with a solution of 0.5M Ac$_2$O, 0.05M HOBt and 0.136M DIEA in NMP (10 ml) with shaking for 30 min. The resin was then washed 4 times with DMF, 4 times with CH$_2$Cl$_2$ and treated with TFE/CH$_2$Cl$_2$ 2:8 (10 ml) with shaking under argon for 4 h to release the fully side chain protected peptide from the resin. The resin was filtered and washed twice with 10 ml TFE/CH$_2$Cl$_2$ 2:8, the filtrate was concentrated and the protected peptide was precipitated with 4° C. cold Et$_2$O and washed 4 times with Et$_2$O. The protected peptide was then dried in vacuo over night and stored at −20° C.

For coupling of the maleimide, a portion of the crude side-chain protected peptide (100 mg), HATU (15 mg, 39 µmol), HOAt (5 mg, 39 µmol) were dissolved in DMF (0.8 ml), DIEA (23 µl, 142 µmol) was added and the mixture was stirred for 1 min. A solution of N-(2-aminoethyl)maleimide TFA salt (150 mg, 60 µmol) in DMF (0.2 ml) was added and the mixture was stirred for 3 h under argon atmosphere. The DMF was then removed under reduced pressure. The side-chain protected peptide was suspended in 0.3 ml CH$_2$Cl$_2$, precipitated with 4° C. cold Et$_2$O, washed 4 times with Et$_2$O and dried in vacuo over night.

The side-chain protecting groups were then removed and the peptide was precipitated and purified as described above for 1 and the final product 2 was analyzed by analytical RP-HPLC using an Agilent XDB-C18 column (250×4.6 mm) and a linear gradient of 10-100% MeCN in H$_2$O (+0.1% TFA) in 25 min: Purity>97%; t$_R$=7.06 min. MALDI-TOF MS: MW calculated for C$_{146}$H$_{227}$N$_{39}$O$_{43}$: 3216.6 Da. MW found: 3215.7 Da (±0.05%).

Maleimidopeptide 3:

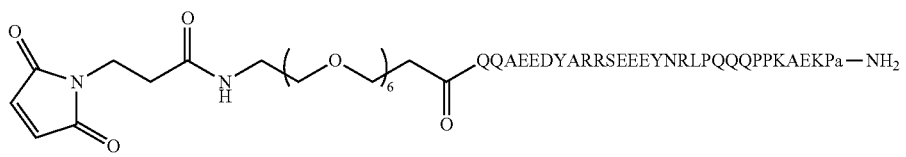

(3)

In maleimidopeptide 3, 3-maleimidopropionic acid is coupled to the N-terminus of SEQ-ID NO:113 via an 21-amino-3,6,9,12,15,18-hexaoxaheneicosan-21-oic acid linker, and the C-terminus is capped with D-alanine ("a") and amidated. SEQ ID NO:113 corresponds to the non-proline block of the P1577 PspA.

Maleimidopeptide 3 was synthesized and purified as described above for maleimidopeptide 1 and analyzed by analytical RP-HPLC using an Agilent XDB-C18 column (250×4.6 mm) and a linear gradient of 10-100% MeCN in $H_2O$ (+0.1% TFA) in 25 min: Purity>97%; $t_R$=5.31 min.

MALDI-TOF MS: MW calculated for $C_{174}H_{272}N_{50}O_{63}$: 4072.3 Da. MW found: 4071.0 Da (±0.05%).

Other PR sequences can be obtained by sequencing pspA or pspC genes, or, alternatively, may be accessed in public databases, such as UniProtKB. For example, the PspA sequence of serotype 19A isolate TCH8431 (UniProtKB accession no. D6ZPW2) is:

```
                                       (SEQ ID NO: 123)
MNKKKMILTS  LASVAILGAG  FVTSQPTVVR  AEESPVASQS

KAEKDYDAAV  KKSEAAKKHY  EEAKKKAEDA  QKKYDEDQKK

TEAKAEKERK  ASEKIAEATK  EVQQAYLAYL  QASNESQRKE

ADKKIKEATQ  RKDEAEAAFA  TIRTTIVVPE  PSELAETKKK

AEEAKAEEKV  AKRKYDYATL  KLALAKKEVE  AKELEIEKLQ

YEISTLEQEV  ATAQHQVDNL  KKLLAGADPD  DGTEVIEAKL

KKGEAELNAK  QAELAKKQTE  LEKLLDSLDP  EGKTQDELDK

EAEEAELDKK  ADELQNKVAD  LEKEISNLEI  LLGGADPEDD

TAALQNKLAA  KKAELAKKQT  ELEKLLDSLD  PEGKTQDELD

KEAEEAELDK  KADELQNKVA  DLEKEISNLE  ILLGGADSED

DTAALQNKLA  TKKAELEKTQ  KELDAALNEL  GPDGDEEETP

APAPQPEQPA  PAPKPEQPAP  APKPEQPAPA  PKPEQPAPAP

KPEQPAKPEK  PAEEPTQPEK  PATPKTGWKQ  ENGMWYFYNT

DGSMATGWLQ  NNGSWYYLNA  NGSMATGWVK  DGDTWYYLEA

SGAMKASQWF  KVSDKWYYVN  SNGAMATGWL  QYNGSWYYLN

ANGDMATGWL  QYNGSWYYLN  ANGDMATGWA  KVNGSWYYLN

ANGAMATGWA  KVNGSWYYLN  ANGSMATGWV  KDGDTWYYLE
```

-continued
```
ASGAMKASQW  FKVSDKWYYV  NGLGALAVNT  TVDGYKVNAN

GEW
```

From this sequence the P2 sequence (PKPEQPAPAPK-PEQPAKPEKPA, SEQ ID NO:28) was selected. P2 is located immediately after the helical/coiled-coil region of the TCH8431 PspA. In order to facilitate conjugation to SVLP lipopeptides the following maleimido-peptides were designed and synthesized:

Maleimidopeptide 4

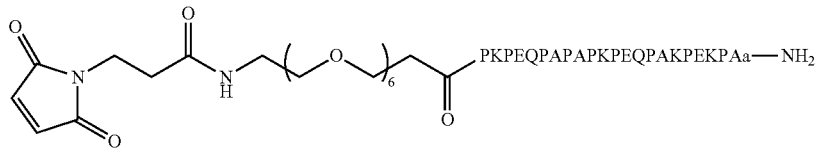

(4)

This maleimidopeptide comprises 3-maleimidopropionic acid coupled via an 21-amino-3,6,9,12,15,18-hexaoxaheneicosan-21-oic acid linker to the N-terminus of P2 (SEQ ID NO:28). The "a" denotes D-alanine. The C-terminus is amidated.

Maleimidopeptide 4 was synthesized and purified as described above for maleimidopeptide 1 and analyzed by analytical RP-HPLC using an Agilent XDB-C18 column (250×4.6 mm) and a linear gradient of 10-100% MeCN in $H_2O$ (+0.1% TFA) in 25 min: Purity>97%; $t_R$=5.21 min. MALDI-TOF MS: MW calculated for $C_{131}H_{210}N_{32}O_4$: 2889.3 Da. MW found: 2888.8 Da (±0.05%).

Maleimidopeptide 5

(5)

In this maleimidopeptide a glycine is added to the C-terminus of P2 (SEQ ID NO: 28), and the maleimide is coupled to the glycine via an amino ethyl spacer. The N-terminus is acetylated.

Maleimidopeptide 5 was synthesized and purified as described above for maleimidopeptide 2 and analyzed by analytical RP-HPLC using an Agilent XDB-C18 column (250×4.6 mm) and a linear gradient of 10-100% MeCN in $H_2O$ (+0.1% TFA) in 25 min: Purity>97%; $t_R$=6.31 min. ESI MS: MW calculated for $C_{113}H_{178}N_{30}O_{33}$: 2484.8 Da. MW found: 2483.2 Da (±0.02%).

Maleimidopeptide 6

Artificial PR sequences can be generated by fusing short PR sequences from two or more distinct PspA proteins. For example the sequence P3 (SEQ ID NO: 29) was designed by fusing the N-terminal residue PAPKPEQPAEQ (SEQ ID NO: 124) in P1 to P2 (SEQ ID NO: 28) and replacing the C-terminal Ala in P2 by a Gly residue. In order to enable conjugation the following maleimidopeptide was designed and synthesized:

6

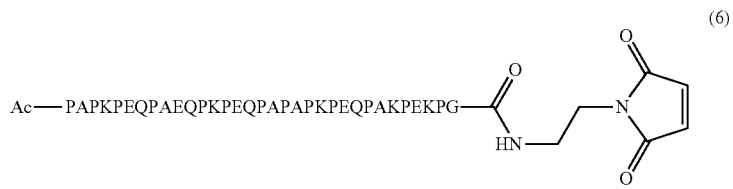

(6)

Maleimidopeptide 6 was synthesized and purified as described above for maleimidopeptide 2 and analyzed by analytical RP-HPLC using an Agilent XDB-C18 column (250×4.6 mm) and a linear gradient of 10-100% MeCN in H$_2$O (+0.1% TFA) in 25 min: Purity>97%; t$_R$=10.11 min. MALDI MS: MW calculated for C$_{164}$H$_{255}$N$_{45}$O$_{50}$: 3657.1 Da. MW found: 3654.9 Da (±0.05%).

Further examples for PR peptide antigen are described below:

Maleidmidopeptide 7

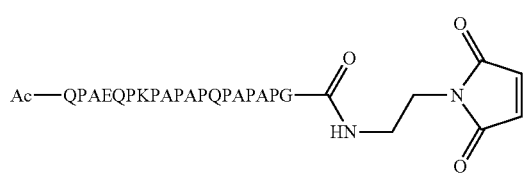

(7)

Maleimidopeptide 7 was synthesized and purified as described above for maleimidopeptide 2. ESI MS: MW calculated for C$_{91}$H$_{137}$N$_{25}$O$_{27}$: 2012.0 Da. MW found: 2012.4 Da (±0.05%).

Maleimidopeptide 8

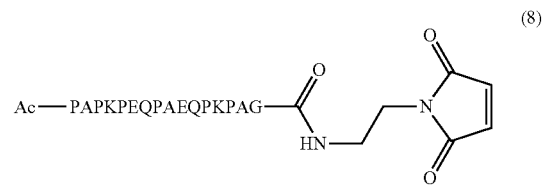

(8)

Maleimidopeptide 8 was synthesized and purified as described above for maleimidopeptide 2. ESI-MS: MW calculated for C$_{81}$H$_{124}$N$_{22}$O$_{25}$: 1804.9 Da. MW found: 1805.4 Da (±0.05%).

Maleimidopeptide 9

(9)

This maleimidopeptide is derived from the PR peptide of PhtD (P60, SEQ ID NO:86). The N-terminus is acetylated. The maleimidopeptide was synthesized and purified as described above for maleimidopeptide 2 and analyzed by analytical RP-HPLC using an Agilent XDB-C18 column (250×4.6 mm) and a linear gradient of 20-100% MeCN in H$_2$O (+0.1% TFA) in 25 min: Purity>97%; t$_R$=3.41 min. ESI-MS: MW calculated for C$_{136}$H$_{201}$N$_{37}$O$_{48}$: 3120.4 Da. MW found: 3120.6 Da (±0.05%).

Example 2

Conjugation of PR Peptide Antigens to Lipopeptides

In order to prepare lipopeptide conjugates for immunizations the following four lipopeptide building blocks were synthesized.

Lipopeptide Building Block 10

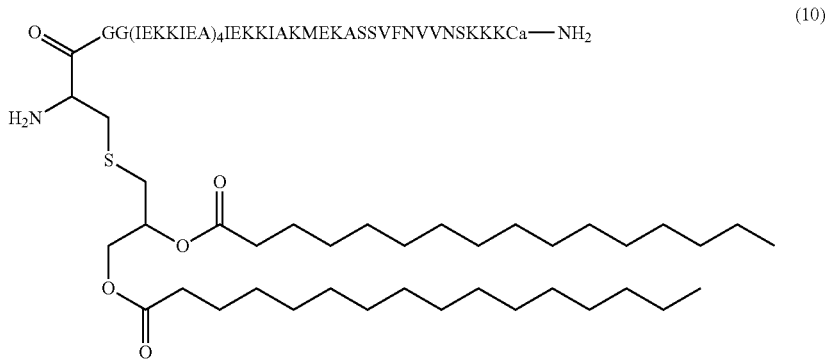

This lipopeptide corresponds to Example 13 in WO 2008/068017. The synthesis was carried out and the product was characterized as described in WO 2008/068017 and Ghasparian, Riedel et al., *Chembiochem,* 2011, 12, 100-109. Analytical RP-HPLC (Interchrom UP5WC4-25QS, 25 to 100% MeCN in $H_2O$ (+0.1% TFA) over 25 min.): Purity>96%, $t_R$=22.71 min. MALDI-TOF: MW calculated for $C_{312}H_{552}N_{74}O_{85}S_3$: 6796.4 Da. MW found: 6798.2 Da (±0.05%).

Lipopeptide Building Block 11

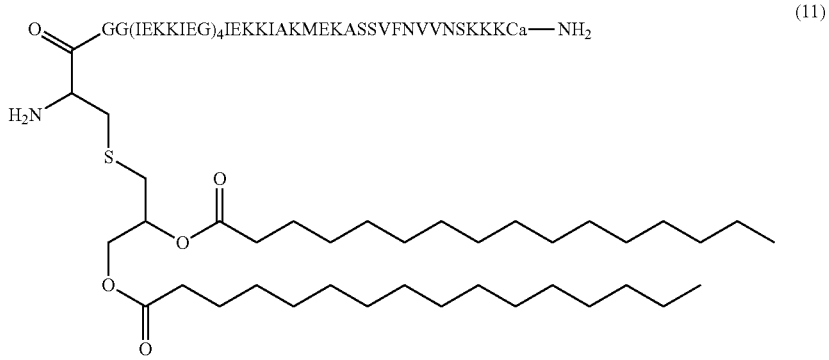

This lipopeptide building block contains a modified coiled-coil domain, which has Gly in the "c" positions of the heptad repeat "defgabc" IEKKIEG (SEQ ID NO:125).

The modified lipopeptide building block was synthesized and purified as described in WO 2008/068017. Analytical RP-HPLC (Interchrom UP5WC4-25QS, 25 to 100% MeCN in $H_2O$ (+0.1% TFA) over 25 min.): Purity>98%, $t_R$=21.41 min. ESI-MS: MW calc. for $C_{308}H_{544}N_{74}O_{85}S_3$ 6740.3 Da. found 6741.7 Da.

Lipopeptide Building Block 12

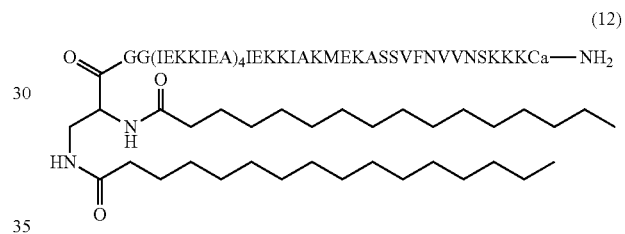

This lipopeptide building block contains a modified lipid N,N'-dipalmitoyl.-2,3-diamino-propionamide ("Pam$_2$Dap"). "a" denotes D-alanine.

The lipopeptide building block was synthesized and purified as described in WO 2008/068017, except that Pam2Dap was incorporated at the end of the synthesis instead of Pam2Cys. The lipopeptide was analyzed by analytical HPLC and MS.

Analytical RP-HPLC (C4 column, A=$H_2O$+0.1% TFA, B=MeCN+0.1% TFA, 20 to 100% B in 25 min.): Purity: >95%. $t_R$=22.1 min. ESI-MS: MW calc. 9594.5 Da. found 9596.17 Da.

Lipopeptide Building Block 13

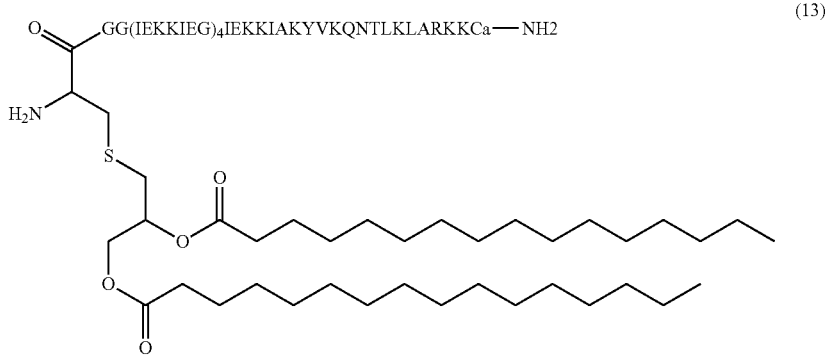

(13)

This lipopeptide building block contains a promiscuous T-helper epitope (KYVKQNTLKLARK, SEQ ID NO:126) derived from a HLA-DRB 101 restricted epitope from Influenza hemagglutinin residues 307-309 (SEQ ID NO:19) (Stern, L J. et al. *Nature* 1994, 368, 215). "a" denotes D-alanine.

The lipopeptide building block was synthesized and purified essentially as described in WO 2008/068017 and analyzed by analytical HPLC and MS. Analytical RP-HPLC (C4 column, A=$H_2O$+0.1% TFA, B=MeCN+0.1% TFA, 20 to 100% B in 25 min.): Purity: >95%. $t_R$=22.35 min. ESI-MS: MW calc. for $C_{302}H_{538}N_{74}O_{79}S_2$: 6530.0 Da. found 6530.4 Da (±0.05%).

The following conjugates were synthesized:
Conjugate 14 (Maleimidopeptide 1+Lipopeptide 10)

was carefully adjusted and maintained at pH 6.5-7.0 with 0.1 NaOH, and the mixture was stirred for 2 h at room temperature. The conjugate was then purified by RP-HPLC using a C4 preparative column (Interchrom UP5WC4-25M, 250×10 mm) and a gradient of 50 to 100% MeCN in $H_2O$ (+0.1% TFA) in 17 min. The conjugate 14 was analyzed by analytical RP-HPLC using an Interchrom UP5WC4-25QS column (250×4.6 mm) and a gradient of 20 to 100% MeCN in $H_2O$ (+0.1% TFA) in 25 min: Purity>97%; $t_R$=22.34 min. MALDI-TOF MS: MW calc. $C_{475}H_{811}N_{115}O_{136}S_3$: 10406.6 Da. found 10407.8 Da (±0.1%).

The conjugate was suspended in PBS, equilibrated for 30 min., diluted to 0.5 mg/ml and analyzed by Dynamic Light Scattering (DLS) on a Wyatt DynaPro Titan instrument at 4° C., 25° C. and 37° C. using a laser intensity of 400,000 counts/s and an acquisition time of 10 s. The size distribution

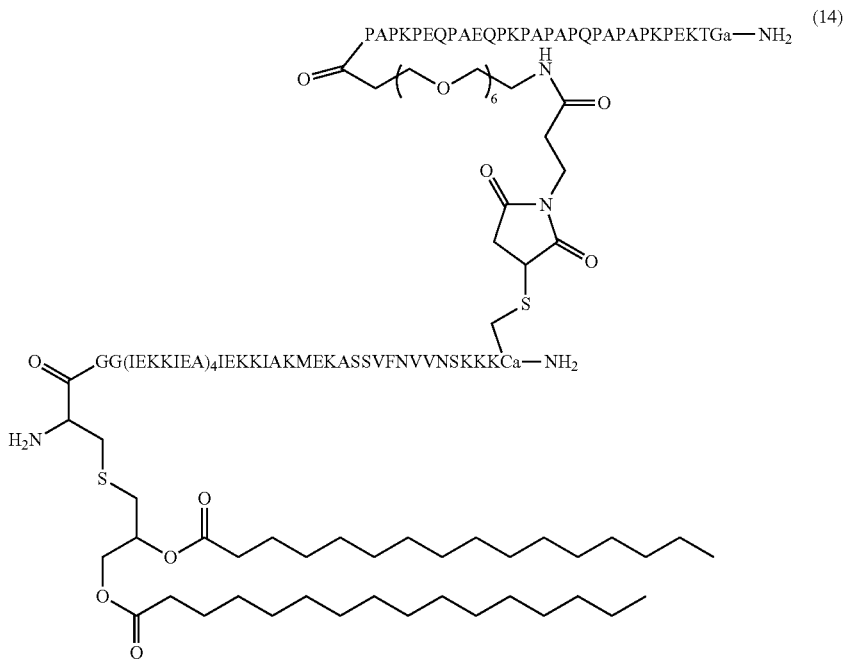

(14)

The conjugation of 1 to 10 was performed essentially as described in WO 2008/068017. To a solution of 10 (6.0 mg, 0.9 μmol) in $H_2O$/MeCN 1:1 (3 ml) was added a solution of 1 (4.8 mg, 1.3 μmol) in $H_2O$/MeCN 1:1 (2.4 ml). The pH by regularization analysis was monomodal and the size dispersity was small. The mean hydrodynamic radius ($R_h$) was 12.0 nm, and % Pd value 12.3% at 25° C. Similar values for $R_h$ and % Pd were obtained at other temperatures.

Conjugate 15 (Maleimidopeptide 2+Lipopeptide 10)

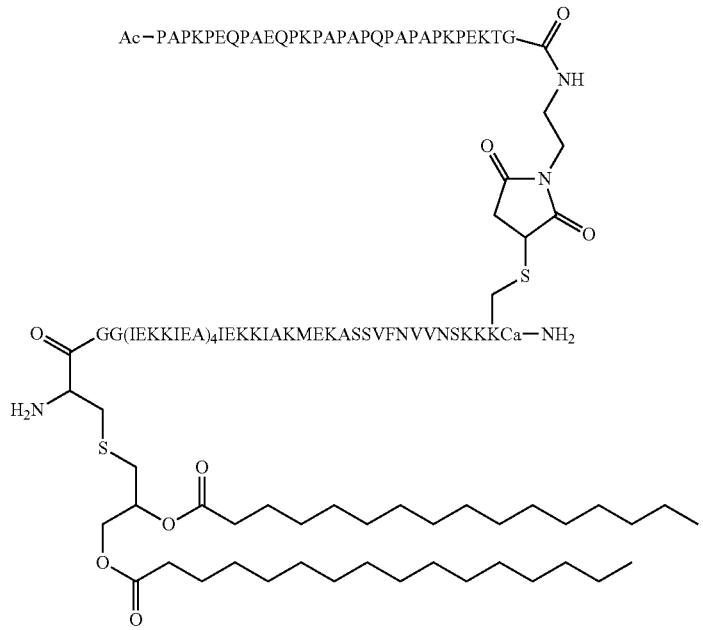

(15)

The conjugation of 2 to 10 and purification of the conjugate was performed essentially as described above for conjugate 14. Product 15 was analyzed by analytical RP-HPLC using an Interchrom UP5WC4-25QS column (250× 4.6 mm) and a gradient of 20 to 100% MeCN in $H_2O$ (+0.1% TFA) in 25 min: Purity>97%; $t_R$=22.41 min. ESI-MS: MW calc. for $C_{458}H_{779}N_{113}O_{128}S_3$: 10012.9 Da. found 10011.1 Da (±0.1%).

A suspension of conjugate 12 in PBS was prepared and analyzed using DLS as described above for 14. $R_h$ values were in the range of 13.2-14.2 nm, and % Pd values in the range of 12.6-18.0% at 25° C.

Conjugate 16 (Maleimidopeptide 3+Lipopeptide 10)

The conjugation of 3 to 10 and purification of the conjugate was performed essentially as described above for conjugate 14. Product 16 was analyzed by analytical RP-HPLC using an Interchrom UP5WC4-25QS column (250× 4.6 mm) and a gradient of 20 to 100% MeCN in $H_2O$ (+0.1% TFA) in 25 min: Purity>97%; $t_R$=22.0 min. MALDI-TOF MS: MW calc. for $C_{475}H_{811}N_{115}O_{136}S_3$: 10869.8 Da. found 10,872.3 Da (±0.1%).

A suspension of conjugate 13 in PBS was prepared and analyzed using DLS as described above for 14. $R_h$ values were in the range of 14.0-15.0 nm, and % Pd values in the range of 13.0-13.7%. DLS analysis of a mixture of Conjugate 14 and Conjugate 16 particles yielded an $R_h$ of 12.3-13.3 nm and a % Pd values around 25-26%, indicating that mixing the particles did not alter the overall size distribution.

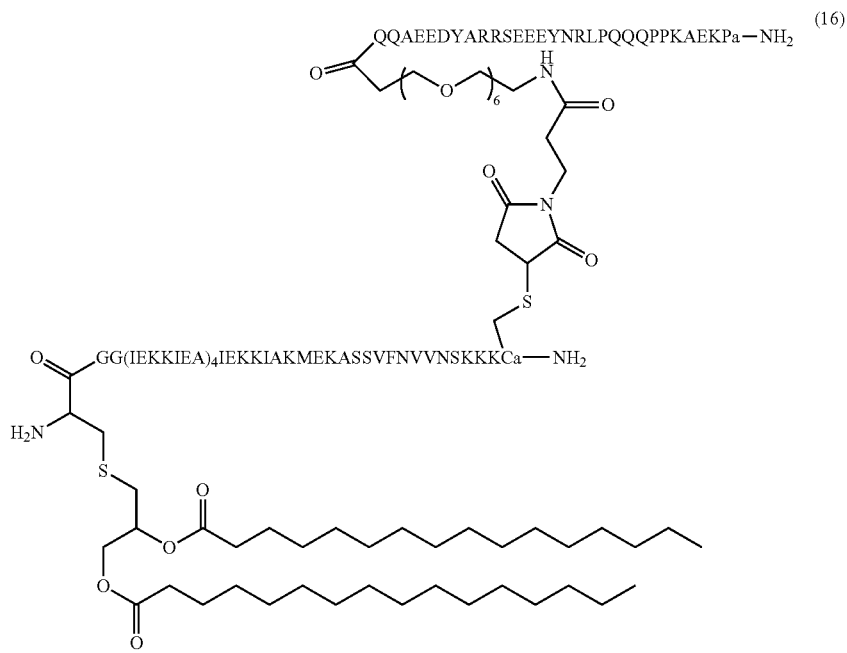

(16)

Conjugate 17 (Maleimidopeptide 4+Lipopeptide 14)

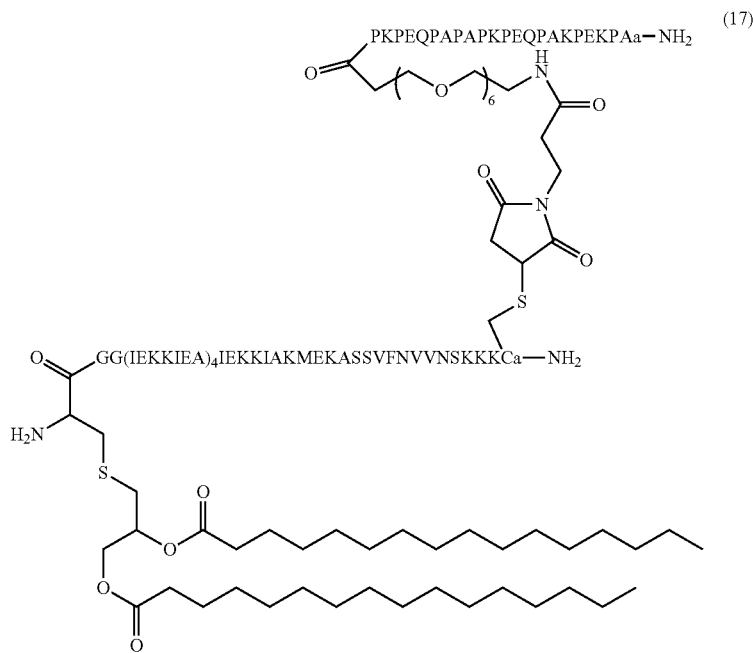

The conjugation of 4 to 10 and purification of the conjugate was performed essentially as described above for conjugate 17. Product 17 was analyzed by reversed phase HPLC on a C4 analytical column (Interchrom, UP5WC4-25QS, 4.6 mm×250 mm, 300 Å) and by MALDI-MS. Analytical RP-HPLC (C4 column, A=$H_2O$+0.1% TFA, B=MeCN+0.1% TFA, 20 to 100% B in 25 min.): Purity: >95%. $t_R$=18.8 min. MALDI-TOF MS: MW calc. for $C_{443}H_{762}N_{106}O_{126}S_3$: 9685.6 Da. found 9686.2 Da (±0.1%).

A suspension of conjugate 17 in PBS was prepared and analyzed using DLS as described above for 14. $R_h$ values were in the range of 11.1-11.8 nm and % Pd values around 13%.

Conjugate 18 (Maleimidopeptide 5+Lipopeptide 10)

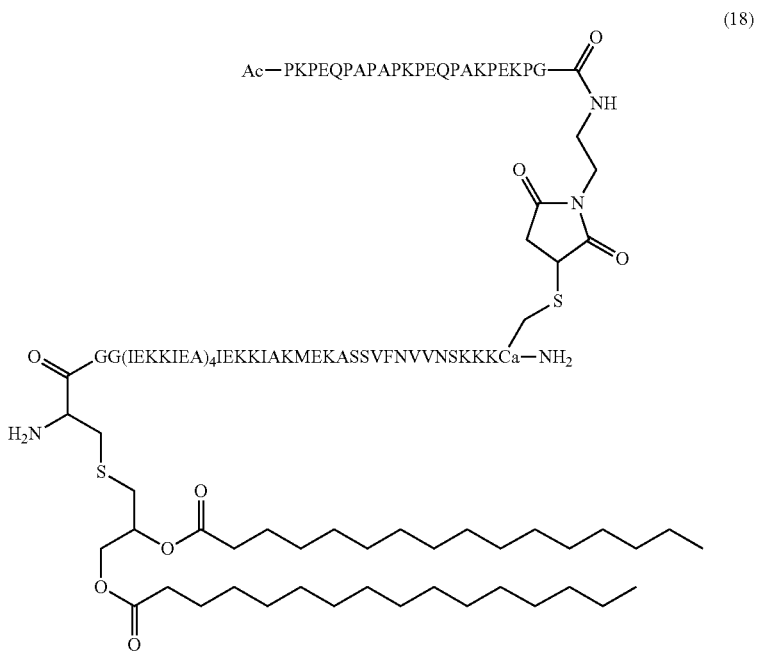

The conjugation of 5 to 10 and purification of the conjugate was performed essentially as described above for conjugate 18. Product 18 was analyzed by reversed phase HPLC on a C4 analytical column (Interchrom, UP5WC4-25QS, 4.6 mm×250 mm, 300 Å) and by MALDI-MS. Analytical RP-HPLC (C4 column, A=$H_2O$+0.1% TFA, B=MeCN+0.1% TFA, 20 to 100% B in 25 min.): Purity: >96%. $t_R$=22.55 min. MALDI-TOF MS: MW calc. for $C_{425}H_{728}N_{104}O_{118}S_3$: 9279.2 Da. found 9280.2 Da (±0.1%).

A suspension of conjugate 18 in PBS was prepared and analyzed using DLS as described above for 14. $R_h$ values were in the range of 10.0-10.5 nm and % Pd values around 16%.

Conjugate 19 (Maleimidopeptide 6+Lipopeptide 10)

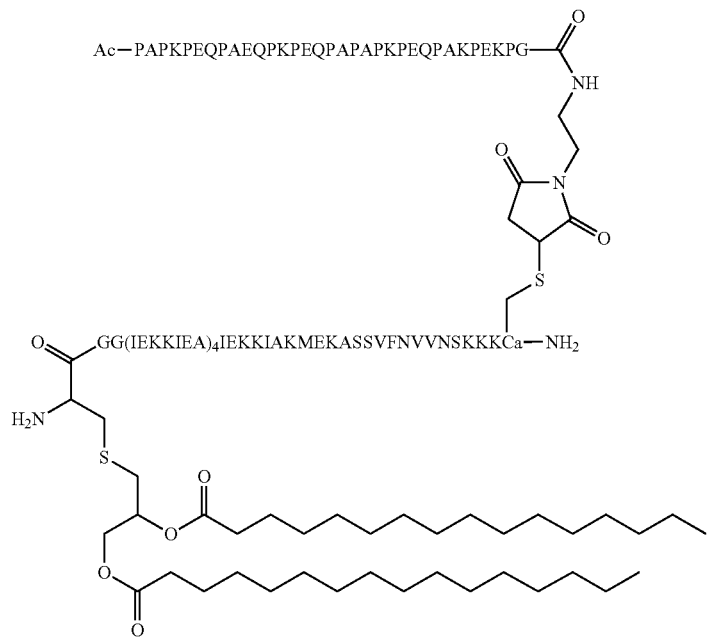

(19)

The conjugation of 6 to 10 and purification of the conjugate was performed essentially as described above for conjugate 14. Product 19 was analyzed by reversed phase HPLC on a C4 analytical column (Interchrom, UP5WC4-25QS, 4.6 mm×250 mm, 300 Å) and by MALDI-MS. Analytical RP-HPLC (C4 column, A=$H_2O$+0.1% TFA, B=MeCN+0.1% TFA, 20 to 100% B in 25 min.): Purity: >96%. $t_R$=22.34 min. MALDI-TOF MS: MW calc. for $C_{476}H_{807}N_{119}O_{135}S_3$: 10453.4 Da. found 10452.7 Da (±0.1%).

A suspension of conjugate 17 in PBS was prepared and analyzed using DLS as described above for 19. $R_h$ values were in the range of 12.1-14.5 nm and % Pd values 12-20%.

Conjugate 20 (Maleimidopeptide 6+Lipopeptide 11)

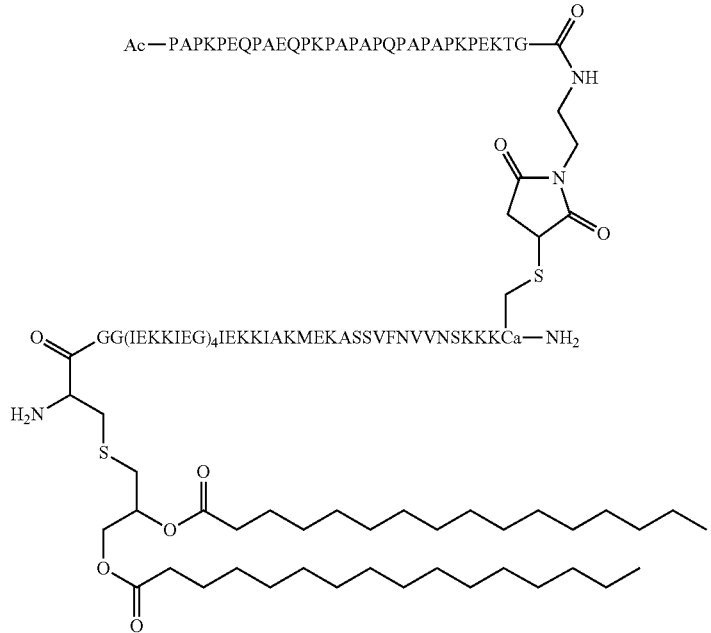

The conjugation of 6 to 11 and purification of the conjugate was performed essentially as described above for conjugate 14. Product 20 was analyzed by reversed phase HPLC on a C4 analytical column (Interchrom, UP5WC4-25QS, 4.6 mm×250 mm, 300 Å) and by MALDI-MS. Analytical RP-HPLC (C4 column, A=$H_2O$+0.1% TFA, B=MeCN+0.1% TFA, 20 to 100% B in 25 min.): Purity: >98%. $t_R$=22.34 min. ESI-MS: MW calc. for $C_{454}H_{773}N_{113}O_{129}S_3$ (succinimide ring hydrolysis): 9975.02 Da. found 9974.7 Da (±0.01%).

A suspension of conjugate 20 in PBS was prepared and analyzed using DLS as described above for 14. $R_h$ values were in the range of 11.7-12.3 nm and % Pd values around 20%.

Conjugate 21 (Maleimidopeptide 4+Lipopeptide 11)

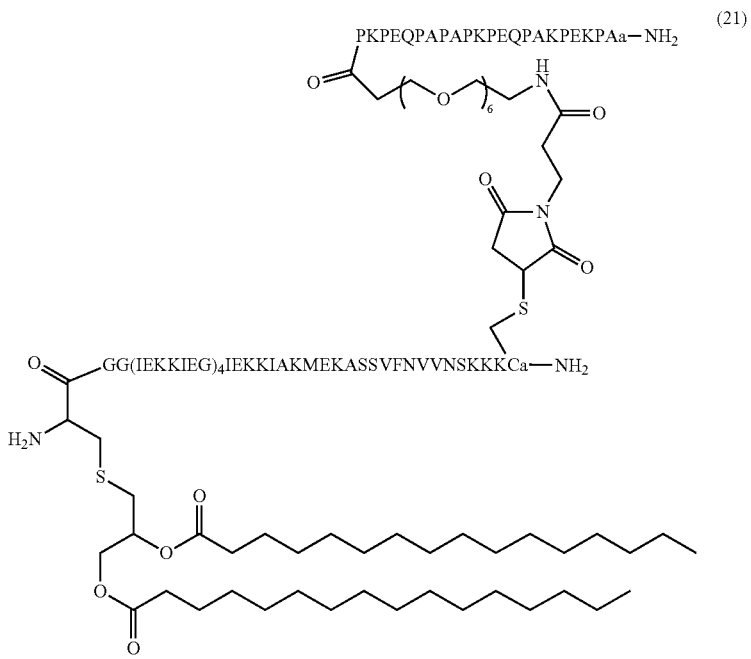

Maleimidopeptide 4 was conjugated to 11 and the conjugate was purified as described above for conjugate 14. Analytical RP-HPLC (C4 column, A=H$_2$O+0.1% TFA, B=MeCN+0.1% TFA, 20 to 100% B in 25 min.): Purity: >95%. $t_R$=17.78 min. MW calc. for C$_{439}$H$_{753}$N$_{105}$O$_{127}$S$_3$: 9630.5 Da. found 9631.2 Da.

DLS (0.5 mg/ml in PBS, 25° C.): R$_h$=10.7 nm; % Pd=12-13%.

Conjugate 22 (Maleimidopeptide 6+Lipopeptide 12)

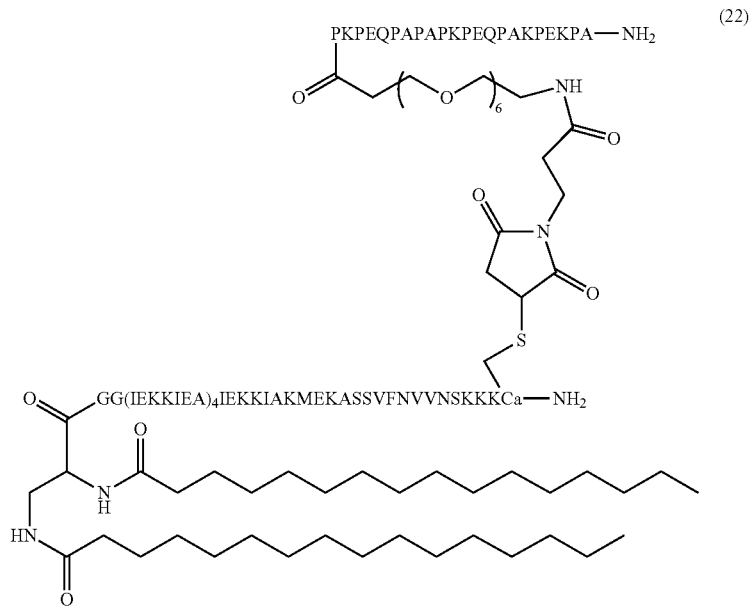

(22)

The maleimido peptide 4 was conjugated to 12 and the conjugate was purified as described above for conjugate 14. Analytical RP-HPLC (C4 column, A=H$_2$O+0.1% TFA, B=MeCN+0.1% TFA, 20 to 100% B in 25 min.): Purity: >95%. $t_R$=18.37 min. MALDI-TOF: MW calc. for C$_{440}$H$_{757}$N$_{107}$O$_{124}$S$_2$: 9594.5 Da. found 9595.1 (±0.1%) Da.

DLS measurements (0.5 mg in PBS, 25°) yielded R$_h$ of 10.4-11.1 nm and % Pd values of 10-12%.

Conjugate 23 (Maleimidopeptide 6+Lipopeptide 13)

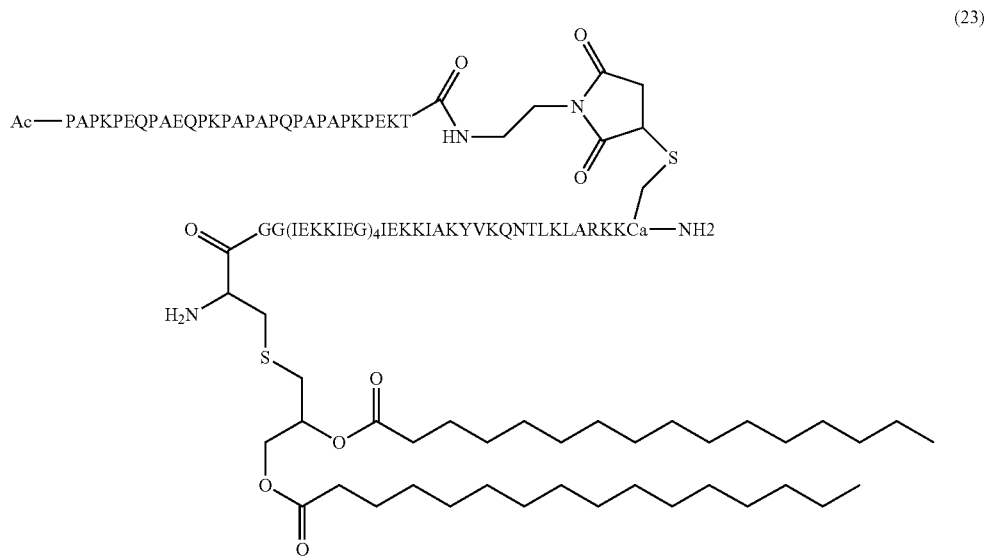

(23)

The maleimido peptide 6 was conjugated to 13 and the conjugate was purified as described above for conjugate 14. Analytical RP-HPLC (C4 column, A=H$_2$O+0.1% TFA, B=MeCN+0.1% TFA, 20 to 100% B in 25 min.): Purity: >95%. $t_R$=18.25 min. MALDI-TOF: MW calc. for C$_{448}$H$_{765}$N$_{113}$O$_{123}$S$_2$ (succinimide ring hydrolysis): 9768.7 Da. found 9767.0 Da (±0.1%).

DLS measurements (0.5 mg in PBS, 25°) yielded R$_h$ of 9.9-10.2 nm and % Pd values of 15-18%.

Additional Lipopeptides were prepared by fusing the N-terminus of the PR peptide antigen to the C-terminus of the lipopeptide building block. The following fusion lipopeptides were prepared.

Lipopeptide (24)

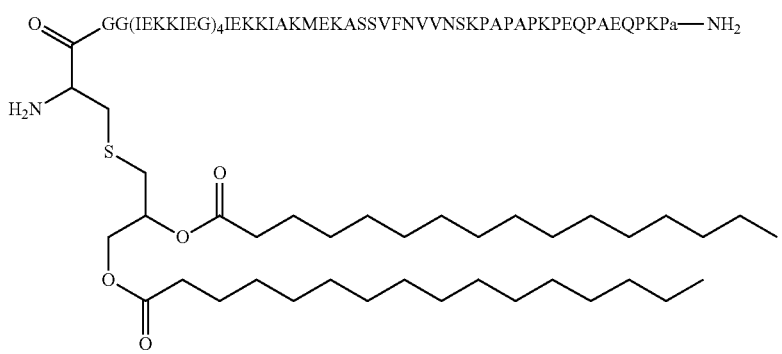

(24)

In this example the PR sequence P7, PAPAPKPEQ-PAEQPKP (SEQ ID NO: 33) was fused directly to the C-terminus of GG(IEKKIEG)$_4$IEKKIAKMEKASSVFN-WNSK (SEQ ID NO: 127) to yield the sequence GG(IEK-KIEG)$_4$IEKKIAKMEKASSVFNVVNSKPAPAPKPEQ-PAEQPKP (SEQ ID NO: 128). The N-terminus was lipidated by addition of Pam2Cys and D-alanine ("a") was added to the C-terminus in lipopeptide 24.

The fusion lipopeptide 24 was synthesized using conventional solid-phase peptide synthesis methods (W. C. Chan, P. D. White, Fmoc Solid Phase Peptide Synthesis: A Practical Approach, Oxford University Press, Oxford, U K, 2000) and purified as described above for lipopeptide 10. MALDI-TOF MS: MW calc. for C$_{369}$H$_{633}$N$_{89}$O$_{104}$S$_2$: 8044.6 Da. found: 8044.6 Da (±0.1%). Analytical RP-HPLC (Interchrom UP5WC4-25QS, 25 to 100% MeCN in H$_2$O (+0.1% TFA) over 25 min.): Purity>98%, $t_R$=20.48 min.

DLS (0.5 mg/ml in PBS, 25° C.): R$_h$=10.7 nm; % Pd=12-13%.

Lipopeptide (25)

In this example the PR sequence P7, PAPAPKPEQ-PAEQPKP (SEQ ID NO: 33) was fused directly to the C-terminus of GG(IEKKIEG)$_4$IEKKIAKYVKQNTLKLAR (SEQ ID NO: 129) to yield the sequence GG(IEKKIEG)$_4$ IEKKIAKMEKASSVFNVVNSKPAPAPKPEQPAEQPKP (SEQ ID NO: 130). The N-terminus was lipidated by addition of Pam2Cys and D-alanine ("a") was added to the C-terminus in lipopeptide 25.

The fusion lipopeptide 25 was synthesized and purified as described above for 24. ESI-MS: MW calc. for C$_{360}$H$_{639}$N$_{91}$O$_{99}$S: 7966.6 Da. found: 7967.0 Da (±0.1%).

Analytical RP-HPLC (Interchrom UP5WC4-25QS, 25 to 100% MeCN in H$_2$O (+0.1% TFA) over 25 min.): Purity>98%, $t_R$=21.41 min.

DLS (0.5 mg/ml in PBS, 25° C.): R$_h$=12.2-13.7 nm; % Pd=10-15%.

Example 3

Preparation of Controls

The following control compounds were prepared for immunizations and challenge experiments.

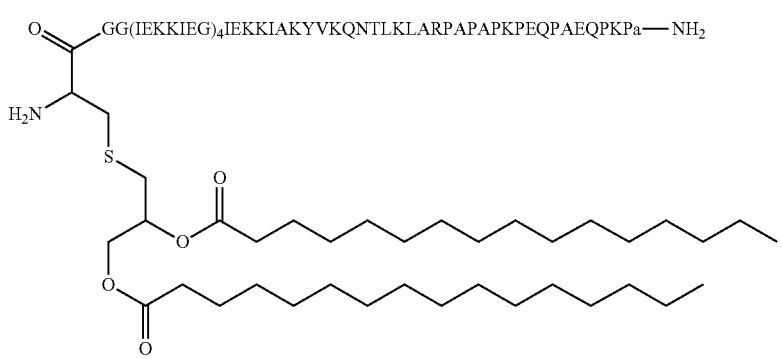

(25)

Conjugate 26 (Non PR Conjugate)

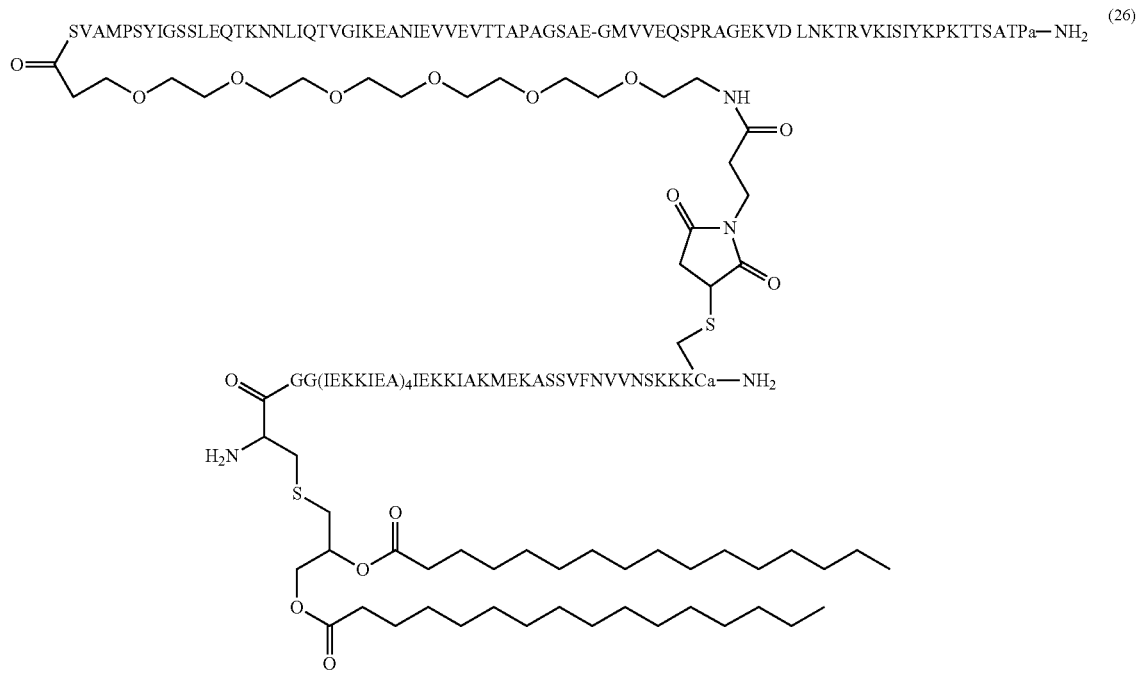

(26)

This conjugate contains the C-terminal part (StkP-C; PASTA+C-terminus) of StkP (SEQ ID NO: 115), except that 2 mutations (F594Q and I602T) were incorporated into the StkP sequence to remove surface-exposed hydrophobic residues, resulting in sequence SVAMPSYIGSSLEQTKNNLIQTVGIKEANIEWEVTTAPAGSAEGMVVEQSPRAGEKVDL NKTRVKISIYKPKTTSATP (SEQ ID NO: 131). The C-terminus was blocked with a-NH2, where "a" denotes D-alanine. This StkP peptide in the conjugate adopts a regular Penicillin-binding protein and Ser/Thr kinase Associated (PASTA) domain-structure by NMR.

The corresponding maleimidopeptide 27 (3-maleimidopropionyl)-21-amino-4,7,10,13,16,19-hexaoxaheneicosanoyl-(SEQ ID NO: 131)-a-NH$_2$) was synthesized and conjugated to 10 as described above for 14. Conjugate 26 was analyzed by HPLC, MALDI-MS and DLS. Analytical RP-HPLC (Interchrom UP5WC4-25QS, 250×4.6 mm, A=H$_2$O+0.1% TFA, B=MeCN+0.1% TFA, 20 to 100% B in 25 min.): Purity: >95%. t$_R$=18.41 min. MALDI-TOF: MW calc. for C$_{700}$H$_{1201}$N$_{177}$O$_{216}$S$_5$: 15713.41 Da. found 15715.4 Da (±0.1%). DLS (0.5 mg/ml in PBS, 25° C.): R$_h$=16.3 nm, % Pd=16.9%.

Lipopeptide 28

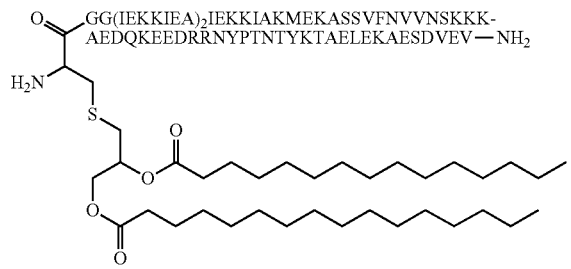

(28)

In this lipopeptide the 31 amino acids at the C terminus correspond to amino acids 344 to 377 from PspC of TIGR4 (SEQ ID NO: 116), except that two mutations were incorporated into the antigen to improve solubility (L366A, I370K; TIGR4 PspC numbering), resulting in peptide AEDQKEEDRRNYPTNTYKTAELEKAESDVEV (SEQ ID NO: 132). The C-terminus was blocked with r-NH2, where "r" denotes D-arginine. This peptide is further coupled through a short linker (KKK) to the universal T-helper cell epitope CST.3* (SEQ ID NO: 23).

Lipopeptide 28 was synthesized and purified as described in WO 2008/068017, and was analyzed by HPLC, MALDI-MS and DLS. Analytical RP-HPLC (Interchrom UP5WC4-25QS, 250×4.6 mm, A=H$_2$O+0.1% TFA, B=MeCN+0.1% TFA, 20 to 100% B in 25 min.): Purity: >95%. t$_R$=18.41 min. MALDI-TOF: MW calc. for C$_{386}$H$_{654}$N$_{100}$O$_{121}$S$_2$: 8696.1 Da. found 8696.0 Da. DLS (0.5 mg/ml in PBS, 25° C.): R$_h$=7.9 nm; % Pd=29%.

Recombinant PspA Protein (rPspA)

The proline-rich region of the PspA from *S. pneumoniae* strain SP1577 was cloned and expressed as recombinant Trx fusion protein (rPspA). Cloning and expression of recombinant PR from the SP1577 strain was performed as described in WO 2007/089866. The purity and identity were confirmed by SDS-PAGE, dot-blot using anti-PspA antibodies and mass spectrometry. The sequence of the protein is:

```
                                          (SEQ ID NO: 133)
MSDKIIHLTD DSFDTDVLKA DGAILVDFWA EWCGPCKMIA

PILDEIADEY QGKLTVAKLN IDQNPGTAPK YGIRGIPTLL

LFKNGEVAAT KVGALSKGQL KEFLDANLAG SGSGHMHHHH

HHSSGLVPRG SGMKETAAAK FERQHMDSPD LGTDDDDKAM

ADLKKAVNEP EKPAEETPAP APKPEQPAEQ PKPAPAPQPA
```

-continued

*PAPKPEKTDD QQAEEDYARR SEEEYNRLPQ QQPPKAEKPA*

*PAPKPEQPVP APKPEQPVPA PKTGWKQE*

PspA proline-rich region including non-proline block are shown in italics.

Example 4

Mouse Immunization Studies

Conjugates were tested for immunogenicity against *S. pneumoniae* in mice. All experiments were performed in accordance with the Swiss rules and regulations for the protection of animal rights and have been approved by the responsible authorities.

For analysis of the antibody response outbred six to eight week-old female NMRI outbred mice (10 per group) were subcutaneously immunized two times in three-week intervals on days 0 and 21 with 0.1 ml of the formulations shown in Table 4. Control animals were immunized with PBS or rPspA+alum in saline. Blood was collected before the first and ten days after the second immunization and sera were analyzed using ELISA to determine titers of IgG antibodies to the proline-rich peptide, Western Blot to determine IgG to endogenous proteins and flow cytometry to determine surface binding of IgG to intact *pneumococci*.

TABLE 4

Formulations used for immunizations of mice

| Formulation | Adjuvant | Concentration (mg/ml)[a] |
|---|---|---|
| 14 in PBS | None | 0.2 |
| 15 in PBS | None | 0.2 |
| 16 in PBS | None | 0.2 |
| 17 in PBS | None | 0.2 |
| 18 in PBS | None | 0.2 |
| 19 in PBS | None | 0.2 |
| 16 + 14 in PBS | None | 0.2 + 0.2 |
| rPspA in saline | Alum | 0.2 |
| PBS | None | — |

[a] Shown is the overall lipopeptide conjugate/protein concentration.

For ELISA, MaxiSorp 96-well microtitre plates (Nunc, Fischer Scientific) were coated at 4° C. overnight with 5 µl/ml solutions of PR peptides or rPspA in PBS, pH 7.2 (50 µl/well). The ELISA was performed essentially as described in WO 2008/068017, using goat anti-mouse IgG (γ-chain-specific) antibodies (Sigma, St. Louis, Mo.) and 1 mg/ml p-nitrophenyl phosphate (Sigma) for IgG detection. Endpoint titers were defined as the highest serum dilution for which the OD of the test sera was larger than the mean OD of PBS plus two SD.

For Western Blot analysis of immune sera, SP1577 was cultured in blood agar plates at 37° C., 5% $CO_2$ and total bacterial lysates were prepared. Lysates were separated by SDS-PAGE under reducing conditions and blotted onto nitrocellulose membranes. Blots were incubated with immune or pre-immune sera (1:500 in PBS) and developed using the ECL system. A PspA-specific monoclonal antibody was used as positive control.

For flow-cytometry analysis (FACS), SP1577 was cultured as described above, inactivated with formalin for 30 min., blocked with 5 mg/ml fatty-acid-free BSA in PBS and approximately $7 \times 10^5$ CFU were incubated with immune or pre-immune sera (1:100 in PBS) for 1 h at room temperature. Surface-bound IgG was detected using an Alexafluor 488-conjugated secondary antibody.

ELISA Geometric Mean Endpoint titers (GMT)±one Standard Deviation of the Mean (SEM) and results from the Western Blot and FACS analyses (as positive vs. negative reactivity) are summarized in Table 5.

TABLE 5

IgG Response in mice after two immunizations

| Immunogen | ELISA (GMT ± SEM)[a] | Western Blot (Pos./Neg.) | FACS (Pos./Neg.) |
|---|---|---|---|
| 14 | 26013 ± 30255 | 9/1 | 8/2 |
| 15 | 271227 ± 82014 | 10/0 | 10/0 |
| 16 | 65606 ± 13592 | 10/0 | 10/0 |
| 17 | 82066 ± 36672 | 8/2 | 6/4 |
| 18 | 10354 ± 6760 | 7/3 | 5/5 |
| 19 | 263069 ± 62452 | 7/3 | 7/3 |
| 14 + 16[a] | 9027 ± 6150 | 10/0 | 10/0 |
| 14 + 16[b] | 65606 ± 13592 | 10/0 | 10/0 |
| rPspA + alum | 212977 ± 65684 | 10/0 | 10/0 |
| PBS | <100 | 0/10 | 0/10 |

[a] Pre-immune sera showed no significant reactivity in ELISA, Western Blots and FACS.
[b] IgG response measured in ELISA against 14
[c] IgG response measured in ELISA against 16

Although the antibody response was variable in the outbred mice, all mice developed high titers of antigen-specific IgG as measured in ELISA and IgG in most of the immune sera bound to endogenous PspA and to intact SP1577 cells. No significant levels of antigen-specific IgG could be detected in pre-immune sera and in sera from PBS-immunized mice.

The cross-reactivity of the elicited IgG to was assessed using Western Blot and FACS and a panel of genetically diverse pneumococcal strains representing different PspA belonging to different clades from PspA families 1-3, which are defined in Hollingshead, Becker et al., *Infect Immun*, 2000, 68, 5889-5900, and different pneumococcal capsular serotypes, including serotypes that are not covered by the currently licensed pneumococcal conjugate vaccines.

Bacteria were cultured and Western Blot and FACS analyses were performed with sera from immunized mice as described above for SP1577. The results are summarized below in Table 6.

TABLE 6

Cross-reactivity of IgG in mouse sera with genetically diverse *Pneumococci*

| Immunogen | Test [a] | SP1577/1 | SP920/8 | SP4408/19A | SP1272/2 | SP1388/4 | SP1260/4 | SP716/5 |
|---|---|---|---|---|---|---|---|---|
| 14 | WBA | ++ | + | + | ++ | + | + | ++ |
|  | FACS | ++ | + | ++ | ++ | + | ++ | ++ |
| 15 | WBA | ++ | ++ | ++ | ++ | + | ++ | ++ |

TABLE 6-continued

Cross-reactivity of IgG in mouse sera with genetically diverse *Pneumococci*

| Immunogen | Test[a] | SP1577/1 | SP920/8 | SP4408/19A | SP1272/2 | SP1388/4 | SP1260/4 | SP716/5 |
|---|---|---|---|---|---|---|---|---|
| 16 | FACS | ++ | + | ++ | + | + | ++ | ++ |
|  | WBA | ++ | ++ | + | ++ | ++ | ++ | ++ |
| 17 | FACS | ++ | ++ | ++ | ++ | ++ | ++ | ++ |
|  | WBA | ++ | − | − | + | ++ | − | − |
| 18 | FACS | ++ | ++ | ++ | ++ | ++ | − | − |
|  | WBA | ++ | − | − | + | ++ | − | − |
| 19 | FACS | ++ | ++ | ++ | ++ | ++ | − | − |
|  | WBA | + | − | − | + | ++ | − | + |
| 14 + 16 | FACS | + | + | ++ | ++ | ++ | ++ | ++ |
|  | WBA | ++ | ++ | ++ | ++ | ++ | ++ | ++ |
| rPspA + alum | FACS | ++ | ++ | ++ | ++ | ++ | ++ | ++ |
|  | WBA | ++ | ++ | ++ | ++ | ++ | ++ | ++ |
|  | FACS | ++ | ++ | ++ | ++ | ++ | ++ | ++ |

[a] Sera after two immunizations were used.
Pre-immune sera showed no reactivity in the assays.
++ = strong band/signal; + = weak band/signal; − = no binding could be detected.

The results obtained with the genetically diverse panel indicates that immunization with PR peptide antigens elicited broadly cross-reactive IgG, although some PR peptide antigen constructs elicited more broadly cross-reactive IgG than others.

For challenge studies NMRI outbred mice were immunized with different formulations as described above. For comparison of the immunogenicity additional animals were immunized with rPspA+alum, conjugate 44 or lipopeptide 46. The mice were bled 10 days after the final immunization, sera were analyzed by ELISA as described above in order to determine seroconversion. The mice were then challenged intravenously (iv) via the tail vein with 100 times of a pre-determined lethal dose (100×LD$_{100}$) *pneumococci*, which were rendered highly virulent by passage in mice prior to the challenge. Bacteria were either passaged by intraperitoneal (ip) or intravenous (iv) injection. After challenge, the health status of the mice was monitored over 14 days. Moribund animals were euthanized and the time to moribund was recorded. The survival and time to moribund of the animals immunized with lipopeptides or the protein were compared to that of animals immunized with PBS alone.

Results obtained with strain SP1577 are summarized in below in Table 7. The SP1577 strain is highly virulent in mice. Unprotected mice died or became moribund within the first 12-24 h after challenge. Protection, therefore, indicates high efficacy.

TABLE 7

Protection of NMRI mice from lethal challenge with strain SP1577

| Formulation | Passage | Days to moribund Test | Control (PBS) | P-value for survival[b] |
|---|---|---|---|---|
| 14 in PBS | ip | 1, 2, 3 x >14 | 5 × 1 | 0.0143 |
| 14 in PBS | iv | 2 × 1, 5, 2 x >14 | 5 × 1 | 0.0495 |
| 15 in PBS | ip | 1, 2, 3, 2 x >14 | 5 × 1 | 0.0143 |
| 15 in PBS | iv | 3 × 2, 2 x >14 | 5 × 1 | 0.0027 |
| 16 + 14 in PBS | ip | 1, 1.5, 4, 2 x >14 | 5 × 1 | 0.0143 |
| 16 + 14 in PBS | iv | 3 × 2, 6, 14 | 5 × 1 | 0.0027 |
| 18 in PBS | ip | 1, 1.5, 3 x >14 | 5 × 1 | 0.0143 |
| 19 in PBS | ip | 2 × 2, 3 x >14 | 5 × 1 | 0.0027 |
| 17 + 26 + 28 in PBS | ip | 2 × 1, 3 x >14 | 5 × 1 | 0.0495 |
| rPspA + alum | ip | 3 × 1, 2 x >14 | 5 × 1 | NS |
| rPspA + alum | iv | 3 × 1, 5, >14 | 5 × 1 | NS |
| 16 in PBS | iv | 5 × 1 | 5 × 1 | NS |
| 26 in PBS | ip | 5 × 1 | 5 × 1 | NS |
| 28 in PBS | ip | 4 × 1, 1 × 3 | 5 × 1 | NS |

[b] Shown is the P-value for the survival distribution compared to the distribution for mice immunized with PBS by Logrank test.
NS = non-significant (P > 0.05).

Mice immunized with PR peptide antigens conjugated to SVLPs were partially protected and the median survival time was prolonged compared to that for PBS immunized mice and mice immunized with rPspA. The survival distributions obtained for mice immunized with SVLPs or rPspA were compared with that for mice immunized with PBS alone (negative control) by the Log-rank test. The results for mice immunized with PR conjugates, alone or in combination with other antigens, were significantly different to those for PBS immunized mice. The P-values were in the range of 0.0027-0.0143. The results for mice immunized with rPspA were not significantly different (P=0.1336) compared to that of PBS immunized mice, although some mice were protected. The difference may become more significant for larger groups. Results for StkP and PspC-derived conjugates were not significant from PBS, indicating that these antigens are not protective in this model.

For passive immunization/challenge experiments to determine if antibodies mediate the protection, monoclonal antibodies were generated in mice. In one experiment BALB/c mice were immunized three times with conjugate 17. Seven B cell hybridoma lines producing antigen-specific monoclonal IgG antibodies (mAbs) were generated from spleen cells of one mouse and tested for cross-reactivity with different pneumococcal strains by FACS analysis. One mAb (5H8) bound to a broad range of strains (clinical isolates) representing different PspA clades and capsular serotypes. Other mAbs bound to the PR antigen in ELISA but not to intact bacteria. Epitope mapping indicated that mAb 5H8 recognized an epitope in the C-terminal part of the PR peptide, which occurs in a broad variety of different PspA sequences, whereas the other 6 mAbs recognized other epitopes, which are less frequently found in different PspA sequences. For the challenge 0.1 to 0.5 mg of purified 5H8 or other mAbs was administered to groups of 5 NMRI mice by iv injection. Animals passively immunized with an StkP-derived mAb (1A7) and naïve animals were used as controls. After sufficient time for equilibration the mice were challenged iv with passaged *pneumococci* and the health status and time to moribund was monitored as described above. Results obtained with strain SP1577 are shown in Table 8 below.

TABLE 8

Passive protection of NMRI mice from lethal challenge with strain SP1577

| Dose (mg/ml) | mAb | Days to moribund Test | Control | P-value for survival[a] |
|---|---|---|---|---|
| 0.5 | 5H8 | 1.5, 2, 3, 2 × >14 | 5 × 1 | 0.0027 |
| 0.1 | 5H8 | 2 × 1, 1 × 1.5, >14 | 5 × 1 | 0.0495 |
| 0.5 | 3H5 | 5 × 1 | 5 × 1 | NS |
| 0.5 | 1H9 | 5 × 1 | 5 × 1 | NS |
| 0.5 | 1A7 | 5 × 1 | 5 × 1 | NS |

[a]Shown is the P-value for the survival distribution compared to the distribution for naïve mice by Logrank test.
NS = non-significant (P > 0.05).

Only mAb 5H8 gave significantly different results after passive immunization, compared to naïve mice. The protection was dose dependent. MAbs 3H5 and 1H9 did not show a significant effect in this model of passive protection. Sequencing revealed that the PspA of strain SP1577 contains only the 5H8 epitope but not the epitopes of the other two PR-derived antibodies. No protection was also seen for the StkP-derived mAb 1A7 in this model.

The results demonstrate that immunization with SVLP-forming lipopeptides carrying proline-rich peptide antigens elicits highly *S. pneumoniae* cross-reactive antibodies in mice when administered alone or in combination with other antigens, without co-administration of an adjuvant.

Example 5

Rabbit Immunization Studies

In order to characterize the antibody response in non-rodents, New Zealand White rabbits were sc immunized three times on days 0, 28 and 56 with different concentrations of conjugates 17, 18 or 19 in 0.4 ml PBS, without or with an adjuvant (R848) (Table 9). Blood samples were taken on days 0, 14, 38 and 66 to determine seroconversion.

TABLE 9

Formulations used for immunizations of rabbits

| Group | Formulation | Adjuvant | Concentration (mg/ml)[a] |
|---|---|---|---|
| 1 | 17 in PBS | None | 0.35 |
| 2 | 22 in PBS | None | 0.35 |
| 3 | 21 in PBS | None | 0.1 |
| 4 | 21 in PBS | None | 0.025 |
| 5 | 21 in PBS | R848 | 0.025 |

[a]Shown is the lipopeptide concentration.

Pre-immune sera and sera after the third immunization were analyzed by Western Blot and FACS using rabbit-IgG-specific secondary antibodies and various pneumococcal isolates as described above for the mice. The development of the IgG response was also analyzed by ELISA using a monoclonal anti-rabbit IgG (γ-chain specific) alkaline phosphatase antibody with 4-nitrophenyl-phosphate for IgG detection, essentially as described above. Results are shown in Table 10. All immunized rabbits developed IgG binding to endogenously expressed PspA and PspA expressed on intact *pneumococci* in response to the immunization. Pre-immune sera showed no significant reactivity in these assays. High titers of PR peptide-specific IgG antibodies were detected in the immune sera from immunized rabbits, even after administration of low doses of the conjugate without an adjuvant.

TABLE 10

Development of the IgG response In NZW rabbits (N = 3)

| Group | ELISA (GMT ± SEM)[a] | | | Western Blot (Pos./ Neg.)[b] | FACS (Pos./ Neg.)[b] |
|---|---|---|---|---|---|
| | 1st imm. | 2nd imm. | 3rd imm. | | |
| 1 | 4.01 ± 0.22 | 4.92 ± 0.15 | 4.66 ± 0.16 | 3/0 | 3/0 |
| 2 | 2.96 ± 0.05 | 4.13 ± 0.19 | 4.15 ± 0.08 | 3/0 | 3/0 |
| 3 | <2.3 | 4.47 ± 0.05 | 4.67 ± 0.16 | 3/0 | 3/0 |
| 4 | <2.3 | 2.84 ± 0.25 | 3.79 ± 0.34 | 3/0 | 3/0 |
| 5 | <2.3 | 3.70 ± 0.38 | 4.56 ± 0.08 | 3/0 | 3/0 |

[a]Shown are log10 Geometric Mean Titers (GMT) ± one Standard Error of the Mean (SEM) after one (1st imm.), two (2nd imm.) or three (3rd imm.) immunizations.
[b]Results for strain SP1577 are shown.

The results demonstrate that immunization with SVLP-forming lipopeptides carrying proline-rich peptide antigens elicits broadly cross-reactive antibodies in non-rodents also when administered without an adjuvant.

Example 6

Comparison of Antigen-Specific Antibody Responses in BALB/c Mice

The antigen-specific antibody response elicited by conjugate 15 SVLPs was compared to that elicited with recombinant PspA protein. Six to eight week-old female BALB/c mice (18 per group) were subcutaneously immunized two times in three-week intervals on days 0 and 21 with 0.1 ml of conjugate 15 in PBS or rPspA+alum in saline prepared as described above in Example 5. Blood was collected ten days after the second immunization.

In order to determine the antigen specificity of the antibody response, ELISA were performed as described in Example 5, using PR peptide SEQ ID NO:27 as the coating antigen for the measurement of PR-specific antibodies and rPspA as the coating antigen for the measurement of total anti-PspA antibodies (i.e. antibodies to N-terminal epitopes, NPB and PR). The results are shown in FIG. 1. Sera from non-immunized mice showed no cross-reactivity with either antigen in ELISA.

As expected rPspA was highly immunogenic (anti-PspA IgG GMT±SEM=81,969±28,068) but failed to elicit significant levels of anti-PR antibodies (anti-PspA IgG GMT±SEM=213±218). This was not due to a failure of antibodies raised against rPspA to bind to the PR peptide, since antibodies raised against conjugate 15 SVLPs recognized both, the PR peptide (anti-PspA IgG GMT±SEM=27,583±6,204) and the rPspA antigen (20,919±3,444) in ELISA. It is, therefore, likely that the majority of rPspA-elicited antibodies bind to epitopes in the N-terminal alpha helical part.

In order to determine whether PspA lacking the N-terminal alpha helical would elicit more PR-specific antibodies, mice were immunized with a truncated recombinant PspA-Trx fusion protein (rPspA-delta-N-term; contains PR and NPB). Surprisingly also the truncated protein failed to elicit significant levels of anti-PR antibodies: The GMT±SEM was 128,496±28,481 for the protein and 213±1,094 for the PR antigen. This was significantly lower than for conjugate 15 SVLP-immunized control animals (GMT±SEM of 32,776±6974 for the protein and 47,679±23,383 for the PR peptide). Together these results indicate that SVLPs elicit significantly higher levels of PR-specific antibodies than recombinant PspA.

Example 7

Protection from Increasing Challenge Doses

In order to determine the protection of immunized BALB/c mice from increasing challenge doses, mice were immunized with conjugate 15 or rPspA as described above in Example 6, challenged intravenously with increasing doses of serotype 1 bacteria ranging from $10^2$ to $10^6$ CFU and monitored for survival. Standardized pneumococcal serotype 1 bacterial inocula were prepared as described in Aaberge I. S. et al., *Microbial Pathogenesis,* 1995, 18, 141-152. $LD_{50}$ in non-immunized mice were verified by intravenously injecting BALB/c mice increasing doses of bacteria and monitoring for survival.

Figure 2:
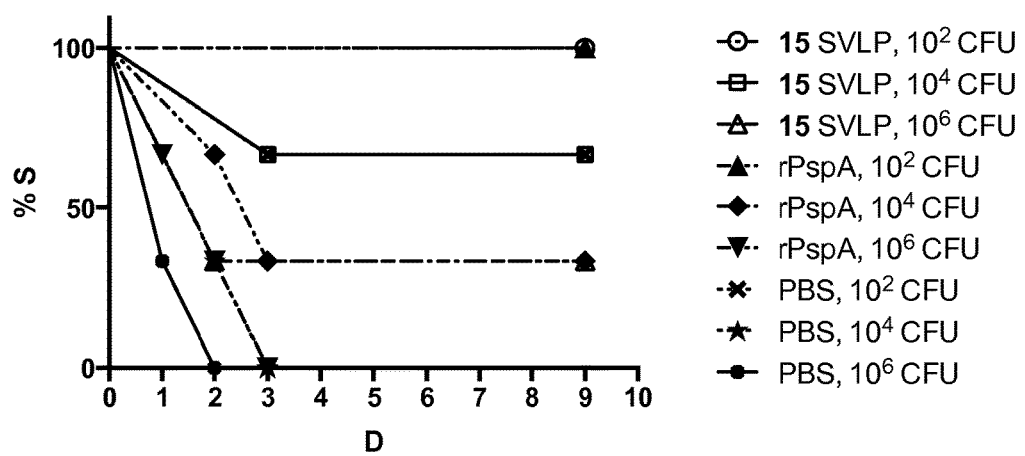
FIG. 2: Survival times in days (D) post challenge of immunized and non-immunized BALB/c mice with increasing doses of *S. pneumoniae* serotype 1. The percent Survival (% S) is shown on the y-axis and immunogens and challenge doses (in CFU) are indicated on the right. Mice were immunized two times with lipopeptide 15 or rPspA+alum and then challenged intravenously.

The protection of immunized mice was dependent on the bacterial challenge dose and the type of immunogen. At low challenge doses the protection was comparable for animals immunized with rPspA or lipopeptide building block 15 SVLPs (See FIG. 2). At higher challenge doses (100-10,000×$LD_{50}$), the mice immunized with conjugate 15 SVLPs were better protected than those immunized with rPspA. Together these results indicate that the anti-PR antibodies elicited by SVLPs protect over a wider range of bacterial challenge doses than antibodies raised against rPspA.

The invention claimed is:

1. The lipopeptide building block consisting of
   (1) a peptide chain comprising a parallel coiled-coil domain which, as a self-standing lipid-free peptide, forms a parallel dimeric, trimeric or higher order oligomeric helical bundle,
   (2) a proline-rich peptide antigen comprising at least one negatively and at least one positively charged amino acid, and wherein at least 15% of the amino acids are proline, optionally linked to a further antigen, and wherein said proline-rich peptide antigen consists of 8-80 amino acids, and wherein said proline-rich peptide antigen comprises any one of sequences selected from the group consisting of SEQ ID NO:27 to 112 or comprises any one of sequences selected from the group consisting of SEQ ID NO:27 to 112 wherein one, two or three amino acids are replaced by other amino acids; and
   (3) a lipid moiety comprising two or three long hydrocarbyl chains,
   wherein the peptide chain, the proline-rich peptide antigen and the lipid moiety are covalently linked, either directly or through a linker.

2. The lipopeptide building block according to claim 1 wherein the peptide chain comprises between 21 and 200 amino acid residues.

3. The lipopeptide building block according to claim 1 wherein the peptide chain comprises a coiled-coil domain consisting of three to eight heptad motifs.

4. The lipopeptide building block according to claim 3 wherein in the coiled-coil domain positions a and d in each heptad motif (abcdefg) comprise alpha-amino acids with small to medium-sized hydrophobic side chains and/or aromatic or heteroaromatic side chains, in zero, one or two of all the a and d positions an amino acid with a polar non-charged residue and in zero or one of all the a and d positions an amino acid with a polar cationic residue or an acylated derivative thereof, or with a polar anionic residue, or glycine.

5. The lipopeptide building block according to claim 4 wherein the alpha-amino acids with small to medium-sized hydrophobic side chain are alanine, isoleucine, leucine, methionine and valine;

the alpha-amino acids with aromatic or heteroaromatic side chain are phenylalanine, tyrosine, tryptophan and histidine;

the alpha-amino acids with polar non-charged residue are asparagine, cysteine, glutamine, serine and threonine;

the alpha-amino acids with polar cationic residue are arginine, lysine and histidine; and the alpha-amino acids with polar anionic residue are aspartic acid and glutamic acid.

6. The lipopeptide building block according to claim 1 wherein the proline-rich peptide antigen comprises at least one glutamic acid residue and at least one lysine or arginine residue.

7. The lipopeptide building block according to claim 1 wherein the proline-rich peptide antigen is an amino acid sequence comprising 50% or more of one or more amino acid sequences from proteins of *Streptococci* and/or *Staphylococci*.

8. The lipopeptide building block according to claim 1 wherein the proline-rich peptide antigen is an amino acid sequence comprising 50% or more of one or more amino acid sequences from proteins PspA and/or PspC.

9. The lipopeptide building block according to claim 1 wherein the lipid moiety is one of types $Z^1$ to $Z^8$

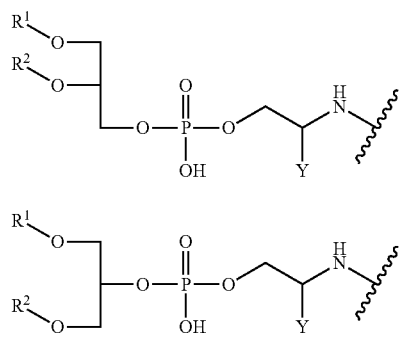

wherein $R^1$ and $R^2$ are long hydrocarbyl or long hydrocarbyl-C=O and Y is H or COOH,

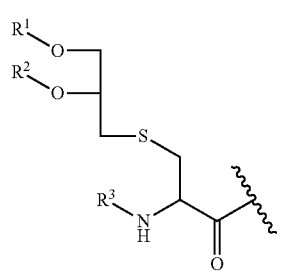

wherein $R^1$, $R^2$ and $R^3$ are long hydrocarbyl or long hydrocarbyl-C=O or $R^1$ and $R^2$ are long hydrocarbyl or long hydrocarbyl-C=O and $R^3$ is H or acetyl or lower alkyl-C=O,

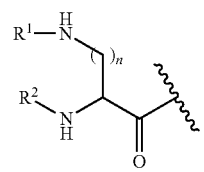

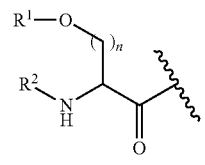

wherein $R^1$ and $R^2$ are long hydrocarbyl or long hydrocarbyl-C=O and n is 1, 2, 3 or 4, or

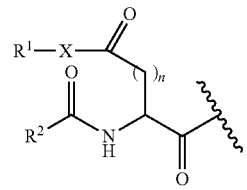

wherein $R^1$ and $R^2$ are long hydrocarbyl, X is O or NH, and n is 1, 2, 3 or 4, or

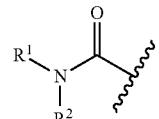

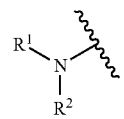

wherein $R^1$ and $R^2$ are long hydrocarbyl, and wherein long hydrocarbyl is straight or branched alkyl or alkenyl consisting of between 8 and 25 carbon atoms and optionally one, two or three double bonds in the chain.

10. The lipopeptide building block according to claim 9 wherein the lipid moiety is di-palmitoyl-S-glycerylcysteinyl of formula $Z^3$, wherein $R^1$ and $R^2$ are palmitoyl and $R^3$ is H or acetyl.

11. The lipopeptide building block according to claim 1 wherein the peptide chain comprising a parallel coiled coil is linked at one end to the PR peptide antigen and at the other end to the lipid moiety.

12. The lipopeptide building block according to claim 11 wherein the peptide chain PC is covalently linked to the lipid moiety LM at or near one terminus of the peptide chain either directly as in

LM-PC  (1)

or via a linker (L) as in

LM-L-PC  (2)

wherein linker L is selected from

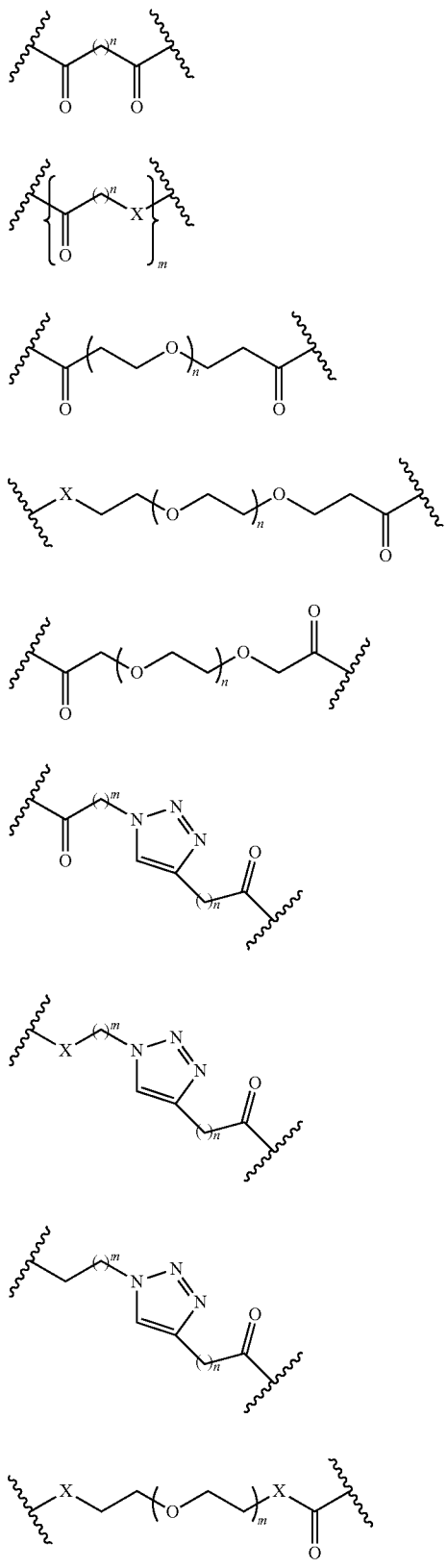

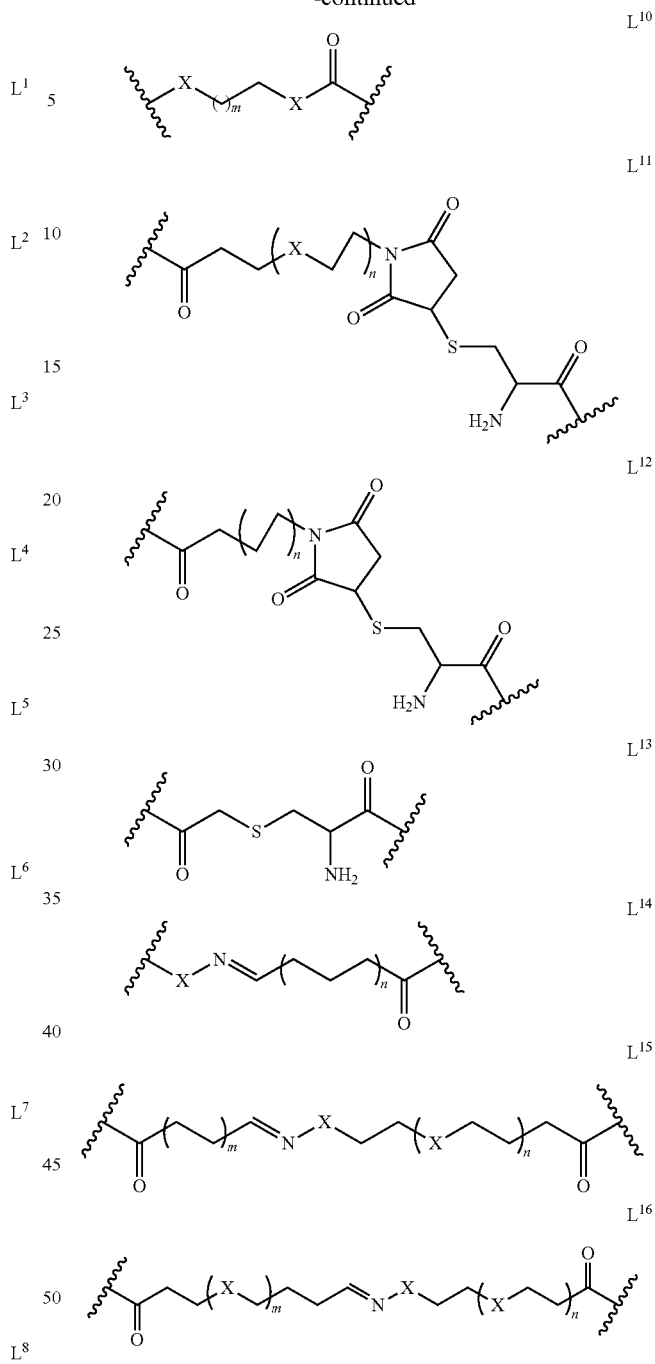

wherein X is O or NH, m is between 1 and 45 and n is between 1 and 45.

13. Synthetic virus-like particles consisting of helical lipopeptide bundles comprising two, three, four, five, six or seven lipopeptide building blocks according to claim 1.

14. A vaccine comprising the synthetic virus-like particle according to claim 13.

15. A method of vaccination against a disease caused by Gram-negative bacteria wherein an immunogenically effective amount of the synthetic virus-like particle according to claim 13 is administered to a patient in need thereof.

16. The lipopeptide building block according to claim 8 wherein said one or more amino acid sequences from proteins PspA and/or PspC are amino acid sequences located after the C-terminal end of the helical region and before the non-proline block of said proteins PspA or PspC.

17. The lipopeptide building block according to claim 1 wherein said proline-rich peptide antigen consists of any one of sequences selected from the group consisting of SEQ ID NO:27 to 112.

18. The lipopeptide building block according to claim 1 wherein said proline-rich peptide antigen consists of any one of sequences selected from the group consisting of SEQ ID NO:27 to 112 wherein one, two or three amino acids are replaced by other amino acids.

19. The lipopeptide building block according to claim 1 wherein said proline-rich peptide antigen consists of any one of sequences selected from the group consisting of SEQ ID NO:27 to 29 or 86.

* * * * *

UNITED STATES PATENT AND TRADEMARK OFFICE
CERTIFICATE OF CORRECTION

| | | |
|---|---|---|
| PATENT NO. | : 9,943,583 B2 | Page 1 of 1 |
| APPLICATION NO. | : 15/101214 | |
| DATED | : April 17, 2018 | |
| INVENTOR(S) | : Arin Ghasparian et al. | |

It is certified that error appears in the above-identified patent and that said Letters Patent is hereby corrected as shown below:

On the Title Page

Under item (72), Inventors, Line 3: "Marco Tamborini" should be replaced with
--Marco Tamborrini--.

In the Claims

Column 111, Line 49 (Claim 1): "The lipopeptide" should be replaced with --Lipopeptide--.

Column 114, Line 31 (Claim 9): "X is 0 or NH" should be replaced with --X is O or NH--.

Signed and Sealed this
Nineteenth Day of March, 2019

Andrei Iancu
*Director of the United States Patent and Trademark Office*